US009447381B2

(12) United States Patent
Gerecht et al.

(10) Patent No.: US 9,447,381 B2
(45) Date of Patent: *Sep. 20, 2016

(54) HYDROGEL-BASED VASCULAR LINEAGE CELL GROWTH MEDIA AND USES THEREOF

(71) Applicant: The Johns Hopkins University, Baltimore, MD (US)

(72) Inventors: Sharon Gerecht, Baltimore, MD (US); Donny Hanjaya-Putra, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/553,442

(22) Filed: Nov. 25, 2014

(65) Prior Publication Data

US 2015/0166962 A1 Jun. 18, 2015

Related U.S. Application Data

(63) Continuation of application No. 13/508,821, filed as application No. PCT/US2010/056268 on Nov. 10, 2010, now Pat. No. 8,900,868.

(60) Provisional application No. 61/259,821, filed on Nov. 10, 2009.

(51) Int. Cl.
*A61L 27/52* (2006.01)
*A61L 27/54* (2006.01)
*A61K 35/44* (2015.01)
*C12N 5/071* (2010.01)
*A61L 27/38* (2006.01)
*A61K 35/12* (2015.01)

(52) U.S. Cl.
CPC ............. *C12N 5/0692* (2013.01); *A61K 35/44* (2013.01); *A61L 27/3808* (2013.01); *A61L 27/52* (2013.01); *A61L 27/54* (2013.01); *C12N 5/069* (2013.01); *A61K 2035/126* (2013.01); *A61L 2300/414* (2013.01); *C12N 2500/34* (2013.01); *C12N 2501/115* (2013.01); *C12N 2501/148* (2013.01); *C12N 2501/165* (2013.01); *C12N 2501/17* (2013.01); *C12N 2501/21* (2013.01); *C12N 2501/998* (2013.01); *C12N 2513/00* (2013.01); *C12N 2533/50* (2013.01); *C12N 2533/80* (2013.01); *C12N 2537/10* (2013.01)

(58) Field of Classification Search
CPC .................. A61K 2035/126; A61L 27/3808; A61L 27/52; A61L 27/54; A61L 2300/414; C12N 5/069; C12N 2537/10; C12N 2501/148; C12N 2501/165; C12N 2501/17; C12N 2501/21; C12N 2533/50; C12N 2533/80
See application file for complete search history.

(56) References Cited

U.S. PATENT DOCUMENTS

| 5,334,640 A | 8/1994 | Desai et al. |
| 5,591,709 A | 1/1997 | Lindenbaum |
| 6,476,204 B1 | 11/2002 | Kim et al. |
| 6,602,952 B1 | 8/2003 | Bentley et al. |
| 7,799,767 B2 | 9/2010 | Lamberti et al. |
| 2002/0081729 A1 | 6/2002 | Peters et al. |
| 2004/0151752 A1 | 8/2004 | Won et al. |
| 2006/0024357 A1 | 2/2006 | Carpenter et al. |
| 2008/0020015 A1 | 1/2008 | Carpenter et al. |
| 2009/0022777 A1 | 1/2009 | Mathiowitz et al. |
| 2009/0130755 A1 | 5/2009 | Detamore et al. |
| 2009/0280182 A1 | 11/2009 | Beck et al. |
| 2011/0275565 A1 | 11/2011 | Gerecht et al. |
| 2012/0225814 A1 | 9/2012 | Hanjaya-Putra et al. |

FOREIGN PATENT DOCUMENTS

| WO | WO-03/072155 A1 | 9/2003 |
| WO | WO-2006/060779 A2 | 6/2006 |
| WO | WO-2008/098019 A2 | 8/2008 |
| WO | WO-2010/078036 A2 | 7/2010 |
| WO | WO-2011/060095 A2 | 5/2011 |
| WO | WO-2012/003370 A2 | 1/2012 |
| WO | WO-2012/158312 A2 | 11/2012 |

OTHER PUBLICATIONS

Adams et al., "Stem Cell Therapy for Vascular Disease," Trends in Cardiovascular Medicine, vol. 17, No. 7, pp. 246-51, 2007.
Aicher et al., "Mobilizing Endothelial Progenitor Cells," *Hypertension*, vol. 45, pp. 321-325, 2005.
Asahara et al., "Bone Marrow Origin of Endothelial Progenitor Cells responsible for Postnatal Vasculogenesis in Physiological and Pathological Neovascularization," *Circ. Res.*, vol. 85, pp. 221-228, 1999.
Asahara et al., "Isolation of Putative Progenitor Endothelial Cells for Angiogenesis," *Science*, vol. 275, pp. 964-967, 1997.
Asahara et al., "Synergistic Effect of Vascular Endothelial Growth Factor and Basic Fibroblast Growth Factor on Angiogenesis In Vivo," Circulation, vol. 92, No. 9, pp. 365-71, 1995.
Au et al., "Bone marrow-derived mesenchymal stem cells facilitate engineering of long-lasting functional vasculature," Blood, vol. 111, No. 9, pp. 4551-4558, 2008.
Au et al., "Differential in vivo potential of endothelial progenitor cells from human umbilical cord blood and adult peripheral blood to form functional long-lasting vessels," Blood, vol. 111, pp. 1302-1305, 2008.
Office Action issued in U.S. Appl. No. 13/140,324 dated Oct. 29, 2013.

(Continued)

*Primary Examiner* — Daniel C Gamett
(74) *Attorney, Agent, or Firm* — Venable LLP; Keith G. Haddaway; Miguel A. Lopez

(57) ABSTRACT

A medium for growing vascular lineage cells is described. The vascular lineage cell growth medium includes an oligosaccharide-based hydrogel and a growth factor that promotes vascularization by vascular lineage cells.

21 Claims, 42 Drawing Sheets

(56) References Cited

OTHER PUBLICATIONS

Office Action issued in U.S. Appl. No. 13/508,821 dated Nov. 22, 2013.
Azzam et al., "Dextran-Spermine Conjugate: An Efficient Vector for Gene Delivery," *Macromol. Symp.*, 2003, vol. 195, p. 247.
Banfi et al., "Critical Role of Microenvironmental Factors in Angiogenesis," Curr Atheroscler Rep vol. 7, No. 3, pp. 227-234, 2005.
Bayless et al., "RGD-Dpendent Vacuolation and Lumen Formation Observed during Endothelial Cell Morphogenesis in Three-Dimensional Fibrin Matrices Involves the $\alpha v\beta_3$ and $\alpha 5\beta_1$ Integrins," *Am. J. Pathol.*, vol. 156, No. 5, pp. 1673-1683, 2000.
Bayless et al., "The Cdc42 and Rac1 GTPases are required for capillary lumen formation in three-dimensional extracellular matrices," J. Cell Sci., vol. 115, pp. 1123-1136, 2002.
Bettinger et al., "Enhancement in In Vitro Capillary Tube Formation by Substrate Nanotopography," Adv. Mater., vol. 20, pp. 99-103, 2008.
Bos et al., "Tissue reactions of in situ formed dextran hydrogels crosslinked by stereocomplex formation after subcutaneous implantation in rats," Biomaterials vol. 26, No. 18, pp. 3901-3909, 2005.
Boudou et al., "An extended relationship for the characterization of Young's modulus and Poisson's ratio of tunable polyacrylamide gels," Biorheology, vol. 43, pp. 721-728, 2006.
Burdick et al., "Controlled Degradation and Mechanical Behavior of Photopolymerized Hyaluronic Acid Networks," Biomacromolecules, vol. 6, No. 1, pp. 386-391, 2005.
Cao et al., "The influence of architecture on degradation and tissue ingrowth into three-dimensional poly(lactic-co-glycolic acid) scaffolds in vitro and in vivo," Biomaterials, vol. 27, No. 14, pp. 2854-2864, 2006.
Chen et al., "Disruption of Ang-1/Tie-2 Signaling Contributes to the Impaired Myocardial Vascular Maturation and Angiogenesis in Type II Diabetic Mice," Arterioscler Thromb Vasc Biol vol. 28, No. 9, pp. 1606-1613, 2008.
Chen et al., "Geometric Control of Cell Life and Death," Science vol. 276, pp. 1425-1428, 1997.
Chiu et al., Scaffolds with covalently immobilized VEGF and Angiopoien-1 for vascularization of engineered tissues, Biomaterials, vol. 31, p. 226-241.
Chu, C.C., in: Biomaterials Handbook—Advanced Applications of Basic Sciences, and Bioengineering, D. L. Wise (Ed.), p. 871. Marcel Dekker, New York, NY (2003).
Chun et al., "MT1-MMP-dependent neovessel formation within the confines of the three-dimensional extracellular matrix," J. Cell. Biol., vol. 167, pp. 757-767, 2004.
Chung et al., "Poly(ethylene glycol)-grafted poly(3-hydroxyundecenoate) networks for enhanced blood compatibility," Int. J. Biol. Macromol., 2003, vol. 32, p. 17.
Collen et al., "Membrane-type matrix metalloproteinase-mediated angiogenesis in a fibrin-collagen matrix," Blood, vol. 101, pp. 1810-1817, 2003.
Critser et al., "Collagen matrix physical properties modulate endothelial colony forming cell-derived vessels in vivo." Microvascular Research, vol. 80, pp. 23-30, 2010.
Davis et al., "An $\alpha 2\beta 1$ Integrin-Dependent Pinocytic Mechanism Involving Intracellular Vacuole Formation and Coalescence Regulates Capillary Lumen and Tube Formation in Three-Dimensional Collagen Metric," Exp. Cell. Res., vol. 224, pp. 39-51, 1996.
Davis et al., "Endothelial Extracellular Matrix: Biosynthesis, Remodeling, and Functions During Vascular Morphogenesis and Neovessel Stabilization," Circ Res., vol. 97, pp. 1093-1107, 2005.
Davis et al., "Extracellular matrix mediates a molecular balance between vascular morphogenesis and regression," Current Opinion in Hematology, vol. 15, No. 3, pp. 197-203, 2008.
Davis et al., "Mechanisms OCntrolling Human Endothelial Lumen Formation and Tube Assembly in Three-Dimensional Extracellular Matrices," Birth Defects Research Part C—Embryo Today: Reviews, vol. 81, No. 4, pp. 270-285 2007.
Davis et al., "Regulation of Endothelial Cell Morphogenesis by Integrins, Mechanical Forces, and Matrix Guidance Pathways," Exp. Cell Res., vol. 216, pp. 113-123, 1995.
Davis, "The development of the vasculature and its extracellular matrix: a gradual process defined by sequential cellular and matrix remodeling events," Am. J. Physiol. Heart Circ. Physiol., vol. 299, pp. H245-H247, Jun. 2010.
de Jong et al., "Novel Self-assembled Hydrogels by Stereocomplex Formation in Auqeous Solution of Enantiomeric Lactic Acid Oligomers Grafted to Dextran." Macromolecules, 2000, vol. 33, p. 3680.
Delafontaine et al., "Expression, Regulation, and Function of IGF-1, IGF-1R, and IGF-1 Binding Proteins in Blood Vessels," Arterioscler Thromb Vasc Biol, vol. 24, No. 3, pp. 435-44, 2004.
Deroanne et al., "In vitro tubulogenesis of endothelial cells by relaxation of the coupling extracellular matrix-cytoskeleton," Cardiovasc. Res., vol. 49, pp. 647-658, 2001.
Discher et al., "Tissue Cells Feel and Respond to the Stiffness of Their Substrate," Science, vol. 310, pp. 1139-1143, 2005.
Dvir et al., "Prevascularization of cardiac patch on the omentum improves its therapeutic outcomes," Proc Natl Acad Sci U S A vol. 106, No. 35, pp. 14990-14995, 2009.
Edman, et al., "Immobilization of Proteins in Microspheres of Biodegradable Polyacryldextran," I. J. Pharm. Sci. 1980, vol. 69, pp. 838-842.
Ehrbar et al., "Cell-Demanded Liberation of $VEGF_{121}$ From Fibrin Implants Induces Local and Controlled Blood Vessel Growth," Circ Res, vol. 94, No. 8, pp. 1124-1132, 2004.
Elia et al., "Stimulation of in vivo angiogenesis by in situ cross-linked, dual growth factor-loaded, glycosaminoglycan hydrogels," Biomaterials, vol. 31, No. 17, pp. 4630-4638, 2010.
Engler et al., "Matrix Elasticity Directs Stem Cell Lineage Specification," Cell, vol. 126, pp. 677-689, 2006.
Fan et al., "VEGF blockage inhibits angiogenesis and reepithelialization of endometrium," FASEB J, vol. 22, No. 10, pp. 3571-3580 2008.
Ferreira et al., "Bioactive hydrogel scaffolds for controllable vascular differentiation of human embryonic stem cells," Biomaterials, 2007, vol. 28. Iss. 17, pp. 2706-2717.
Ferreira et al., "Vascular Progenitor Cells Isolated From Human Embryonic Stem Cells Give Rise to Endothelial and Smooth Muscle-Like Cells and Form Vascular Networks In Vivo," Circ. Res., vol. 101, pp. 286-294, 2007.
Fleissner et al., "The IGF-1 Receptor as a Therapeutic Target to Improve Endothelial Progenitor Cell Function," Mol Med vol. 14, No. 5-6, pp. 235-237, 2008.
Folkman et al., "Angiogenesis in vitro," Nature, vol. 288, pp. 551-556, 1980.
Galis et al., "Increased Expression of Matrix Metalloproteinases and Matrix Degrading Activity in Vulnerable Regions of Human Atherosclerotic Plaques," J.Clin. Invest., vol. 94, pp. 2493-2503, 1994.
Galvez et al., "Membrane Type 1-Matrix Metalloproteinase Is Activated during Migration of Human Endothelial Cells and Modulates Endothelial Motility and Matrix Remodeling," J. Biol. Chem., vol. 276, pp. 37491-37500, 2001.
Genasetti et al., "Hyaluronan and Human Endothelial Cell Behavior," Connect. Tissue Res., vol. 49, No. 3, pp. 120-123 2008.
Gerecht et al., "Hyaluronic acid hydrogel for controlled self-renewal and differentiation of human embryonic stem cells," Proc. Natl. Acad. Sci. U. S. A., vol. 104, pp. 11298-11303, 2007.
Gerecht et al., 2007 The effect of actin disrupting agents on contact guidance of human embryonic stem cells. Biomaterials, vol. 28, pp. 4068-4077.
Ghosh et al., "Cell adaptation to a physiologically relevant ECM mimic with different viscoelastic properties," *Biomaterials*, vol. 28, pp. 671-679, 2007.
Gobin et al., "Cell migration through defined, synthetic extracellular matrix analogues," FASEB J.: 01-0759fje, pp. 1-16, 2002.
Gong et al., "Double-Network Hydrogels with Extremely High Mechanical Strength," Adv Mater, vol. 15, No. 14, pp. 1155-1158, 2003.
Greenwald et al., "Effective drug delivery by PEGylated drug conjugates," Adv. Drug Deli. Rev., 2003, vol. 55, p. 217.

(56) References Cited

OTHER PUBLICATIONS

Guiducci et al., "Mechanisms of vascular damage in SSc-implications for vascular treatment strategies," Rheumatology vol. 47, suppl. 5, pp. v18-v20, 2008.
Guo et al., 2005 Synthesis and characterization of novel biodegradable unsaturated poly(exter amide)/poly(ethylene glycol) diacrylate hydrogels. Journal of Polymer Science Part A—Polymer Chemistry, vol. 43, No. 17, pp. 3932-3944.
Guo et al., 2007 Biodegradation of unsaturated poly(ester-amide)s and their hydrogels. Biomaterials, vol. 28, pp. 3284-3294.
Haas, "Endothelial cell regulation of matrix metalloproteinases," Can. J. Physiol. Pharmacol., vol. 83, pp. 1-7, 2005.
Han et al., "TNF-α stimulates activation of pro-MMP2 in human skin through NF-κB mediated induction of MT1-MMP," Journal of Cell Science vol. 114, pp. 131-139, 2001.
Hanjaya-Putra et al., "Vascular endothelial growth factor and substrate mechanics regulate in vitro tubulogenesis of endothelial progenitor cells," Journal of Cellular and Molecular Medicine, vol. 14, No. 10, pp. 2436-2447, 2010.
Hanjaya-Putra et al., "Vascular Engineering Using Human Embryonic Stem Cells," Biotechnology Progress, 2009, vol. 25, Iss. 1, pp. 2-6.
Hasan et al., "Adaptation to oxygen deprivation in cultures of human pluripotent stem cells, endothlial progenitor cells, and umilical vein endothelial cells", Am J Physiol Cell Physiol., vol. 298, p. C1527-C1537 Feb. 24, 2010.
Heinze et al., "Functional Polymers Based on Dextran," Polysaccharides li, Springer-Verlag Berlin: Berlin, 2006; p. 199.
Hennick et al. "Novel crosslinking methods to design hydrogels," Adv. Drug Deli. Rev., vol. 54, No. 1, pp. 13-36, 2002.
Hern et al., "Incorporation of adhesion peptides into nonadhesive hydrogels useful for tissue resurfacing," J. Biomed. Mater. Res.., 1998, vol. 39. p. 266.
Hill et al., "Circulating Endothelial Progenitor Cells, Vascular Function and cardiovascular Risk," New England J. Med., vol. 348, pp. 593-600, 2003.
Hirschi et al., "Assessing Identity, Phenotype, and Fate of Endothelial Progenitor Cells," *Arterioscler. Thromb. Vasc. Biol.*, vol. 28, pp. 1584-1595, 2008.
Hosack et al., "Microvascular maturity elicited in tissue treated with cytokine-loaded hyaluronan-based hydrogels," Biomaterials vol. 29, No. 15, 2336-47, 2008.
Hu et al., "Bioactivites of ricin retained and its immunoreactivity to anti-ricin polyclonal antibodies alleviated through pegylation," *Int. J. Biochem. Cell. Biol.*, 2002, vol. 34, p. 396-402.
Ingber et al., "How Does Extracellular Matrix Control Capillary Morphogenesis?" *Cell*, vol. 58, pp. 803-805, 1989.
Ingber et al., "Mechanochemical Switching between Growth and Differentiation during Fibroblast Growth Factor-stimulated Angiogenesis In Vitro: Role of Extracellular Matrix," *J. Cell Biol.*, vol. 109, pp. 317-330, 1989.
Ingber, "Mechanical Signaling and the Cellular Response to Extracellular Matrix in Angiogenesis and Cardiovascular Physiology," Circ. Res., vol. 91, pp. 877-887, 2002.
Ingram et al., "Identification of a novel hierarchy of endothelial progenitor cells using human peripheral and umbilical cord blood," Blood, vol. 104, pp. 2752-2760, 2004.
Ingram et al., "Vessel wall-derived endothelial cells rapidly proliferate because they contain a complete hierarchy of endothelial progenitor cells," Blood, vol. 105, No. 7, pp. 2783-2786, 2005.
International Search Report issued for PCT/US2009/068479 dated Sep. 2, 2010.
International Search Report issued in Application No. PCT/US2010/056268 dated Jul. 28, 2011.
International Search Report issued in Application No. PCT/US2011/042671 dated Feb. 17, 2012.
Iruela-Arispe et al.,"Cellular and Molecular Mechanisms of Vascular Lumen Formation," Dev Cell., vol. 16, pp. 222-231, Feb. 2009.
Ispanovic et al., "Cdc42 and RhoA have opposing roles in regulating membrane type 1-matrix metalloproteinase localization and matrix metalloproteinase-2 activation," Am. J. Physiol. Cell Physiol., vol. 295, pp. C600-C610, 2008.
Ito et al., "Dextran-based in situ cross-linked injectable hydrogels to prevent peritoneal adhesions," Biomaterials, 2007, vol. 28, pp. 3418-3426.
Jaffe et al., "Rho GTPases: Biochemistry and Biology," Annu. Rev. Cell Dev. Biol., vol. 21, pp. 247-269, 2005.
Kamei et al., "Endothelial tubes assemble from intracellular vacuoles In vivo," Nature, vol. 442, pp. 453-456, 2006.
Kaya et al., "VEGF protects brain against focal ischemia without increasing blood-brain permeability when administered intracerebroventicularly," J. Cereb. Blood. Flow. Metab., vol. 25, pp. 1111-1118, 2005.
Keskar et al., "Initial evaluation of vascular ingrowth into superporous hydrogels," J Tissue Eng Regen Med, vol. 3, No. 6, pp. 486-490, 2009.
Khetan et al., "Cellular Encapsulation in 3D Hydrogels for Tissue Engineering," Vis. Exp., (32), pp. 1-4, 2009.
Khetan et al., "Sequential crosslinking to control cellular spreading in 3-dimensional hydrogels," Soft Matter, vol. 5, No. 8, pp. 1601-1606, 2009.
Khetan et al., "Tuning Hydrogel Properties for Applications in Tissue Engineering," Conf. Proc. IEEE Eng. Med. Biol. Soc., vol. 1, pp. 2094-2096, Sep. 2009.
Kilarski et al., "Biomechanical regulation of blood vessel growth during tissue vascularization," *Nat. Med.*, vol. 15, pp. 657-664, May 2009.
Kim et al., "Pore Structure Analysis of Swollen Dextran-Methacrylate Hydrogels by SEM and Mercury Intrusion Porosimetry," *J. Biomed. Mater. Res.*, 2000, vol. 53, pp. 258-266.
Kim et al., "Albumin Release from Biodegradable Hydrogels Composed of Dextran and Poly(Ethylene Glycol) Macromer," *Arch. Pharma. Res.*, 2001, vol. 24, p. 69.
Kim et al., "In Vitro Relase Behavior of Dextran-Methacrylate Hydrogels Using Doxorubicin and other Model Compounds," *J. Biomater. Appl.*, 2000, vol. 15, p. 23.
Kniazeva et al., "Endothelial cell traction and ECM density influence both capillary morphogenesis and maintenance in 3-D," Am. J. Physiol. Cell Physiol., vol. 297, No. 1, pp. C179-C187, May 2009.
Kopecek, "Swell gels," J. Nature 2002, vol. 417, pp. 388-391.
Koumenis et al., "Modulating phyarmacokinetics of an anti-interleukin-8F(ab')2 by amine-specific PEGylation with preserved bioactivity," Int. J. Pharma., 2000, vol. 198, p. 83.
Kraehenbuehl et al., "Cell-responsive hydrogel for encapsulation of vascular cells," Biomaterials vol. 30, No. 26, pp. 4318-4324, 2009.
Langer, "New Methods of Drug Delivery," Science, vol. 249, No. 4976, pp. 1527-1533, 1990.
Lee et al., "Controlled growth factor release from synthetic extracellular matrices," Nature vol. 408, No. 6815, pp. 998-1000, 2000.
Lee et al., Biomacromolecules, 2008; 9(9); 2315-2321.
Leslie-Barbick et al., "Covalently-Immmobolized Vascular Endothelial Growth Factor Promotes Endothelial Cell Tubulogensis in Poly(ethylene glycol) Diacrylate Hydrogels," Journal of Biomaterials Science, Polymer Edition, vol. 20, No. 12, pp. 1763-1779, 2009.
Li et al., "VEGF and PlGF promote adult vasculogenesis by enhancing EPC recruitment and vessel formation at the site of tumor neovascularization," FASEB J., vol. 20, pp. 1495-1497, 2006.
Lo et al., "Cell Movement Is Guided by the Rigidity of the Substrate," Biophys. J., vol. 79, pp. 144-152, 2000.
Lubarsky et al., "Tube Morphogenesis: Making and Shaping Biological Tubes," Cell, vol. 112, pp. 19-28, 2003.
Lutolf et al., "Synthetic biomaterials as instructive extracellular microenvironments for morphogenesis in tissue engireering," Nature Biotechnology, vol. 23, No. 1, pp. 47-55, 2005.
Lutolf et al., "Synthetic matrix metalloproteinase-sensitive hydrogels for the conduction of tissue regeneration: Engineering cell-invasion characteristics," Proc. Natl. Acad. Sci. U S. A., vol. 100, No. 9, pp. 5413-5418, 2003.

(56) References Cited

OTHER PUBLICATIONS

Maia et al., "Synthesis and characterization of new injectable and degradable dextran-based hydrogels," Polymer, 2005, vol. 46, pp. 9604-9614.
Mammoto et al., "A mechanosenstivie transcriptional mechanism that controls angiogenesis," Nature, vol. 457, pp. 1103-1108, Feb. 2009.
Mammoto et al., "Rho signaling and mechanical control of vascular development," Curr. Opin. Hematol., vol. 15, pp. 228-234 2008.
Massia et al., 2002 Surface-immobilized dextran limits cell adhesion and spreading. Biomaterials, vol. 21, pp. 2253-2261.
Matthews et al., "Cellular adaptation to mechanical stress: role of integrins, Pho, cytoskeletal tension and mechanosensitive ion channels," J. Cell Sci., vol. 119, pp. 508-518, 2006.
McBeath et al., "Cell Shape, Cytoskeletal Tension, and RhoA Regulate Stem Cell Lineage Commitment", Dev. Cell., vol. 6, pp. 483-495, 2004.
Mead et al., "Isolation and Characterization of Endothelial Progenitor Cells from Human Blood," Current protocols in stem cell biology, vol. 6, pp. 2C.1.1-2C.1.27, 2008.
Melero-Martin et al., "Engineering Robust and Functional Vascular Networks In Vivo With Human Adult and Cord Blood-Derived Progenitor Cells," Circulation Research, vol. 103, No. 2, pp. 194-202, 2008.
Mikos et al., "Prevascularization of Porous Biodegradable Polymers," Biotechnol Bioeng, vol. 42, No. 6, pp. 716-723, 1993.
Moon et al., "Biomimetic hydrogels with pro-angiogenic properties," Biomaterials, vol. 31, No. 14, pp. 3840-3847, 2010.
Moore et al., "Control of Basement Membrane Remodeling and Epithelial Branching Morphogenesis in Embryonic Lung by Rho and Cytoskeletal Tension," Dev. Dyn. vol. 232, pp. 268-281, 2005.
Murphy et al., "Sustained release of vascular endothelial growth factor from mineralized poly(lactide-co-glycolide) scaffolds for tissue engineering," Biomaterials, vol. 21, No. 24, pp. 2521-2527, 2000.
Muslim et al., "Synthesis and bioactivites of poly(ethylene glycol)-chitosan hybrids," Carbohydr. Polym., 2001, vol. 46. p. 323-330.
Peattie et al., "Stimulation of in vivo angiogenesis by cytokine-loaded hyaluronic acid hydrogel implants," Biomaterials vol. 25, No. 14, pp. 2789-2798, 2004.
Pelham et al., "Cell locomotion and focal adhesions are regulated by substrate flexibility," Proc. Natl. Acad. Sci. U. S. A., vol. 94, pp. 13661-13665, 1997.
Peppas et al., "Hydrogels in pharmaceutical formulations," Europ. J. Pharma. Biopharma., 2000, vol. 50, p. 27.
Peppas et al., 1985 The structure of highly crosslinked poly(2-hydroxyethyl methacrylate) hydrogels. Journal of Biomedical Materials Research, vol. 19, pp. 397-411.
Perets et al., "Enhancing the vascularization of three-dimensional porous alginate scaffolds by incorporating controlled release basic fibroblast growth factor microspheres," J Biomed Mater Res Part A, vol. 65A, No. 4, pp. 489-497, 2003.
Perkins et al., "Conventional and Immunoelectron Microscopy of Mitchondria," Methods Mol. Biol., vol. 372, pp. 467-483, 2007.
Petit et al., "The SDF-1-CXCR4 signaling pathway: a molecular hub modulating neo-angiogenesis," Trends Immunol vol. 28, No. 7, pp. 299-307, 2007.
Phelps et al., "Bioartificial matrices for therapeutic vascularization," Proc Natl Acad Sci U S A, vol. 107, No. 8, pp. 3323-3328, 2010.
Pike et al., "Heparin-regulated release of growth factors in vitro and angiogenic response in vivo to implanted hyaluronan hydrogels containing VEGF and bFGF," Biomaterials, vol. 27, No. 30, pp. 5242-5251, 2006.
Prater et al., "Working hypothesis to redefine endothelial progenitor cells," Leukemia, vol. 21, pp. 1141-1149, 2007.
Prior et al., "What makes vessels grow with exercise training?" J Appl Physiol vol. 97, No. 3, pp. 1119-1128, 2004.
Raeber et al., "Molecularly Engineered PEG Hydrogels: A Novel Model System for Proteolytically Mediated Cell Migration," Biophysical Journal, vol. 89, No. 2, pp. 1374-1388, 2005.
Rafii et al., "Therapeutic stem and progenitor cell transplantation for organ vascularization and regeneration," Nat Med, vol. 9, No. 6, pp. 702-712, 2003.
Ravi et al., "Biomaterials for vascular tissue engineering," Regenerative Medicine vol. 5, No. 1, 107-20, 2010.
Richardson et al., "Polymeric system for dual growth factor delivery," Nat Biotech vol. 19, No. 11, pp. 1029-1034, 2001.
Riley et al., "Stimulation of in vivo angiogenesis using dual growth factor-loaded crosslinked glycosaminoglycan hydrogels,"Biomaterials vol. 27, No. 35, pp. 5935-5943, 2006.
Romanic et al., "Matrix Metalloproteinase Expression Increases After Cerebral Focal Ischemia in Rats: Inhibition of Matrix Metalloproteinase-9 Reduces Infarct Size," Stroke, vol. 29, pp. 1020-1030, 1998.
Sacharidou et al., "Endothelial lumen signaling complexes control 3D matrix-specific tubulogenesis through interdependent Cdc42- and MT1-MMP-mediated events," Blood, vol. 115, No. 25, pp. 5259-5269, 2010.
Sales et al., "Advancing vascular tissue engineering: the role of stem cell technology," Trends Biotechnol, vol. 23, No. 9, pp. 461-467, 2005.
Saunders et al., "Coregulation of vascular tube stabilization of endothelial cell TIMP-2 and pericyte TIMP-3," J. Cell Biol., vol. 175, pp. 179-191, 2006.
Schatteman et al., "Blood-derived angioblasts accelerate blood-flow restoration in diabetic mice," J. Clin. Invest., vol. 106, pp. 571-578, 2000.
Seliktar et al., "MMP-2 senstive, VEGF-bearing bioactive hydrogels for promotion of vascular healing," J. Biomed. Mater. Res. A, vol. 68, No. 4, pp. 704-716, 2004.
Shepherd et al., "Vascularization and engraftment of a human skin substitute using circulating progenitor cell-derived endothelial cells," FASEB J., vol. 20, pp. 1739-1741, 2006.
Sheridan et al., "Bioabsorbable polymer scaffolds for tissue engineering capable of sustained growth factor delivery," J Controlled Release, vol. 64, No. 1-3, pp. 91-102, 2000.
Shu et al., "Synthesis and evaluation of injectable, in situ crosslinkable synthetic extracellular matrices for tissue engineering," J. Biomed. Mater. Res. A, vol. 79, pp. 902-912, 2006.
Shu et al., "Attachment and spreading of fibroblasts on an RGD peptide-modified injectable hyaluronan hydrogel," J. Biomed Materials Research, vol. 68, No. 2, 2004.
Sieminski et al., "Primary sequence of ionic self-assembling peptide gels affects endothelial cell adhesion and capillary morphogenesis," Journal of Biomedical Materials Research, vol. 87A, No. 2, pp. 494-504, 2008.
Sieminski et al., "The relative magnitudes of endothelial force generation and matrix stiffness modulate capillary morphogenesis in vitro," Exp. Cell. Res., vol. 297, pp. 574-584, 2004.
Sieminski et al., "The Stiffness of Three-dimensional Ionic Self-assembling Peptide Gels Affects the Extent of Capillary-like Network Formation," Cell Biochem. Biophys., vol. 49, pp. 73-83, 2007.
Silva et al., "Material-based deployment enhances efficacy of endothelial progenitor cells," Proceedings of the National Academy of Sciences, vol. 105, No. 38, pp. 14347-14352, Sep. 2008.
Srivastava et al.. "Potential of stem-cell-based therapies for heart disease," Nature vol. 441, No. 7079, pp. 1097-1099, 2006.
Stephanou et al., "The rigidity in fibrin gels as a contributing factor to the dynamics of in vitro vascular cord formation," Microvascular Research, vol. 73, No. 3, pp. 182-190, 2007.
Stratman et al., "Endothelial cell lumen and vascular guidance tunnel formation requires MT1-MMP-dependent proteolysis in 3-dimensional collagen matrices," Blood, vol. 114, No. 2, pp. 237-247, Apr. 2009.
Sun et al., "Effects of Precursor and Cross-linking Parameters on the Properties of Dextran-Allyl Isocyanate-Ethylmine/Poly(ethylene glycol diacrylate) Biodegradable Hydrogels and Their Release of Ovalbumin," J Biomater Sci-Polym Ed vol. 20, No. 14, pp. 2003-2022, 2009.
Sun et al., "Functional groups affect physical and biological properties of dextran-based hydrogels," J Biomed Mater Res Part A, vol. 93A, No. 3, pp. 1080-1090, 2010.

(56) References Cited

OTHER PUBLICATIONS

Sun et al., "Functional neovascularization of biodegradable dextran hydrogels with mlultiple angiogenic growth factors," Biomaterials, vol. 32, p. 95, 2011.
Sun et al., "Synthesis, characterization of biodegradable dextran-allyl isocyanate-ethylamine/polyethylene glycol-diacrylate hydrogels and their in vitro release of albumin," Carbohydrate Polymers, vol. 65, pp. 273-287, 2006.
Sun et al., "Vascular regeneration: engineering the stem cell microenvironment," Regenerative Medicine, vol. 3, No. 3, 435-47, 2009.
Sun et al., "VEGF-induced neuroprotection, neurogenesis, and angiogenesis after focal cerebral ischemia," J. Clin. Invest., vol. 111, pp. 1843-1851, 2003.
Timmermans et al., "Endothelial progenitor cells: identity defined?" J. Cell. Mol. Med., vol. 13, pp. 87-102, 2009.
Toole, "Hyaluronan in morphogenesis," Semin. Cell. Dev. Biol., vol. 12, No. 2, pp. 79-87, 2001.
Toole, "Hyaluronan: From Extracellular Glue to Pericellular Cue," Nat Rev Cancer, vol. 4, No. 7, pp. 528-539, 2004.
Urbich et al., "Endothelial Progenitor Cells: Characterization and Role in Vascular Biology," Circ Res, vol. 95, No. 4, pp. 343-353, 2004.
Van Hinsbergh et al., "Pericellular Proteases in Angiogenesis and Vasculogenesis," Arterioscler. Thromb. Vasc. Biol., vol. 26, pp. 716-728, 2006.
Van Tomme et al. "Biodegradable dextran hydrogels for protein delivery applications," Expert Rev. Med. Dev. 2007, vol. 4, pp. 147-164.
Van Tomme et al., "Degradation behavior of dextran hydrogels composed of positively and negatively charged microspheres," Biomaterials, 2006, vol. 27, p. 4141.
Vanderhooft et al., "Rheological Properties of Cross-Linked Hyaluronan-Gelatin hydrogels for Tissue Engineering," Macromolecular Bioscience, vol. 9, No. 1, pp. 20-28, 2009.
van Dijk-Wolthuis et al., "A new class of polymerizable dextrans with hydrolyzable groups: hydroxyethyl methacrylated dextran with and without oligolactate spacer," Polymer, 1997, vol. 38, pp. 6235-6242.
van Dijk-Wolthuis et al., "Degradation and Release Behavior of Dextran-Based Hydrogels," Macromolecules, 1997, vol. 30, pp. 4639-4645.
van Dijk-Wolthuis et al., "Synthesis, Characterization, and Polymerization of Glycidyl Methacrylate Derivatized Dextran," Macromolecules, 1995, vol. 28, pp. 6317-6322.
Wang et al., "Plasma-induced immobilization of poly(ethylene glycol) onto poly(vinylidene fluoride) microporous membrane," J. Membr. Sci., 2002, vol. 195, p. 103-114.
Wang et al., 2002 A tough biodegradable elastomer. Nature Biotechnology, vol. 20, No. 6, pp. 602-606.
Wang et al., 2003 In vivo degradation characteristics of poly(glycerol sebacate). Journal of Biomedical Materials Research, vol. 66A, No. 1, pp. 192-197.
Won et al., "Dextran-estrone conjugate: synthesis and in vitro release study," Carbohydr. Polym., 1998, vol. 36, p. 327-334.
Won et al., in: Biomaterials & Engineering Handbook, D. L. Wise (Ed.), p. 356. Marcel Dekker, New York, NY (2000) (3 pages).
Written Opinion of the International Search Authority issued in Application No. PCT/US2011/042671 dated Feb. 17, 2012.
Written Opinion of the International Searching Authority issued in Application No. PCT/US2009/068479 dated Sep. 2, 2010.
Written Opinion of the International Searching Authority issued in Application No. PCT/US2010/056268 dated Jul. 28, 2011.
Written Opinion of the International Searching Authority issued in Application No. PCT/US2012/034802 dated Nov. 26, 2012.
Xu et al., "Proteolytic exposure of a cryptic site within collagen type IV is required for angiogenesis and tumor growth in vivo," The Journal of Cell Biology, vol. 154, No. 5, pp. 1069-1080, 2001.
Yang et al., "The Design of Scaffolds for Use in Tissue Engineering," Tissue Engineering vol. 7, No. 6, 679-89, 2001.
Yoder et al., "Redefining endothelial progenitor cells via clonal analysis and hematopoietic stem/progenitor cell principals," Blood, vol. 109, pp. 1801-1809, 2007.
Yoder, "Defining human endothelial progenitor cells," Journal of Thrombosis and Haemostasis, vol. 7, Suppl. 1, pp. 49-52, 2009.
Yoder, "Is Endothelium the Origin of Endothelial Progenitor Cells?" Arterioscler. Thromb. Vasc. Biol., vol. 30, No. 6, pp. 1094-1103, May 2010.
Zaman et al., "Migration of tumor cells in 3D matrices is governed by matrix stiffness along with cell-matrix adhesion and proteolysis," Proceedings of the National Academy of Sciences, vol. 103, No. 29, pp. 10889-10894, 2006.
Zhang et al., "In vitro Release Behavior of Insulin from Biodegradable Hybrid Hydrogel Networks of Polysaccharide and Synthetic Biodegradable Polyester," J. Biomater. App., 2002, vol. 16, p. 305-325.
Zhang et al., "Properties and biocompatibility of chitosan films modified by blending with PEG," Biomaterials, 2002, vol. 23, p. 2641-2648.
Zhang et al., "Synthesis and Characterization of Biodegradable Hydrophobic-Hydrophilic Hydrogel Networks with a Controlled Swelling Property," J. Polym. Sci. Polym. Chem., 2000, vol. 38, pp. 2392-2404.
Zhang et al., "Synthesis and Characterization of Biodegradable Network Hydrogels Having Both Hydrophobic and Hydrophilic Components with Controlled Swelling Behavior," J. Polym. Sci. Polym. Chem., 1999, vol. 37, pp. 4554-4569.
Zhang et al., 2003 Novel Biodegradable and thermosensitive dex-ai/pnipaam hydrogel. Macromolecular Bioscience, vol. 3, pp. 87-91.
Zhang et al., 2004 Temperature sensitive dendrite-shaped pnjp/am/dex-ai hybrid hydrogel particles: formulation and properties. European Polymer Journal, vol. 40, pp. 2251-2257.
Balakrishnan et al., Biomaterials, vol. 26, No. 32, pp. 6335-6342, 2005.
Boucard et al. Biomaterials, vol. 28, No. 24, pp. 3478-3488, 2007.
Cubison et al., Burns, vol. 32, No. 8, pp. 992-999, 2006.
Extended European Search Report issued in European Application No. 10830680.4 dated Jun. 2, 2014.
Extended European Search Report issued in European Application No. 12786297.7 dated Jan. 12, 2015.
Fagenholz et al., J Burn Care Res, vol. 28, No. 5, pp. 681-690, 2007.
Flamme et al., Developmental Biology, vol. 169, No. 2, pp. 699-712, 1995.
Fox et al., British Journal of Surgery, vol. 95, No. 2, pp. 244-251, 2008.
Gill et al., Circ Res vol., 88, No. 2, pp. 167-174, 2001.
Greenhalgh, The International Journal of Biochemistry & Cell Biology, vol. 30, No. 9, pp. 1019-1030, 1998.
Gurtner et al., Nature, vol. 453, No. 7193, pp. 314-321, 2008.
Hanjaya-Putra D, et al., Blood, vol. 118, No. 3, pp. 804-815, 2011.
Hanjaya-Putra et al., "Vascular Engineering Using Human Embryonic Stem Cells", Biotechnology Progress, American Institute of Chemical Engineers, US, vol. 25, No. 1, Feb. 3, 2009, pp. 2-9.
Hao et al, "Angiogenic Effects of Sequential Release of VEGF-A 165 and PDGF-BB With Alginate Hydrogels After Myocardial Infarction." Cardiovascular Research. 2007; 75(1):178-185.
Haroon et al., The FASEB Journal, vol. 13, No. 13, pp. 1787-1795, 1999.
Inoue et al., PLoS ONE, vol. 3, No. 8, p. e3068, 2008.
Ismail et al., Cardiovasc Pathol, vol. 12, No. 2, pp. 82-90, 2003.
Ito et al., Nature, vol. 447, No. 7142, pp. 316-320, 2007.
Kim et al., Biomaterials, vol. 30, No. 22, pp. 3742-3748, 2009.
Kim et al., J Invest Dermatol, vol. 128, No. 7, pp. 1812-1820, 2008.
Kirker et al., Biomaterials, vol. 23, No. 17, pp. 3661-3671, 2002.
Kiyozumi et al., Burns, vol. 33, No. 5, pp. 642-648, 2007.
Kiyozumi et al., Journal of Biomedical Materials Research Part B: Applied Biomaterials, vol. 79B, No. 1, pp. 129-136, 2006.
Kloxin et al., Science, vol. 324, No. 5923, pp. 59-63, 2009.
Kurisawa et al., "Modulated degradation of dextran hydrogels grafted with poly(N-isoproprylacrylamide-co-N,N-dimethylacrylamide) in response to temperature," Macromolecular Chemistry and physics, 199(11), pp. 2613-2618, 1998.

(56) References Cited

OTHER PUBLICATIONS

Lee et al., Mol Ther, vol. 15, No. 6, pp. 1189-1194, 2007.
Li et al., Microscopy Research and Technique, vol. 60, No. 1, 107-114, 2003.
Light et al., J Burn Care Rehabil, vol. 25, No. 1, pp. 33-44, 2004.
Liu et al., Biomaterials, vol. 30, No. 8, pp. 1453-1461, 2009.
Lombardo et al., "Crosslinked Carboxymethylcellulose Hydrogels: Versatile Platforms for Studying Cellular Behaviour in 3D Biomaterials." Transactions of the 32nd Annual Meeting of the Society for Biomaterials, vol. 30:25, 2007, Annual Meeting. http//jleachlab.org/people/lombardo.html (May 12, 2015). 2 printed pages.
Madsen et al., Biomacromolecules, vol. 9, No. 8, pp. 2265-2275, 2008.
Martin, Science, vol. 276, No. 5309, pp. 75-81, 1997.
Millius et al., Methods Mol. Biol., vol. 571, pp. 167-177, 2009.
Office Action issued in U.S. Appl. No. 13/807,502 dated Mar. 27, 2015.
Office Action issued in U.S. Appl. No. 14/115,237 dated Jun. 24, 2015.
Office Action issued in U.S. Appl. No. 14/115,237 dated Nov. 6, 2015.
Peichev et al., Blood, vol. 95, No. 3, pp. 952-958, 2000.
Puolakkainen et al., Journal of Surgical Research, vol. 58, No. 3, pp. 321-329, 1995.
Sase et al., J Cell Sci, vol. 122, No. 18, pp. 3303-3311, 2009.
Schulz et al., Annual Review of Medicine, vol. 51, No. 1, pp. 231-244, 2000.
Sen et al., J. Burn Care Res., vol. 31, No. 6, pp. 836-848, 2010.
Shepherd et al., Biomaterials, vol. 32, No. 1, pp. 258-267, 2011.
Sibal et al., Diabetologia, vol. 52, No. 8, pp. 1464-1473, 2009.
Singer et al., New England Journal of Medicine, vol. 341, No. 10, pp. 738-746, 1999.
Steed, Surgical Clinics of North America, vol. 77, No. 3, pp. 575-586, 1997.
Sun et al., "Dextran hydrogel scaffolds enhance angiogenic responses and promote complete skin regeneration during burn wound healing," PNAS, 2011, vol. 108, No. 52, pp. 20976-20981.
Tibbs, *Radiotherapy and Oncology*, vol. 42, No. 2, pp. 99-106, 1997.
Tredget, *Journal of Trauma-Injury Infection and Critical Care*, vol. 62, No. 6, pp. S69-S69, 2007.
Zhang et al., "A novel PH- and ionic-strength-sensitive carboxy methyl dextran hydrogel." Biomaterials, vol. 26, 2005, pp. 4677-4683.
Zhang et al., *Arch Surg*, vol. 145, No. 3, pp. 259-266, 2010.
Zhang et al., *Wound Repair Regen.*, vol. 18, No. 2, pp. 193-201, 2010.

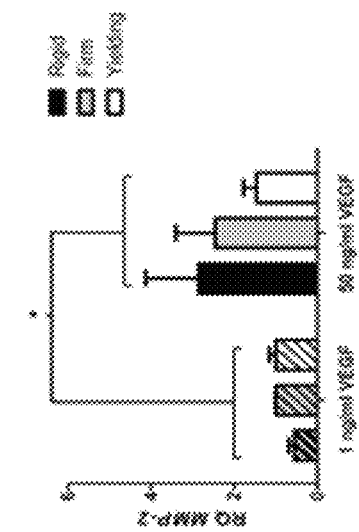 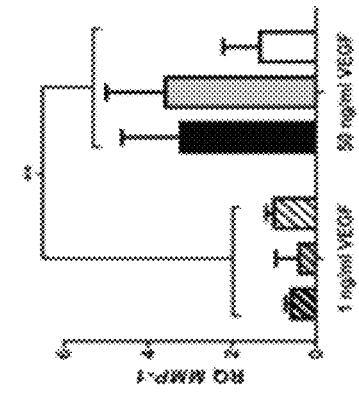 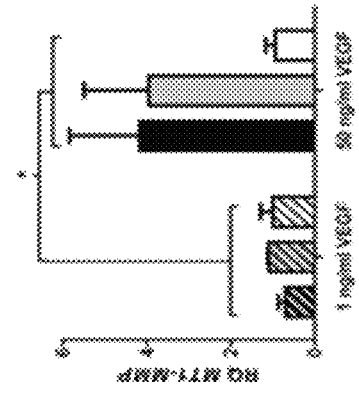
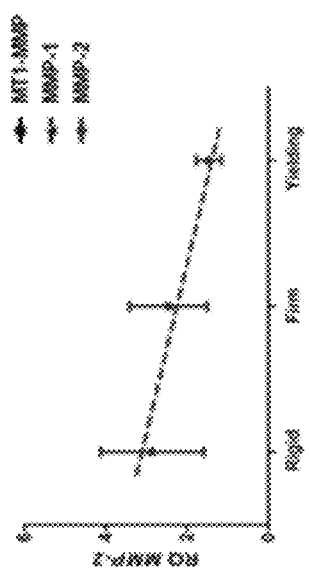 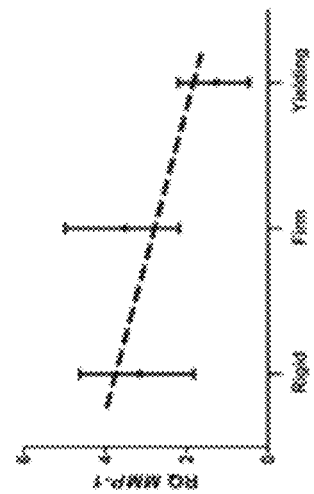 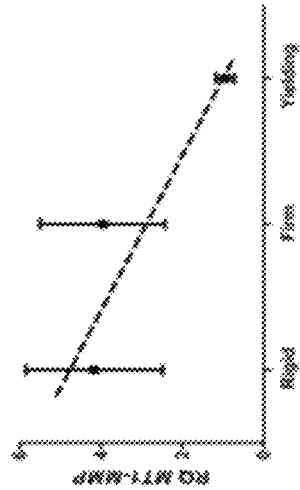
FIG. 2B  FIG. 2C  FIG. 2D
FIG. 2E  FIG. 2F  FIG. 2G

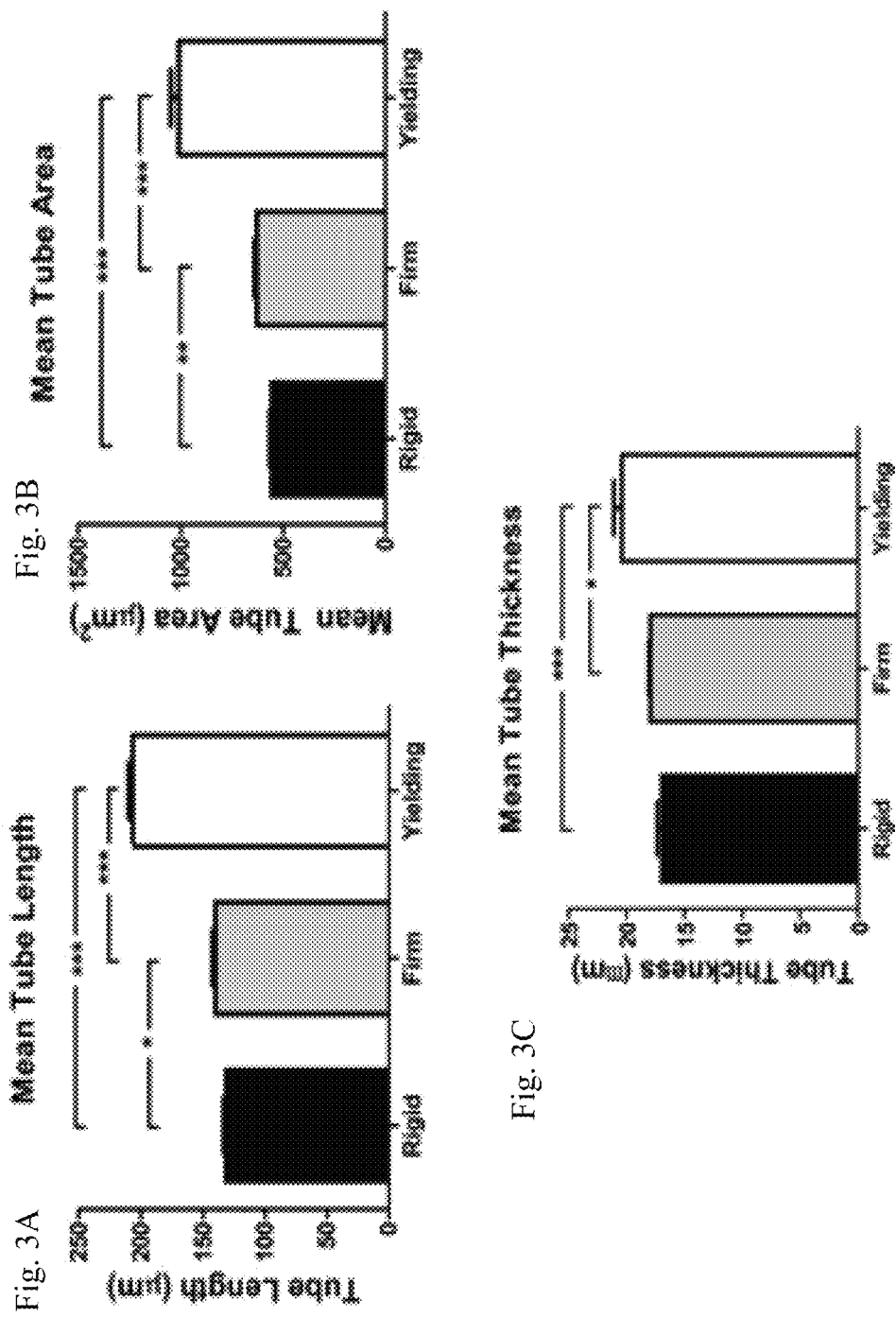

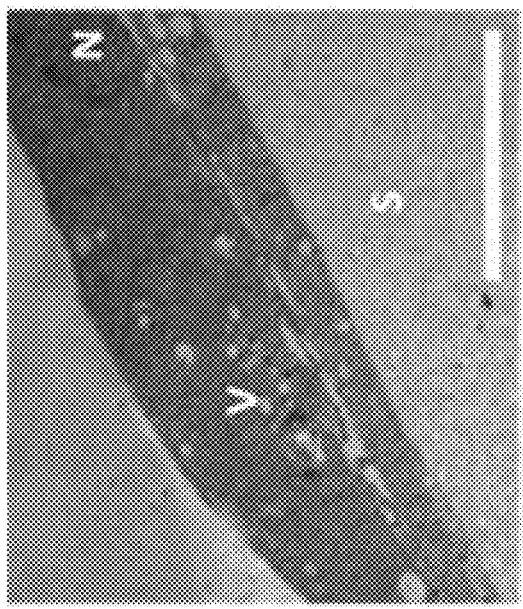
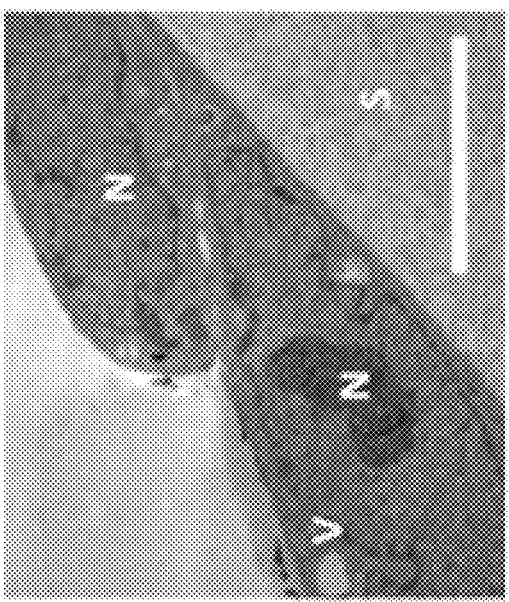
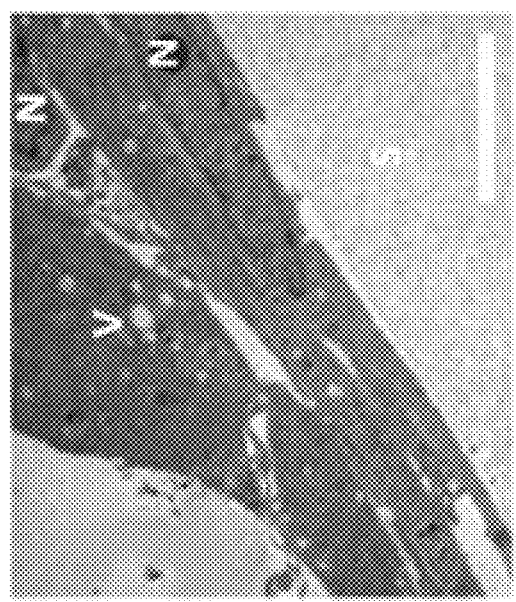
Fig. 4A
Fig. 4B
Fig. 4C

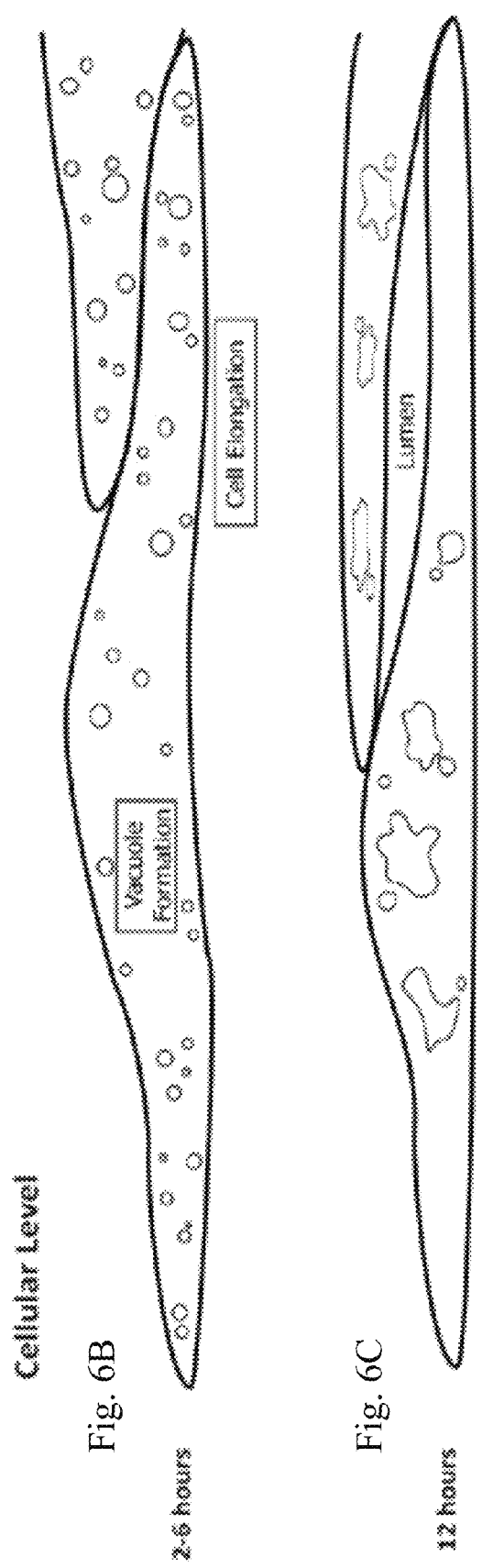

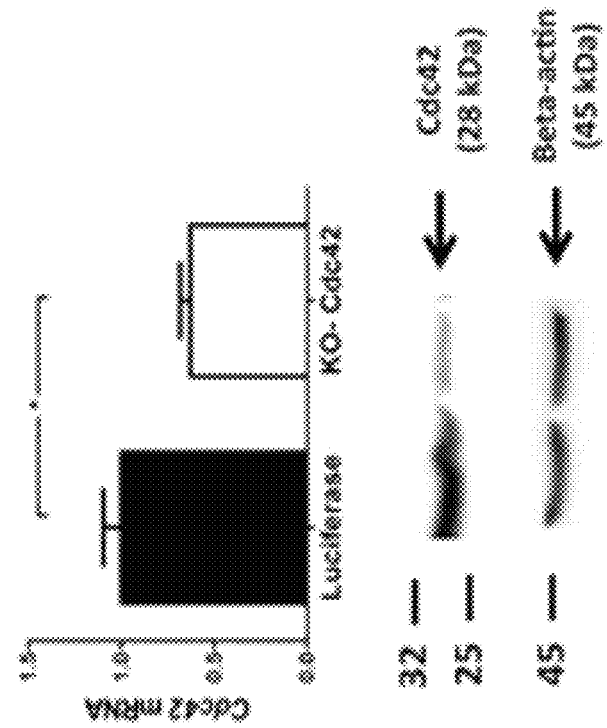
Fig. 9B
Fig. 9D
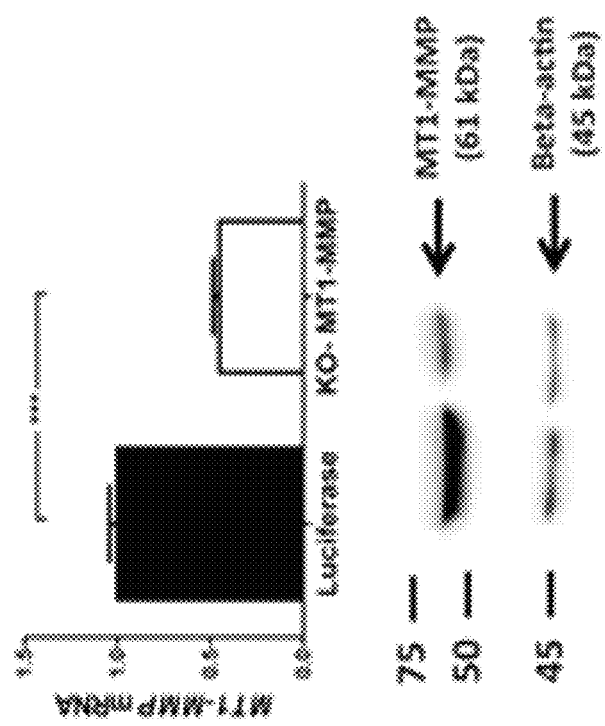
Fig. 9A
Fig. 9C

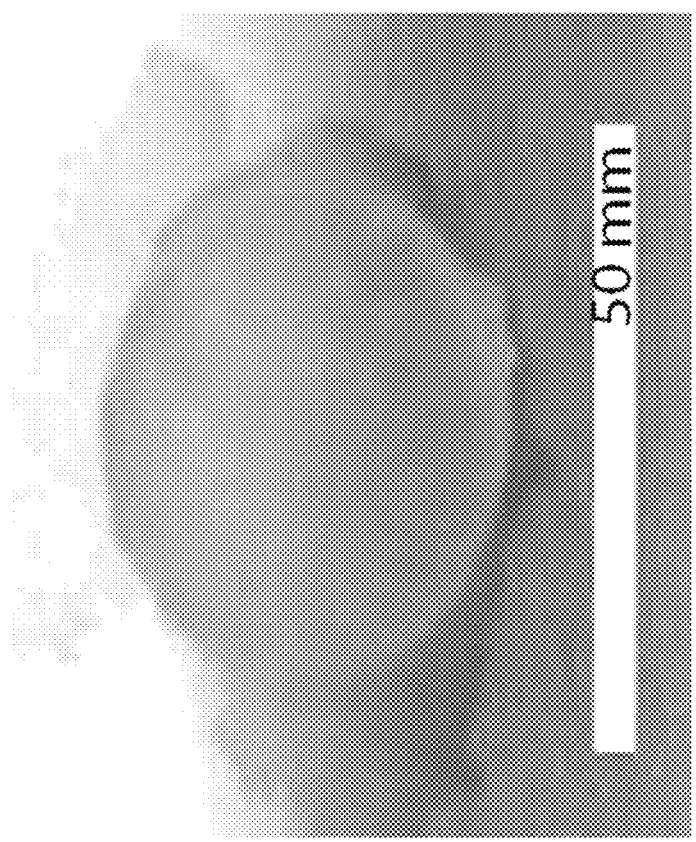
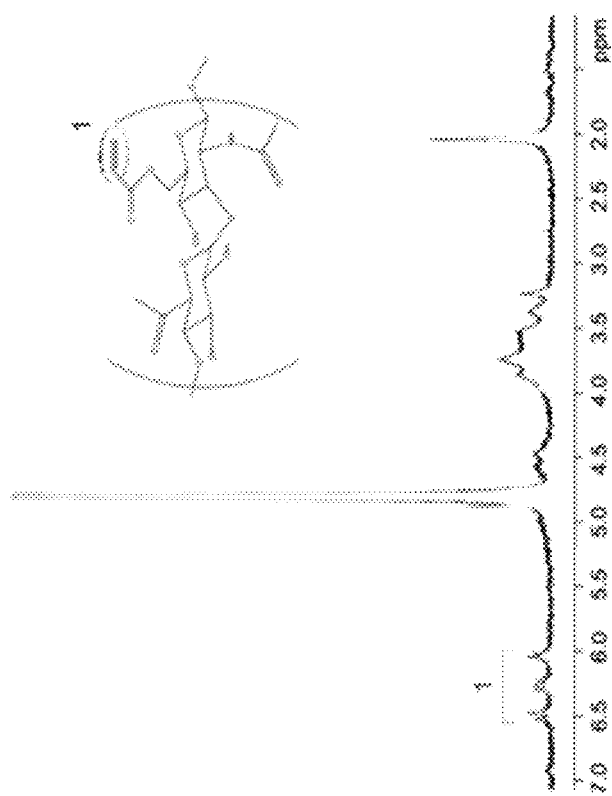
Fig. 10B
Fig. 10C

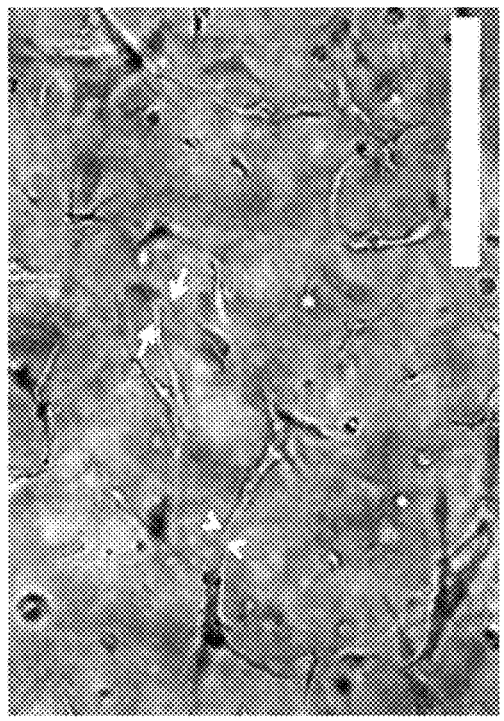
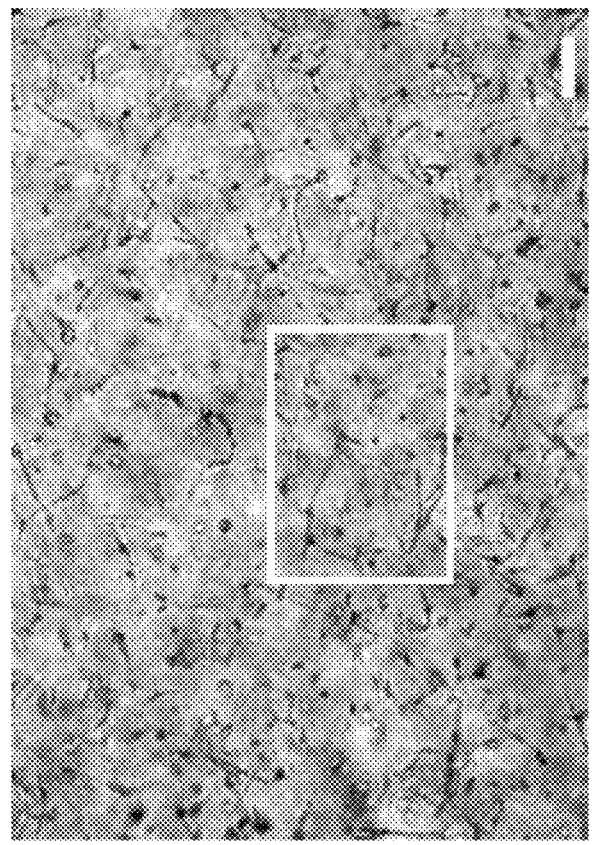

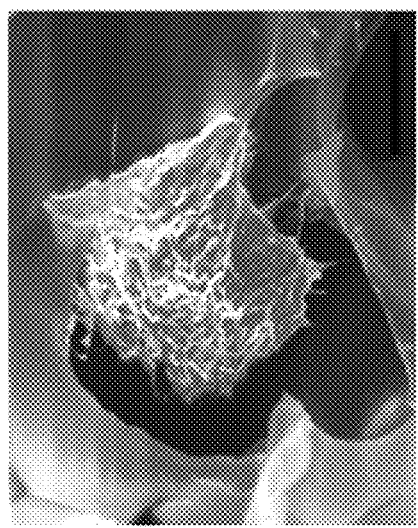
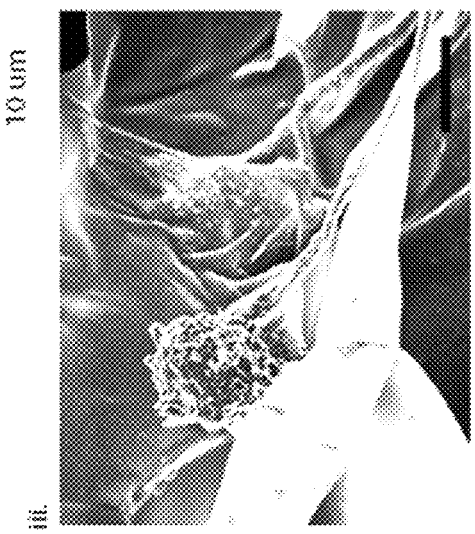
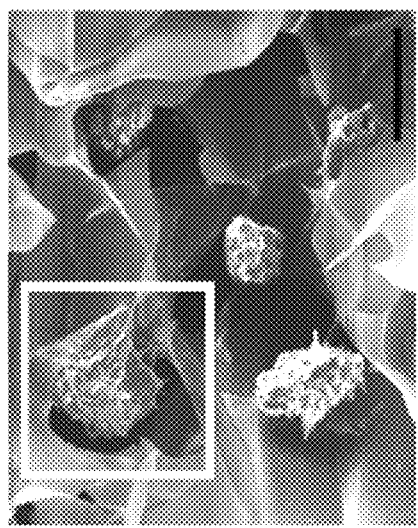
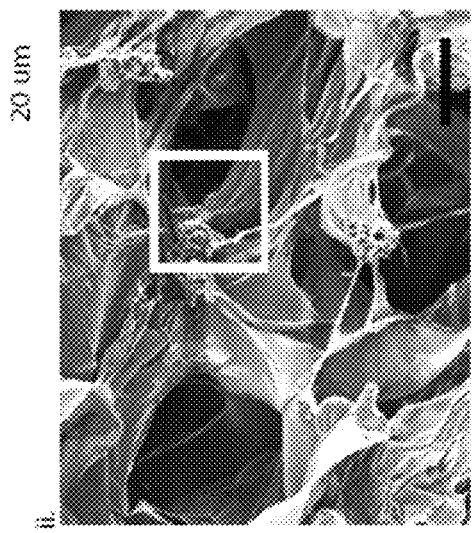
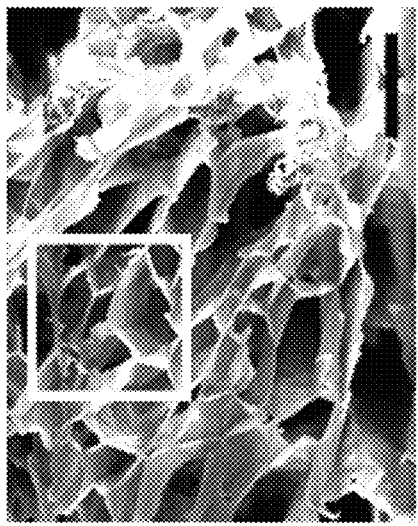
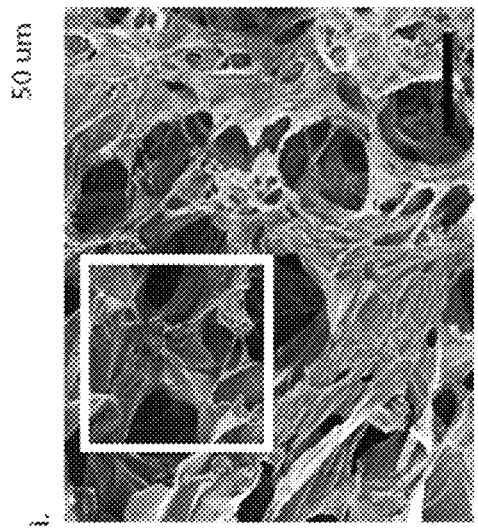
Fig. 15B
Fig. 15C

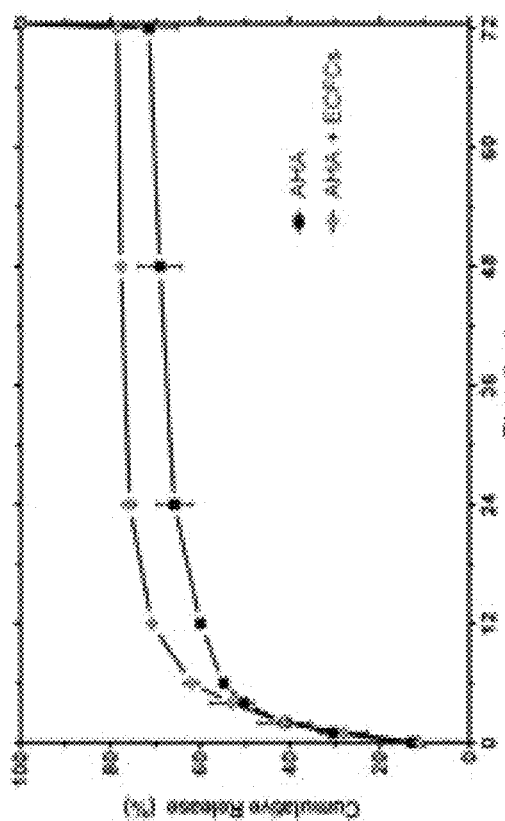
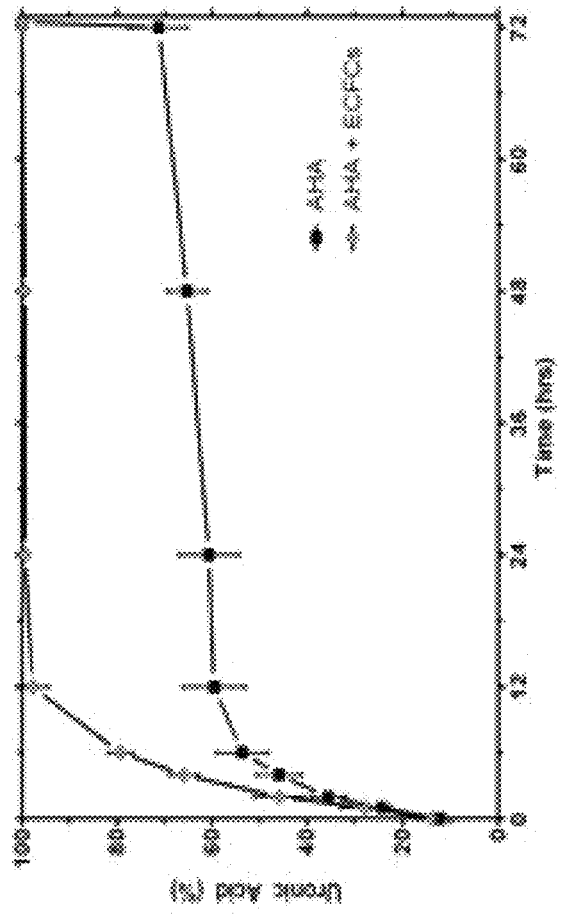
Fig. 15E
Fig. 15F

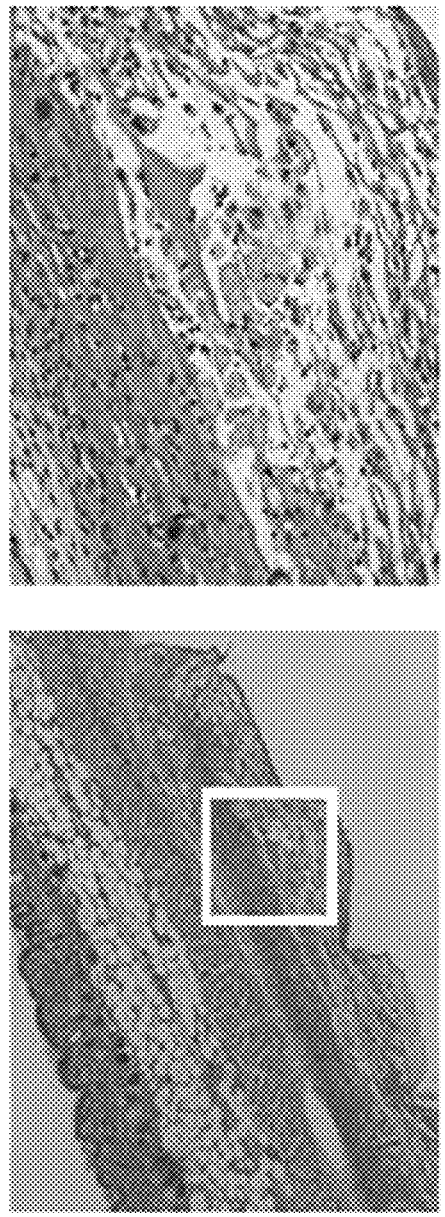
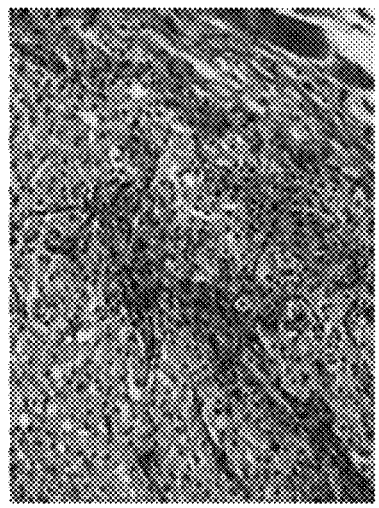
Fig. 17A
Fig. 17B
H&E
H&E

CD31

Mouse
α-SMA

HYDROGEL-BASED VASCULAR LINEAGE CELL GROWTH MEDIA AND USES THEREOF

CROSS-REFERENCE TO RELATED APPLICATION

This application is a continuation of U.S. patent application Ser. No. 13/508,821, filed, May 9, 2012, published Sep. 6, 2012 as US 2012/0225814 and issued on Dec. 2, 2014 as U.S. Pat. No. 8,900,868, which is a National Stage Application under 35 U.S.C. §371 of PCT/US2010/056268, filed Nov. 10, 2010 and published May 19, 2011 as WO 2011/060095, which claims priority to U.S. Provisional Application No. 61/259,821 filed Nov. 10, 2009, the entire contents of all of which are hereby incorporated by reference.

BACKGROUND

1. Field of the Invention

The invention relates to growth media for vascular lineage cells, particularly media using oligosaccharide-based hydrogels as a substrate for vascular lineage cell growth and morphogenesis.

2. Background of the Art

Generating a functional vascular network has the potential to improve treatment for vascular disease and successful organ transplantation. In recent decades, postnatal vasculogenesis has been considered to be an important mechanism for neovascularization via circulating endothelial progenitor cells (EPCs) derived from marrow (Asahara et al., *Science*, vol. 275, pp. 964-967, 1997; Hill et al., *New England J. Med.*, vol. 348, pp. 593-600, 2003). Since their discovery, marrow derived circulating endothelial progenitor cells (EPCs) have been considered to participate in postnatal vasculogenesis (Asahara et al., 1997; Hill et al., 2003; Urbich et al., *Circ. Res.*, vol. 95, pp. 343-353, 2004). Putative EPCs have been proposed as a potential therapeutic tool for treating vascular disease, either through infusion to the site of vascularization (Schatteman et al., *J. Clin. Invest.*, vol. 106, pp. 571-578, 2000; Silva et al., *Proceedings of the National Academy of Sciences*, vol. 105, no. 38, pp. 14347-14352, 2008) or ex vivo expansion for engineering vascularized tissue constructs (Shepherd et al., *FASEB J.*, vol. 20, pp. 1739-1741, 2006; Au et al., *Blood*, vol. 111, pp. 1301-1305, 2008; Melero-Martin et al., *Circulation Research*, vol. 103, no. 2, pp. 194-202, 2008). It has become more evident that endothelial colony-forming cells (ECFCs), a subtype of EPCs recently indentified from circulating adult and human umbilical cord blood, expressed characteristics of putative EPCs (Yoder et al., *Blood*, vol. 109, pp. 1801-1809, 2007; Hirschi et al., *Arterioscler. Thromb. Vasc. Biol.*, vol. 28, pp. 1584-1595, 2008; Yoder, M C, *Journal of Thrombosis and Haemostasis*, vol. 7, SUPPL. 1, pp. 49-52, 2009). These ECFCs are characterized by robust proliferative potential in forming secondary and tertiary colony as well as de novo blood vessel formation in vivo (Yoder, M C, *Arterioscler. Thromb. Vasc. Biol.*, vol. 30, no. 6, pp. 1094-1103, 2010; Ingram et al., *Blood*, vol. 105, no. 7, pp. 2783-2786, 2005).

Differentiation, mobilization, and recruitment of EPCs and endothelial cells (ECs) are regulated foremost by vascular endothelial growth factor (VEGF) (Asahara *Circ. Res.*, vol. 85, pp. 221-228, 1999; Li et al., *FASEB J.*, vol. 20, pp. 1495, 1497, 2006). Administration of VEGF into the site of ischemia has been reported to induce ECs mobilization and restore blood flow (Kaya et al., *J. Cereb. Blood. Flow. Metab.*, vol. 25, pp. 1111-1118, 2005; Sun et al., *J. Clin. Invest.*, vol. 111, pp. 1843-1851, 2003). The extracellular matrix (ECM) provides critical support for ECs; their adhesion to the ECM is required for their proliferation, migration, morphogenesis, and survival—as well as, ultimately, for the stabilization of blood vessels (Davis et al., *Circ. Res.*, vol. 97, pp. 1093-1107, 2005),—through both biochemical and mechanical functions (Deroanne et al., *Cardiovasc. Res.*, vol. 49, pp. 647-658, 2001; Sieminski et al., *Cell Biochem. Biophys.*, vol. 49, pp. 73-83, 2007); Mammoto et al., *Nature*, vol. 457, pp. 1103-1108 2009). Matrix elasticity has been reported to induce stem cell differentiation and morphological changes (McBeath et al., *Dev. Cell.*, vol. 6, pp. 483-495, 2004; Engler et al., *Cell*, vol. 126, pp. 677-689, 2006). Changes in physical interactions between cell surface integrins and the ECM, due to alterations in ECM elasticity, regulate cell shape and cytoskeletal structure (Ingber et al., *J. Cell Biol.*, vol. 109, pp. 317-330, 1989; Matthews et al., *J. Cell Sci.*, vol. 119, pp. 508-518, 2006; Chen et al., *Science* vol. 276, pp. 1425-1428, 1997). Mechanical forces exerted by ECs on the matrix stimulate capillary growth in vivo (Moore et al., *Dev. Dyn.*, vol. 232, pp. 268-281, 2005) and formation of capillary-like structures (CLSs) in vitro (Davis et al., *Exp. Cell Res.*, vol. 216, pp. 113-123, 1995; Ingber et al., *Cell*, vol. 58, pp. 803-805, 1989). Recently, matrix elasticity has been reported to modulate the expression of VEGF receptor 2 (VEGFR2) (Mammoto et al., *Nature*, vol. 457, pp. 1103-1108, 2009), and biomechanical forces alone were sufficient to mediate vascular growth in vivo independent of endothelial sprouting (Kilarski et al., *Nat. Med.*, vol. 15, pp. 657-664, 2009).

Tube morphogenesis is essential for the development of a functional circulatory system [24,25]. Longitudinal vacuoles that appeared to be extruded and connected from one cell to the next were first described by Folkman and Haudenschild (Folkman et al., *Nature*, vol. 288, pp. 551-556, 1980). These observations were confirmed and extended by later studies showing that intracellular vacuoles arise from events downstream of integrin-ECM signaling interactions, where lumen formation is mediated through the activation of the Rho GTPase Cdc42 (Kamei et al., *Nature*, vol. 442, pp. 453-456, 2006; Bayless et al., *J. Cell Sci.*, vol. 115, pp. 1123-1136, 2002; Davis et al., *Exp. Cell Res.*, vol. 224, pp. 39-51, 1996; Iruela-Arispe et al., *Dev. Cell*, vol. 16, pp. 222-231, 2009). Moreover, at the site of neovascularization, activated membrane type 1-matrix metalloproteinase (MT1-MMP) activates pro-MMPs at the pericellular area, which digest the ECM and allow EC migration and tubulogenesis (Collen et al., *Blood*, vol. 101, pp. 1810-1817, 2003; Galvez et al., *J. Biol. Chem.*, vol. 276, pp. 37491-37500). Such matrix remodeling by MMPs is implicated in various pathological conditions including atherosclerosis, inflammation, and ischemia (Romanic et al., *Stroke*, vol. 29, pp. 1020-1030, 1998; Galis et al., *J. Clin. Invest.*, vol. 94, pp. 2493-2503, 1994).

Vascular regeneration and repair are complex processes, which require EPCs to break down the extracellular matrix (ECM), migrate, differentiate, and undergo tube morphogenesis. In the last decades understanding of the role of ECM in vascular morphogenesis has been widely expanded due to well defined in vitro angiogenesis models. Natural ECM such as matrigel, collagen, and fibrin gels have been widely used to study the molecular mechanisms that regulate endothelial cells (ECs) tubulogenesis (Davis et al., *Birth Defects Research Part C—Embryo Today: Reviews*, vol. 81, no. 4, pp. 270-285 2007; Kniazeva et al., *Am. J. Physiol. Cell Physiol.*, vol. 297, no. 1, pp. C179-187, 2009), as well as to transplant vascular progenitor cells, such as ECFCs (Critser et al., "Collagen matrix physical properties modulate endothelial colony forming cell-derived vessels in vivo." *Microvascular Research*, In Press) and EPCs and mesenchymal stem cells (Au et al., *Blood*, vol. 111, pp. 1302-1305, 2008; Au et al., *Blood*, vol. 111, no. 9, pp. 4551-4558, 2008; Melero-Martin et al., *Circulation Research*, vol. 103, no. 2, pp. 194-202, 2008) to generate vascular networks in vivo. However, the inherent chemical and physical properties of these natural materials have limited their manipulation for vascular tissue engineering.

The ECM contains instructive physical and chemical cues required for a delicate balance between various factors and cells to guide vascular assembly (Davis, G E, *Am J Physiol Heart Circ Physiol*, vol. 299, pp. H245-H247, 2010; Sacharidou et al., *Blood*, vol. 115, no. 25, pp. 5259-5269, 2010; Deroanne et al., *Cardiovasc. Res.*, vol. 49, pp. 647-658, 2001; Sieminski et al., *Cell. Biochem. Biophys.*, vol. 49, pp. 73-83, 2007; Kniazeva et al., *Am. J. Physiol. Cell Physiol.*, vol. 297, no. 1, pp. C179-187, 2009; Mammoto et al., *Nature*, vol. 457, pp. 1103-1108, 2009; Stratman et al., *Blood*, vol. 114, no. 2, pp. 237-47, 2009). Depending on their spatial and temporal distribution throughout the body, each ECM component can have a different role in angiogenesis. HA and fibronectin, which are major components of embryonic ECM, are vital vascular regulators during embryogenesis (Toole, B P, *Semin. Cell. Dev. Biol.*, vol. 12, no. 2, pp. 79-87, 2001; Toole, B P, *Nat Rev Cancer*, vol. 4, no. 7, pp. 528-539, 2004); while, collagen and laminin, which are abundant in adult ECM, are crucial for maintaining vascular homeostasis in adults (Davis et al., *Current Opinion in Hematology*, vol. 15, no. 3, pp. 197-203, 2008). Natural ECM, like collagen, fibrin, and matrigel, has been used both as model to study vascular morphogenesis and as scaffold to deliver vascular construct. However the use of natural ECM hydrogels has been limited due to their inherent physical and chemical properties. Moreover, their clinical usage has been hampered due to problems associated with complex purification processes, pathogen transfer, and immunogenicity.

SUMMARY

Synthetic biomaterials, which are xeno-free and more-clinically relevant for regenerative medicine, have been suggested as an alternative (Lutolf et al., *Proc. Natl. Acad. Sci. U.S.A.*, vol. 100, no. 9, pp. 5413-5418, 2003; Ehrbar et al., *Circ Res*, vol. 94, no. 8, pp. 1124-1132, 2004). Unlike natural ECM, these synthetic biomaterials can potentially be engineered to provide an instructive microenvironment, which could orchestrate the complex stages of vascular morphogenesis (Lutolf et al., *Nature Biotechnology*, vol. 23, no. 1, pp. 47-55, 2005). Although previous studies have used self-assembling peptide (Sieminski et al., *Cell. Biochem. Biophys.*, vol. 49, pp. 73-83, 2007; Sieminski et al., *Journal of Biomedical Materials Research*, vol. 87A, no. 2, pp. 494-504, 2008) and PEG hydrogels (Moon et al., *Biomaterials*, vol. 31, no. 14, pp. 3840-3847, 2010; Leslie-Barbick et al., *Journal of Biomaterials Science, Polymer Edition*, vol. 20, no. 12, pp. 1763-1779, 2009) to generate vascular networks in vitro, very few studies have investigated vascular networks assembly within such synthetic biomaterials (Moon et al., *Biomaterials*, vol. 31, no. 14, pp. 3840-3847, 2010; Sieminski et al., *Exp. Cell. Res.*, vol. 297, pp. 574-584, 2004). The present invention includes synthetic biomaterials for vascular morphogenesis that have not been previously available.

Hydrogels with defined compositions and tunable elasticity are used to promote in vitro tube morphogenesis. These hydrogels serve as substrates of varying stiffness, that can affect the kinetics of EPC tubulogenesis. Viscoelasticity measurements during in situ gelation demonstrate three distinct substrate stiffness profiles: rigid, firm, and yielding that have varying effects on tube morphogenesis. While low levels of VEGF allow EPCs to spread on all substrates, higher levels of VEGF may better initiate tube morphogenesis and activate MMPs, whose expression declines with the decrease of matrix stiffness. Increased tube morphogenesis—including CLS progression, vesicle formation, expansion (in both size and number) and fusion to lumens—is better promoted with decreased substrate rigidity. RNA interference (RNAi) studies further show that MT1-MMP and Cdc42 further promote tube morphogenesis from EPCs.

Synthetic acrylated HA (AHA) hydrogels are example substrates to control vascular morphogenesis of ECFCs. Adhesion and cleavability promoters help efficiently form vascular networks. This can improve kinetics and ECFC material interactions during various stages of morphogenesis, which involve vacuoles and lumen formation; branching and sprouting; and network formation and growth. Development and use of hydrogels also requires consideration of the molecular mechanism that regulates ECFCs vascular assembly within the hydrogel. Following transplantation, human vascular networks formed within AHA hydrogels according to the invention anastomize with the host circulation and establish blood flow in the hydrogels.

Embodiments include an vascular lineage cell growth medium including a hydrogel with a stiffness that allows formation of capillary-like structures (CLSs) with extended vacuoles and open lumens from vascular lineage cells. The hydrogel is a crosslinked mixture of an oligosaccharide and a crosslinking moiety, and is cleavable by an enzyme. The medium further includes a growth factor in an amount sufficient to promote vasculogenesis and tube formation, and sufficient to stimulate MMP production in vascular lineage cells. In some embodiments, the hydrogel, or crosslinked mixture, further includes an additional ingredient selected from the group consisting of gelatin, collagen, fibrin, and laminin.

In some embodiments, the crosslinking moiety is cleavable by the enzyme. In some embodiments the crosslinking moiety is a peptide. And in some embodiments, the enzyme is a matrix metalloproteinase. Examples of matrix metalloproteinases include MMP-1, MMP-2 or MMP-10. In some embodiments, the peptide crosslinking moiety includes the amino acid sequence GCRDGPQGIWGQDRCG (SEQ ID NO: 1).

In some embodiments, the hydrogel, or crosslinked mixture, further includes an adhesion promoter in an amount sufficient to promote vascular lineage cell adhesion to the hydrogel and promote vacuole formation in vascular lineage cells. In some embodiments, the adhesion promoter is bonded to the oligosaccharide.

In some embodiments, the stiffness of the hydrogel has a Young's modulus between about 10 Pa and about 500 Pa. In some embodiments, the hydrogel has a Young's modulus less than about 250 Pa.

In some embodiments, the oligosaccharide is modified with an acryl group. In other embodiments, the oligosaccharide is modified with a thiol group. In some embodiments, oligosaccharide is hyaluronic acid, dextran, alginate, or chitosan. In some embodiments, the oligosaccharide is hyaluronic acid. The oligosaccharide may be acrylated hyaluronic acid.

In some embodiments, the growth factor is VEGF, TNFα, SDF1-α, bFGF, angiopoetin-1, PDGF, TGF-β, PlGF or combinations thereof. In some embodiments, the growth factor is VEGF. In some embodiments, the medium includes more than one growth factor. For instance, the growth factors may be VEGF and at least one additional growth factor.

In some embodiments, the growth medium further includes vascular lineage cells. Vascular lineage cells may be, for example, endothelial cells, endothelial progenitor cells, or endothelial colony forming cells.

The growth medium may be prepared by chemically bonding an adhesion promoter to the oligosaccharide, combining the chemically bonded adhesion promoter and oligosaccharide with at least one growth factor, adding an enzymatically cleavable crosslinking peptide moiety, and curing the combination to form a hydrogel where the oligosaccharide is hyaluronic acid that is from about 20 to about 90% acrylate modified and is present in an amount of about 1 wt % to about 4 wt %. The adhesion promoter is present at a concentration of from about 0.1 mM to about 20 mM. The adhesion promoter may be, for example, an RGD sequence containing peptide. The enzymatically cleavable crosslinking peptide is present at a concentration between about 1 mM to about 8 mM. The growth factor is present at a concentration of from about 25 ng/ml to about 200 ng/ml.

Embodiments include methods of inducing vascularization by culturing vascular lineage cells in a medium comprising a hydrogel and a growth factor, where the hydrogel has a Young's modulus between about 10 Pa to about 500 Pa and the hydrogel comprises a crosslinked mixture of an oligosaccharide and a crosslinking moiety. The vascular lineage cells may undergo vascularization within the hydrogel or on the surface of the hydrogel.

In some embodiments, the hydrogel is enzymatically cleavable. This means that a chemical bond within the hydrogel may be cleaved by one or more enzymes. In some embodiments, the hydrogel may be cleaved by a matrix metalloproteinace (MMP). Examples of matrix metalloproteinases include MMP-1, MMP-2, and MMP-10.

In some embodiments, the oligosaccharide is acrylated hyaluronic acid.

In some embodiments of the method, the hydrogel further includes and adhesion promoter.

In some embodiments of the method, the medium is prepared by chemically bonding an adhesion promoter to the oligosaccharide, combining the chemically bonded adhesion promoter and oligosaccharide with at least one growth factor, adding an enzymatically cleavable crosslinking peptide moiety, and curing the combination to form a hydrogel. The oligosaccharide is hyaluronic acid that is from about 20 to about 90% acrylate modified and is present in an amount of about 1 wt % to about 4 wt %. The adhesion promoter is present at a concentration of from about 0.1 mM to about 20 mM and may be an RGD sequence containing peptide. The enzymatically cleavable peptide crosslinking moiety is present at a concentration of from about 1 mM to about 8 mM. The growth factor is present at a concentration of from about 25 ng/ml to about 200 ng/ml.

Embodiments include methods of preparing a vascular network by chemically bonding an adhesion promoter to an oligosaccharide and combining the chemically bonded adhesion promoter/oligosaccharide with at least one growth factor and vascular lineage cells. A crosslinking moiety capable of forming a hydrogel with the oligosaccharide is added to the combination, followed by curing the combination to form a hydrogel. Vascular lineage cells may be added before, during or after curing. The vascular lineage cells are incubated to form a vascular network.

The oligosaccharide may be, for example, hyaluronic acid, dextran, alginate, or chitosan. In some embodiments, the oligosaccharide is hyaluronic acid or acrylated hyaluronic acid.

In some embodiments, the crosslinking moiety is cleavable by a matrix metalloproteinase. This means that a chemical bond within the crosslinking moiety may be cleaved by at least one matrix metalloproteinase enzyme. Examples of matrix metalloproteinases include, for example, MMP-1, MMP-2 or MMP-10. In some embodiments, the crosslinking moiety is a peptide that includes the sequence the sequence GCRDGPQGIWGQDRCG (SEQ ID NO: 1).

In some embodiments, the adhesion promoter is a peptide that includes an RGD sequence and a reactive functional group that is capable of bonding the adhesion promoter to the oligosaccharide.

The growth factor may be, for example, VEGF, TNFα, SDF1-α, bFGF, angiopoetin-1, PDGF, TGF-β, PlGF or combinations thereof.

Embodiments include methods where the oligosaccharide is acrylated hyaluronic acid, and the crosslinking agent is cleavable by a matrix metalloproteinace (MMP). The adhesion promoter is a peptide that includes an RGD sequence and a reactive functional group that is capable of bonding the adhesion promoter to the acrylated hyaluronic acid. In some embodiments of the method the oligosaccharide is hyaluronic acid that is from about 20% to about 90% acrylate modified and is present in an amount of about 1 wt % to about 4 wt %. The adhesion promoter is present at a concentration of from about 0.1 mM to about 20 mM. The crosslinking moiety is an enzymatically cleavable peptide and is present at a concentration of from about 1 mM to about 8 mM. The growth factor is present at a concentration of from about 25 ng/ml to about 200 ng/ml; and the epithelial cell density is from about 2 million cells/mL to about 10 million cells/mL.

In some embodiments, the hydrogel has a Young's modulus between about 10 Pa and about 500 Pa. In some embodiments, the hydrogel has a Young's modulus less than about 250 Pa.

Embodiments include methods of growing blood vessels in vitro by incubating vascular lineage cells in a medium as described herein.

Embodiments include methods of promoting vascular growth in a subject by contacting the subject with a medium or hydrogel containing vascular lineage cells, as described herein. The vascular lineage cells may be partly or wholly vascularized.

DESCRIPTION OF THE DRAWINGS

(FIG. 1A). Microrheology measurements of HA:gelatin in a 1:1 volume ratio with 1%, 0.4%, and 0.1% (w/v) of PEGDA crosslinker over 24 hours of gelation show three distinct profiles of hydrogel mechanics: rigid, firm and yielding. Values shown are means±SD for Young's modulus (E) over 24 hours during the in situ gelation (see FIG. 7 for elastic modulus (G') data). (FIG. 1B) After 12 hours, the values of Young's modulus (stiffness) were: 650±180 Pa for rigid hydrogel, 75±40 Pa for firm hydrogel, and 10±2 Pa for yielding hydrogel. (FIG. 1C) After an additional 12-hour gelation period, a slight increase in stiffness was observed in all three hydrogels with values of: 780±240 Pa, 85±40 Pa, and 15±3 Pa, respectively.

FIGS. 2A-2G: High VEGF concentrations were required for CLS formation from CB-EPC. (FIG. 2A) EPCs were seeded on rigid, firm, and yielding substrates for 12 hours supplemented with 1 ng/ml (low) VEGF (upper panel) and formed CLSs when supplemented with 50 ng/ml (high) VEGF (lower panel), as demonstrated by fluorescence microscopy of F-actin (green) and nuclei (blue). Real Time RT-PCR revealed a significant increased expression of (FIG. 2B) MT1-MMP, (FIG. 2C) MMP-1, and (FIG. 2D) MMP-2 in response to 50 ng/ml VEGF (high) concentration for EPCs cultured on the rigid, firm, and yielding. As the matrix substrate is reduced, EPCs cultured in media supplemented with 50 ng/ml (high) VEGF showed a decrease in expression of (FIG. 2E) MT1-MMP, (FIG. 2F) MMP-1, and (FIG. 2G) MMP-2 which fitted a linear trend with R2 values 0.80, 0.61, and 0.94, respectively. Significance levels were set at: *p<0.05 and **p<0.01. Scale bar is 100 nm.

FIGS. 3A-3E: Substrate mechanics affects CLS phenotype. Metamorph analysis of CLSs revealed a significant increase of mean tube length (FIG. 3A) and mean tube area (FIG. 3B) as substrate stiffness decreased. (3C) Thickened CLSs formed on yielding substrates. Confocal analysis of nuclei (blue), VE-Cad (red), and lectin (green) further revealed (FIG. 3D) branching and (FIG. 3E) hollowing in tubular structures formed on the yielding substrate. Significance levels were set at:*p<0.05, p<0.01, and *p<0.001. Scale bars are 20 nm.

FIGS. 4A-4F: Substrate mechanics regulates vacuole and lumen formation. TEM analyses of CLSs formed after 6 hours showed vacuoles (V) forming on all substrates (S), while EPCs formed two to three layers on rigid substrate (FIG. 4A), extended on firm substrate (FIG. 4B), and formed an elongated single layer on yielding substrates (FIG. 4C). After 12 hours, EPCs grew longer on all substrates and contained many vacuoles (V) on rigid (FIG. 4D) substrate (5), enlarged vacuoles with occasionally noted lumens (L) on firm (FIG. 4E) substrate, and open lumens (L) in complex, lengthened cellular structures on yielding (FIG. 4F) substrates. Cell nucleus is indicated in N. Scale bars are 10 µm in A and 2 µm in B.

FIGS. 6A-6C: Model for mechanics and VEGF co-regulation of tube morphogenesis (cellular and molecular level). VEGF initiates angiogenesis, with EPC assembly into a chain, by inducing MMP activation (FIG. 6A), which further allows EPCs to elongate on substrate within 2-6 hours (FIG. 6B). Substrate mechanics activates Cdc42 (FIG. 6A), resulting in intracellular vacuole formation (FIG. 6B), extension, and fusion to lumens after 12 hours (FIGS. 6B and 6C).

FIGS. 9A-9E: RNAi for MT1-MMP and Cdc42. Real-time RT-PCR analysis of siRNA transfected CB-EPCs shows significant suppression of MT1-MMP (FIG. 9A) or Cdc42 (FIG. 9B) compared to controls (Luciferase-transfected EPCs). Significance levels were set at *p<0.05, and ***p<0.001, respectively. Western blot analysis shows suppression of MT1-MMP (FIG. 9C) or Cdc42 (FIG. 9D) at protein level compared to Luciferase control. (FIG. 9E) Light microscope images of CB-EPCs transfected with Luciferase, MT1-MMP, or Cdc42 seeded on rigid, firm, and yielding substrates for 12 hours. Scale bar is 100 µm.

FIGS. 10A-10C: AHA-hydrogels: study strategy and material characterization. Schematic of study strategy (FIG. 10A); NMR graph (FIG. 10B) demonstrate % acrylate modification of AHA hydrogels. Polymerized AHA hydrogel (3 wt %) in a disc shape (FIG. 10C) as used in this study.

FIG. 12B); vacuole vital stain FM 4-64 (FIG. 12C, cyan; nuclei in blue) of encapsulated cells and higher magnification of a vacuolated cell ((indicated by arrowheads; insert); and TEM high resolution representative image (FIG. 12D) of a single rounded encapsulated cell. Scale bars are 100 µm Increased number and size of vacuole and merging into large lumen detected by day 1 of culture, as indicated by: LM imaging (FIG. 12E) and higher magnification showing merging lumen (indicated by the arrows; FIG. 12F); vacuole vital stain FM 4-64 (FIG. 12G, cyan; nuclei in blue) and higher magnification focused on cell containing large vacuole (indicated by the arrowhead; insert). Scale bars are 50 µm; and TEM high resolution representative image of a encapsulated cell with apparent vacuoles (FIG. 12H). N=nucleus, V=vacuoles, L=lumen, H=hydrogels. Scale bar is 20 µm.

FIGS. 13A-13H: ECFC within AHA gels (Day 2). Progression in tubulogenesis through branching and sprouting and hydrogel degradation are observed using: LM imaging of encapsulated cells on day 2 (FIG. 13A) and higher magnification focusing on branching networks (indicated by arrow; FIG. 13B) scale bars are 100 µm; vacuole vital stain FM 4-64 (cyan; nuclei in blue) on day 2 cells show representative images of branching (FIG. 13C) and sprouting cells (FIG. 13D). Scale bars are 50 µm; and TEM high resolution representative images of: a cell with degraded surroundings (FIG. 13E); (ii) elongated cell morphology (FIGS. 13F and 13G); and guiding channels of degraded hydrogel formed between adjacent cells (FIG. 13H, indicated by arrow). N=nucleus, V=vacuoles, L=lumen, H=hydrogels. Scale bar is 20 µm.

FIG. 14E). Scale bars are 50 µm. TEM high resolution imaging demonstrates cross sectioned of matured vascular tube networks with enlarged lumen (FIG. 14F). Scale bar is 20 µm.

FIGS. 15A-15F: Cell and material interaction. Visco elasticity measurements revealed decrease in hydrogels stiffness along the 3 days culture period, reaching 40 Pa in hydrogel encapsulated with ECFCs (FIG. 15A). SEM images of Day 0 (FIG. 15B) show rounded cells in mesh ultrastructure of the AHA hydrogels (i-iii are low to high magnification) and of Day 3 (FIG. 15C) show spreading cells and formation of guiding microchannels (i-iii are low to high magnification). Real time RT-PCR analysis show increased expression of MT-1 MMP, MMP1, MMP2, Hyal 2 and hyal 3 of encapsulated ECFCs along the 3 days culture period (FIG. 15D). AHA degradation is detected by cumulative percentage of released VEGF (FIG. 15E) and by increased uronic acid in the media along the culture period (FIG. 15F).

FIGS. 17A-17D. Functionality of vascular networks. Nude mice: Histological analysis of implanted vascular networks after 1 week (FIG. 17A) and 2 week (FIG. 17B) in vivo. The microvessels were positive for human CD31 (FIG. 17C) and mouse-$\alpha$-SMA (FIG. 17D).

DETAILED DESCRIPTION

Figure 1A:
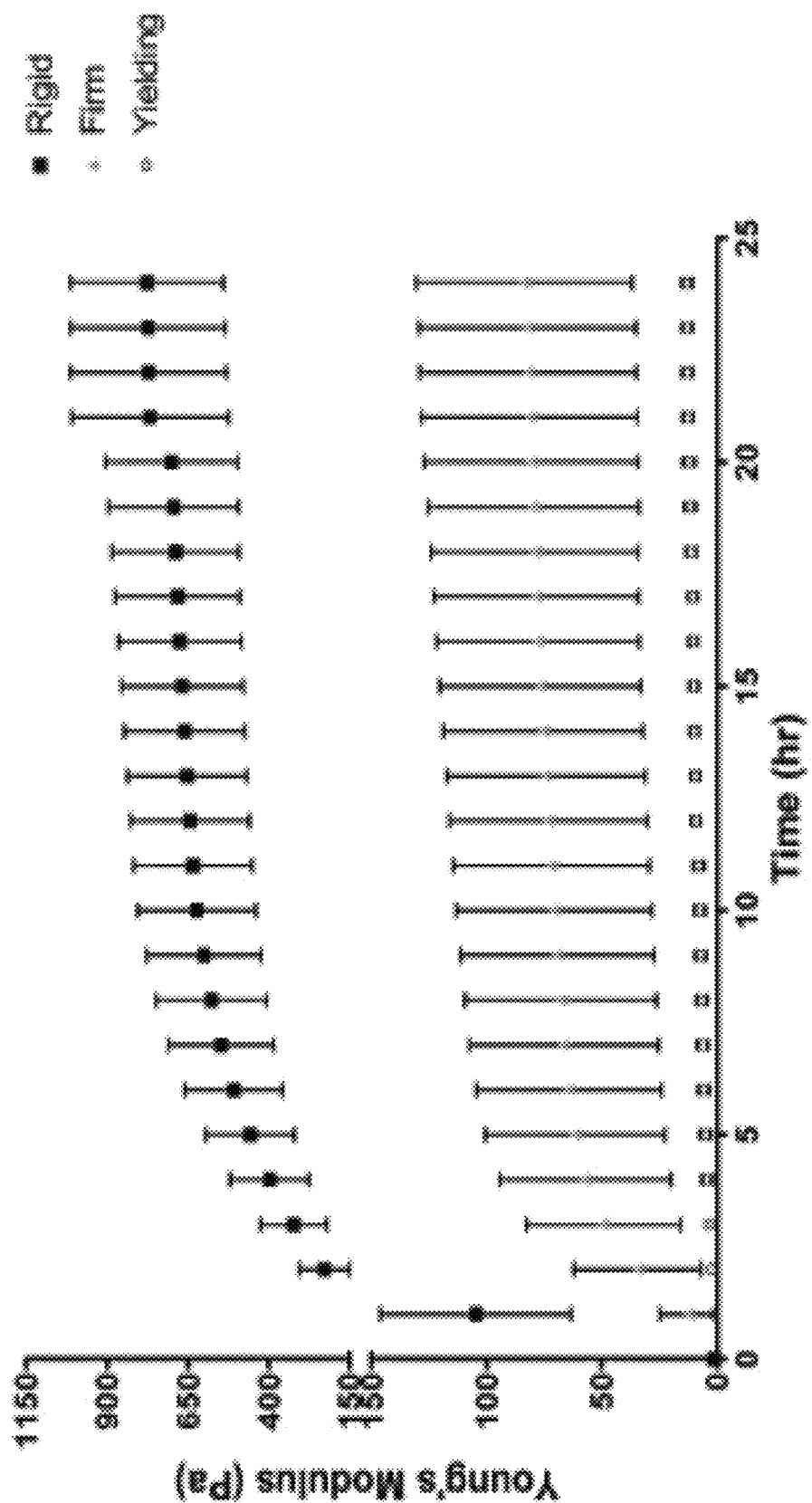
FIGS. 1A-1C: Viscoelasticity of hydrogels.
Figure 1C:
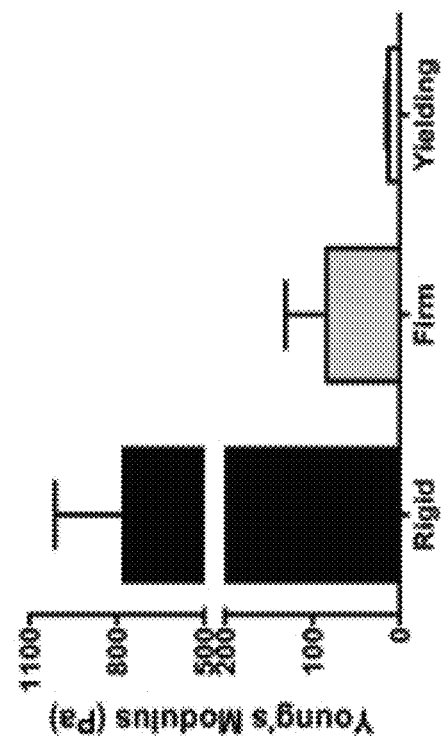
Figure 1B:
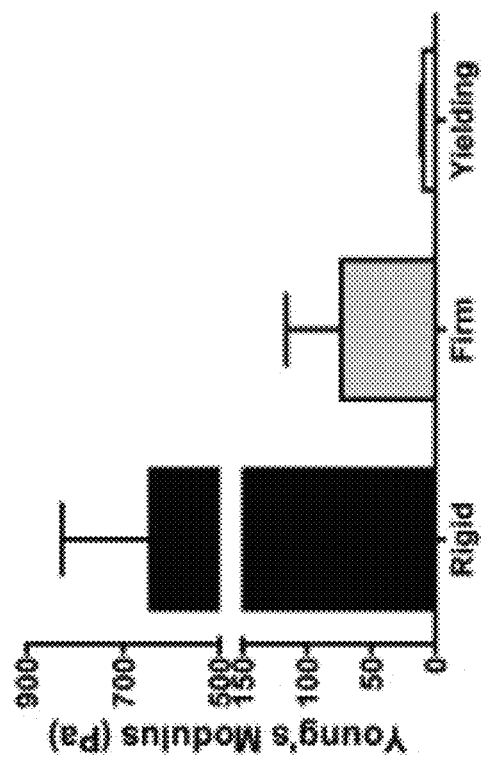

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated. Headings used herein are provided for clarity and organizational purposes only, and are not intended to limit the scope of the invention.

DEFINITIONS

By "modifies" is meant alters. An agent that modifies a cell, substrate, or cellular environment produces a chemical or biochemical alteration in a component (e.g., polypeptide, oligonucleotide, oligosaccharide, or polymer). Modifying a chemical or biochemical entity means that a moiety, for example, a reactive functional group, is formed or added to the entity By "subject" is meant an animal. In some embodiments, a subject may be a mammal, including, but not limited to, a human or non-human mammal, such as a rodent, mouse, bovine, equine, canine, ovine, or feline.

By "therapeutic delivery device" is meant any device that provides for the release of a therapeutic agent.

As used herein, the terms "treat," treating," "treatment," "therapeutic" and the like refer to reducing or ameliorating a disorder and/or symptoms associated therewith. It will be appreciated that, although not precluded, treating a disorder or condition does not require that the disorder, condition or symptoms associated therewith be completely eliminated.

Abbreviations used herein include: Hyaluronic Acid (HA); acrylated hyaluronic acid (AHA); Endothelial Cells (EC); Endothelial Progenitor Cells (EPC); Endothelial Colony Forming Cells (ECFC); Extracellular Matrix (ECM); Matrix Metalloproteinase (MMP); Capillary-like Structures (CLS); Vascular Endothelial Growth Factor (VEGF); Vascular Endothelial Growth Factor Receptor (VEGFR); Stromal-cell Derived Factor (SDF); Tumor Necrosis Factor (TNF).

Growth Medium

Embodiments of the invention include a growth medium for vascular lineage cells. The growth medium includes a hydrogel, which is a crosslinked mixture of an oligosaccharide and a crosslinking moiety. The growth medium further includes a growth factor.

As used herein, a crosslinked mixture of oligosaccharide and crosslinking moiety means that an oligosaccharide molecule is bonded, i.e. by a covalent bond, to two or more crosslinking moieties, and a crosslinking moiety is bonded, i.e. by a covalent bond, to two or more oligosaccharide molecules. The crosslinked compounds form a matrix in the form of a hydrogel.

Oligosaccharides used to form the gels of the invention will have two or more functional groups capable of reacting with functional groups on the crosslinking moiety to form a crosslinked matrix. The functional groups on the oligosaccharide may be the same or different, but should both be able to react with functional groups on the crosslinking moiety.

In some embodiments, the reactive functional groups on the oligosaccharide are all of the same type. In some embodiments, the reactive functional group on the oligosaccharide are acryl groups. In some embodiments, the reactive functional group on the oligosaccharide are thiol groups.

In some embodiments, the reactive functional groups on the crosslinking moiety are all of the same type. In some embodiments, the reactive functional groups on the crosslinking moiety are acryl groups. In some embodiments, the reactive functional group on the crosslinking moiety are thiol groups.

Generally, the reactive functional group on the oligosaccharide and crosslinking moiety will not be the same type, because they must be able to react with each other to form the crosslinked mixture. In other words, if the reactive functional group on the oligosaccharide is an acryl group, the reactive functional group on the crosslinking moiety may be, for example, a thiol group. Likewise, if the reactive functional group on the oligosaccharide is a thiol group, the reactive functional group on the crosslinking moiety may be, for example, an acryl group. The thiol group may react with the acryl group to form a thioether, via a Michael-type addition reaction. Examples of complementary functional groups that may be placed on the oligosaccharide or crosslinking moiety include: thiol and acrylate, thiol and maleimide, amine and aldehyde, amine and succinic anhydride, among others. Other suitable complementary functional groups will be apparent to one of ordinary skill in the art.

In some embodiments, an additional ingredient is included in the crosslinked mixture. In other words, another component that is bonded to two or more crosslinking moieties, or two or more oligosaccharide moieties is included in the hydrogel. The additional ingredient can be, for example, a different oligosaccharide, a peptide, an oligonucleotide, or a polymer, such as a polyacrylamide, polyester, or polyethylene glycol. As is apparent, the additional ingredient will have a reactive functional group that reacts with either the oligosaccharide or the crosslinking moiety, or both (i.e. if the additional ingredient has two different functional groups). In some embodiments, the additional ingredient has a reactive functional group of a single type, for example, thiol or acrylate. Examples of additional ingredients include, for example, gelatin, collagen, fibrin and laminin. In some embodiments, the additional ingredient is gelatin.

The medium having the hydrogel described above may include additional components. In general, the medium will be prepared in water, or buffer. Examples of suitable buffers include phosphate buffered saline (PBS) and triethanolamine-buffered saline (TEOS). Other suitable buffers will be apparent to one of ordinary skill.

Other ingredients and additives commonly used in cell culture media may also be included in the medium. Ingredients typically used in cell culture media, particularly for culture media for vascular lineage cells may be included. For example, additional ingredients may include, heparin, endothelial cell growth supplement (ECGS), or fetal calf serum.

Growth Factor

The medium also includes a growth factor. A growth factor promotes cell growth or propagation, or may induce expression of genes within the cell. Examples of growth factors include: Vascular Endothelial Growth Factor (VEGF); Stromal-cell Derived Factor (SDF), such as SDF1-α; Tumor Necrosis Factor (TNF), such as TNF-α; Basic Fibroblast Growth Factor (bFGF); Epidermal Growth Factor (EGF); angiopoetin (Ang), such as angiopoetin-1 (Ang-1); Platelet Derived Growth Factor (PDGF); Transforming Growth Factor (TGF), such as TGF-β; and Placental Growth Factor (PlGF). Other growth factors are known, and may be used in the medium. More than one growth factor may be used in combination. In some embodiments, the medium includes VEGF and at least one other growth factor. In some embodiments, the medium includes VEGF, SDF1-α, and TNF-α.

The growth factor is present in the medium at an effective concentration. In general, the effective concentration will be determined experimentally and will be within the level of ordinary skill. If there is more than one growth factor, each growth factor may be present in a different concentration, independently determined. In some embodiments, the concentration of one or more growth factors, or the total concentration of growth factors, may be between about 25 ng/mL and about 200 ng/mL. In other embodiments, the concentration may be between about 35 ng/mL and about 100 ng/mL, or between about 40 ng/mL and about 75 ng/mL. In some embodiments the growth factor is present in a concentration greater than about 25 ng/mL, greater than about 30 ng/mL, greater than about 35 ng/mL, greater than about 40 ng/mL, or greater than about 45 ng/mL. In some embodiments, the growth factor is present in the medium in a concentration less than about 200 ng/mL, less than about 150 ng/mL, less than about 100 ng/mL, or less than about 75 ng/mL. In some embodiments, the growth factor is present in a concentration of about 50 ng/mL.

Oligosaccharide

Oligosaccharides used in the hydrogels include, for example, hyaluronic acid, dextran, alginate or chitosan. Other oligosaccharides will be apparent to one of ordinary skill. In some embodiments, the oligosaccharide is hyaluronic acid.

As discussed previously, the oligosaccharide includes functional groups that reacts with the crosslinking moiety to form the hydrogel. In some embodiments, the oligosaccharide is modified to attach, i.e. by a covalent bond, a suitable functional group. For example, if the reactive functional group is an acryl group, the oligosaccharide may be treated with an acrylating agent, such as, for example, acryloyl chloride, to add acryl groups to the oligosaccharide. Suitable methods for modifying the oligosaccharide to attach a suitable reactive functional group will be apparent to one of ordinary skill in the art.

To form a hydrogel, the oligosaccharide must have at least two reactive groups. When a modified oligosaccharide is used, at least two of the saccharide units of the oligosaccharide are modified to have a reactive functional group. When the oligosaccharide is modified, for example, by an acrylate group, the extent of modification may be varied by varying the ratio between the oligosaccharide and the modifying reagent. In some embodiments, more than about 20% of the saccharide units in the oligosaccharide are modified. In other embodiments, more than about 30%, more than about 40% or more than about 50% of the saccharide units in the oligosaccharide are modified. In some embodiments, less than about 90% of the saccharide units in the oligosaccharide are modified. In other embodiments, less than about 80%, or less than bout 70% of the saccharide units in the oligosaccharide are modified. The extent of modification may be determined, for example, by NMR.

In some embodiments, the oligosaccharide is hyaluronic acid (HA). Hyaluronic acid (HA), or hyaluronan, can regulate the angiogenic process by stimulating cytokine secretion and ECs proliferation (Toole, B P, *Semin. Cell. Dev. Biol.*, vol. 12, no. 2, pp. 79-87, 2001; Toole, B P, *Nat Rev Cancer*, vol. 4, no. 7, pp. 528-539, 2004; Genasetti et al., *Connect. Tissue Res.*, vol. 49, no. 3, pp. 120-123 2008). HA-hydrogels consisting of well-defined synthetic polymer networks not only have a high water content to promote cell viability, but also biophysical and biochemical properties similar to many soft tissues (Burdick et al., *Biomacromolecules*, vol. 6, no. 1, pp. 386-391, 2005; Vanderhooft et al., *Macromolecular Bioscience*, vol. 9, no. 1, pp. 20-28, 2009). HA hydrogels have been utilized to induce vasculogenesis from differentiating human embryonic stem cells (Gerecht et al., *Proc. Natl. Acad. Sci. U.S.A.*, vol. 104, pp. 11298-11303, 2007), and to determine mechanical and ultrastructure properties that support in vitro vascular morphogenesis (Hanjaya-Putra et al., *Journal of Cellular and Molecular Medicine*, vol. 14, no. 10, pp. 2436-2447, 2010). Moreover, HA hydrogels are biocompatible, can be biodegraded by hyaluronidase, and can be designed with a range of mechanical properties (Burdick et al., *Biomacromolecules*, vol. 6, no. 1, pp. 386-391, 2005). Overall, due to its biological relevance, chemical modifiability, and ability to support viable cells, HA hydrogels are is an excellent material in biomimetic environments to control vascular morphogenesis.

In some embodiments, the oligosaccharide is hyaluronic acid that has been modified with an acryl group to form acrylated hyaluronic acid (AHA). In some embodiments, about 20% to about 90% of the saccharide units in the hyaluronic acid are modified with acryl groups. In some embodiments, about 30% to about 80% of the saccharide units in the hyaluronic acid molecule are modified with acryl groups. In some embodiments, about 50% to about 70% of the saccharide units in the hyaluronic acid molecule are modified with acryl groups.

Crosslinking Moiety

The crosslinking moiety reacts with the oligosaccharide to form the hydrogel. As discussed previously, the crosslinking moiety has at least two functional groups that react with functional groups on the oligosaccharide. In some cases, the crosslinking moiety has only two functional groups.

The crosslinking moiety may be a different oligosaccharide, a peptide, an oligonucleotide, or a polymer, such as a polyacrylamide, polyester, or polyethylene glycol, so long as the polymer has at least two reactive functional groups.

In some embodiments, the crosslinking moiety is a polyethylene glycol. Polyethylene glycol can be modified to incorporate two reactive functional groups, one at either end of the polymer. Examples of reactive groups include acryl groups. In some embodiments, the crosslinking agent is polyethylene glycol diacrylate (PEGDA). A crosslinker such as PEGDA is not biodegradable. However, oligosaccharide hydrogels used in this invention may still be broken down to promote vascularization because the oligosaccharide portion may be cleaved. For example, hyaluronidase can cleave saccharide bonds in hyaluronic acid, allowing a hyaluronic acid-based hydrogel to be biodegraded or to promote vascular growth.

In some embodiments, the crosslinking moiety is a peptide. In some embodiments, one or more amide bonds in the peptide may be cleavable by one or more enzymes. In some embodiments, the crosslinking moiety is cleavable by one or more matrix metalloproteinases (MMPs). Examples of matrix metalloproteinases include MMP-1, MMP-2 and MMP-10. In some embodiments, the crosslinking moiety comprises the peptide sequence GCRDGPQGIWGQDRCG (SEQ ID NO: 1), which is cleavable by both MMP-1 and MMP-2. Other examples of peptide sequences that can be cleaved by MMPs include, for example IKVAV, a peptide sequence derived from laminin. In facilitating vascularization, the use of enzyme cleavable crosslinking moieties has the advantage of mimicking the ECM. That is, as vascularization progresses, the hydrogel, like the ECM, is broken-down, for example by cellular enzymes, to allow tube morphogenesis, EPC migration, and other physical and chemical effects.

In general, a higher amount of crosslinking moiety relative to the amount of oligosaccharide produces a stiffer hydrogel. The stiffness of the hydrogel may be modified by adjusting the relative amounts of oligosaccharide and crosslinking moiety used to prepare the hydrogel.

Adhesion Promoter

In some embodiments, the crosslinked mixture further includes an adhesion promoter. The adhesion promoter is a molecule that increases cell adhesion to the hydrogel matrix. The adhesion promoter is usually modified to have one functional group capable of reacting with the oligosaccharide or crosslinking agent. Where the crosslinking agent has only two reactive groups, the adhesion promoter should have a functional group that reacts with the oligosaccharide. For example, if the oligosaccharide has thiol reactive groups, the adhesion promoter may have, for example, an acryl functional group. If the oligosaccharide has acryl function groups, the adhesion promoter may have, for example a thiol reactive group.

In general, higher amounts of adhesion promoter relative to the oligosaccharide will produce a hydrogel with more adhesion molecules on the surface. However, more adhesion molecules on the surface may not necessarily increase the extent of vascular lineage cell adhesion to the hydrogel. The optimal amount of adhesion molecules may be determined experimentally.

In some embodiments, the adhesion promoter is a peptide. Several peptides that bind to cell-surface molecules on epithelial cells are known, and any suitable peptide may be used. In some embodiments the adhesion promoter comprises the tripeptide arginine-glycine-aspartate (RGD), which binds integrin molecules on vascular lineage cells.

In natural ECM, like fibrin gel, RGD containing peptides have been shown to regulate vacuoles and lumen formation, a first step in vascular morphogenesis (Bayless et al., $Am. J. Pathol.$, vol. 156, no. 5, pp. 1673-1683, 2000). Moreover, it has been shown that the quantity and presentation of RGD regulates the formation of capillary networks in vitro (Ingber et al., $J. Cell. Biol.$, vol. 109, pp. 317-330, 1989). Therefore, in designing biomimetic AHA gels, adhesion sites within AHA hydrogels promote vacuole formation which subsequently coalescence into an open lumen in ECFCs. This response is dose dependent.

The adhesion promoter molecule may be modified, if necessary, to incorporate a reactive functional group, such as, for example, a thiol or acryl group, to enable it to react with reactive functional groups on the oligosaccharide or modified oligosaccharide. Any modification may be used, so long as the modification does not interfere with the ability of the adhesion promoter to adhere to vascular lineage cells. In some embodiments, the adhesion promoter is modified to incorporate a thiol. For a peptide adhesion promoter, such as RGD, an additional amino acid having a thiol reactive group, such as cysteine, may be added to the peptide to allow it to react with acryl groups on the oligosaccharide. As used herein, RGD means peptides containing the RGD sequence, and may include additional amino acids.

When RGD is used as an adhesion promoter, additional amino acids may be included, so long as one amino acid includes a free reactive group, such as a thiol group. An amino acid containing a thiol group, such as cysteine, may provide the free reactive group. For example, the RGD sequence may be incorporated into a longer sequence, such as, for example, GCGYGRGDSPG (SEQ ID NO: 2), having the RGD adhesion promoter, and a cysteine (C) with a free thiol group. Other sequences may be used, so long as the sequence includes the RGD adhesion promoter and an amino acid having a free thiol, such as a cysteine (C).

In some embodiments, the hydrogel used in the medium includes an adhesion promoter. In some embodiments, the adhesion promoter is an RGD peptide. In some embodiments, the hydrogel is prepared with an RGD peptide in a concentration between about 0.1 mM and about 20 mM. In some embodiments, the hydrogel is prepared with an RGD peptide in a concentration between about 2 mM and about 10 mM, or between about 2 mM and 5 nM.

Vascular Lineage Cells

In some embodiments, the medium further includes vascular lineage cells. As used herein, vascular lineage cells include cells which become endothelial cells. For example, vascular lineage cells include: endothelial cells (EC), pericytes, smooth muscle cells and fibroblasts, that can be derivatives of: endothelial progenitor cells (EPC), endothelial colony forming cells (ECFC), pluripotent stem cells, other vascular progenitor cells such as those from peripheral and cord blood progenitors, bone marrow precursor cells, and mesenchymal derivatives, such as mesenchymal stem cells. In some embodiments, the vascular lineage cells are include endothelial cells (EC), endothelial progenitor cells (EPC), endothelial colony forming cells (ECFC), and vascular cells from pluripotent derivatives, vascular progenitor cells, such as those from peripheral and cord blood progenitors, bone marrow derived vascular precursor cells, such as bone marrow endothelial progenitors; and mesenchymal derivatives, such as mesenchymal vascular cells. In some embodiments, the vascular lineage cells are endothelial cells (EC), endothelial progenitor cells (EPC), or endothelial colony forming cells (ECFC).

Endothelial progenitor cells (EPCs) in the circulatory system have been suggested to maintain vascular homeostasis and contribute to adult vascular regeneration and repair. These processes require that EPCs break down the extracellular matrix (ECM), migrate, differentiate, and undergo tube morphogenesis. The ECM plays a critical role by providing biochemical and biophysical cues that regulate cellular behavior. Using a chemically and mechanically tunable hydrogel for tube morphogenesis in vitro, allows vascular endothelial growth factor (VEGF) and substrate mechanics to effectively co-regulate tubulogenesis of EPCs. In some cases, high levels of VEGF may better initiate tube morphogenesis and activate matrix metalloproteinases (MMPs), which enable EPC migration. Under these conditions, the elasticity of the substrate affects the progression of tube morphogenesis. With decreases in substrate stiffness, decreased MMP expression is observed while increased cellular elongation, with intracellular vacuole extension and coalescence to open lumen compartments, takes place. RNAi studies demonstrate that membrane type 1-MMP (MT1-MMP) enables the movement of EPCs on the matrix and that EPCs sense matrix stiffness through signaling cascades leading to the activation of the RhoGTPase Cdc42. Collectively, coupled responses for VEGF stimulation and modulation of substrate stiffness regulate tube morphogenesis of EPCs.

Endothelial colony forming cells (ECFCs) have robust proliferative potential and can form vascular networks in vivo. ECFCs can be recruited from a bone marrow niche to the site of vascularization, where cues from the extracellular matrix (ECM) instigate vascular morphogenesis. Although this process has been elucidated using natural matrix, the present invention provides for vascular morphogenesis by ECFCs in a synthetic matrix, a xeno-free scaffold which provides a more controllable and clinically relevant alternative for regenerative medicine. For example, chemically and mechanically tunable hyaluronic acid (HA) hydrogels serve as three-dimensional (3D) scaffolds for vascular morphogenesis by ECFCs. Several factors considered in conjunction are used to produce a suitable hydrogel medium. First, an adhesion molecule (also referred to herein as an adhesion promoter), for example, RGD, may be included at a concentration to induce efficient vacuoles formation and lumen formation. Integrin blocking studies confirm that vacuole and lumen formation are dose-dependent on adhesion molecule concentration and recognized by ECFCs through integrin α5β1 and αVβ3. Further, integration of an enzyme cleavable crosslinker, for example, an MMP degradable-peptide as crosslinker enables ECFCs to sprout, branch, and form complex vascular networks. Increased expression of Hyal-1, Hyal-2, MMP-1, -2, and MT1-MMP are followed by the decrease in matrix stiffness, suggesting that ECFCs are able to remodel the gels throughout the process of vascular morphogenesis. Further confocal and TEM analysis throughout the vascular morphogenesis process indicate complex vessel networks form with an open lumen compartment. In vivo studies in nude mice indicate that these engineered-vessels are robust and functional. Most of the microvessels at the center of the hydrogels are positive for human CD31 and perfused with blood cells, indicative that the implanted human vascular networks were able to anastomose with the host vasculatures to form functional vessels (vasculogenesis). Some of the microvessels contain both human CD31+ cells and host cells, confirming that the implanted ECFCs participate in the angiogenesis of the host vasculatures as well.

Hydrogel Stiffness and Vasculogenesis

The Young's modulus of the hydrogel is one indication of the stiffness. The stiffness of the hydrogel may affect the growth and/or morphology of the vascular lineage cells, as discussed in greater detail below. In general, the stiffness of the hydrogel can be varied by varying the relative amounts of oligosaccharide and crosslinking agent used to form the hydrogel. In general, a higher relative amount of crosslinker will produce a stiffer hydrogel.

In some embodiments, the Young's modulus of the hydrogel is about 500 Pa or less. In some embodiments, the Young's modulus of the hydrogel is about 300 Pa or less. In some embodiments, the Young's modulus of the hydrogel is about 250 Pa or less. In some embodiments, the Young's modulus of the hydrogel is less than about 150 Pa, less than about 100 Pa, or less than about 80 Pa. In some embodiments, the Young's modulus is greater than about 10 Pa. In some embodiments, the Young's modulus is greater than about 20 Pa, greater than about 30 Pa, greater than about 40 Pa, or greater than about 50 Pa.

Postnatal vasculogenesis has been considered to be an important mechanism for angiogenesis via marrow-derived circulating EPCs (Asahara et al., *Science*, vol. 275, pp. 964-967, 1997). In response to VEGF, EPCs are mobilized to the site of vascularization, which initiates their proliferation and differentiation (Aicher et al., *Hypertension*, vol. 45, pp. 321-325, 2005). After activation, EPCs undergo a complex process that involves migration, digestion of basement membrane, sprouting, tube morphogenesis, and ultimately, blood vessel stabilization (Davis et al., *Circ. Res.*, vol. 97, pp. 1093-1107, 2005; Urbich et al., *Circ. Res.*, vol. 95, pp. 343-353, 2004). The ECM components play a role in these cascades of events, which are also regulated by cytokines, integrins, and proteases. Therefore, changes in ECM mechanics may modulate properties of EPCs. Media according to the present invention mimic the functionality of the various components of the ECM, thus providing for the cascade of events needed for vascularization.

Changes in ECM mechanics lead to changes in growth factor availability, guide developmental and adaptive changes, and affect cellular fate and the lineage commitment of stem cells (McBeath et al., *Dev. Cell.*, vol. 6, pp. 483-495, 2004; Engler et al., *Cell*, vol. 126, pp. 677-689, 2006). Biomechanical tension between ECs and the ECM regulates capillary development (Davis et al., *Circ Res.*, vol. 97, pp. 1093-1107, 2005; Ingber et al., *J. Cell. Biol.*, vol. 109, pp. 317-330, 1989; Davis et al., *Exp. Cell Res.*, vol. 216, pp. 113-123, 1995), in which mechanical forces exerted by the cells onto the surrounding ECM create pathways for migration that drive migratory ability and subsequent CLS formation (Lo et al., *Biophys. J.*, vol. 79, pp. 144-152, 2000; Discher et al., *Science*, vol. 310, pp. 1139-1143, 2005), as well as in vivo vascularization (Kilarski et al., *Nat. Med.*, vol. 15, pp. 657-664, 2009). Media according to the present invention may be adjusted to mimic ECM mechanics to promote migration, CLS formation, and vascularization.

Hydrogels according to the invention are structurally and mechanically similar to the native ECM of many tissues, and provide a superior matrix for promoting cellular responses to mechanical stresses (Engler et al., *Cell*, vol. 126, pp. 677-689, 2006; Discher et al., *Science*, vol. 310, pp. 1139-1143, 2005; Ghosh et al., *Biomaterials*, vol. 28, pp. 671-679, 2007), as well as endothelial tubulogenesis (Sieminski et al., *Cell. Biochem. Biophys.*, vol. 49, pp. 73-83, 2007; Sieminski et al., *Exp. Cell. Res.*, vol. 297, pp. 574-584, 2004). Hydrogel stiffness modulates the ability of ECs to elongate and contract their surroundings; a reduced tension between the ECs and ECM can trigger an intercellular signaling cascade leading to cellular movement and tubulogenesis (Deroanne et al., *Cardiovasc. Res.*, vol. 49, pp. 647-658, 2001; Sieminski et al., *Cell. Biochem. Biophys.*, vol. 49, pp. 73-83, 2007; Sieminski et al., *Exp. Cell. Res.*, vol. 297, pp. 574-584, 2004; Ingber D E, *Circ. Res.*, vol. 91, pp. 877-887, 2002). Mechanical cues from the ECM and signals from growth factor receptors regulate the balance of activity between TFII-I and GATA2, which govern the expression of VEGFR2, which, in turn, instigates angiogenesis (Mammoto et al., *Nature*, vol. 457, 1103-1108, 2009). However, elasticity range and optima previously reported in studies varies depending on the type of hydrogel (e.g., matrigel, collagen, polyacrylamide, or self-assembly peptide), culture system (two- vs. three-dimensional), and assay (in vivo vs. in vitro) used in the study. Hydrogels used in the present invention may be reproducibly adjusted to mimic the native ECM to promote cellular responses to mechanical stresses.

Although in vivo and in vitro studies have shown that lumenal structures and tube formation involve the formation of intracellular vacuoles (Kamei et al., *Nature*, vol. 442, pp. 453-456, 2006; Bayless et al., *J. Cell. Sci.*, vol. 115, pp. 1123-1136, 2002), the molecular mechanisms of these processes have been delineated only recently. Using collagen as a 3D in vitro model of angiogenesis, Davis and colleagues showed that EC lumenization via formation and coalescence of pinocytic intracellular vacuole involves coordinated signaling pathways: localized at cell membranes, MT1-MMP degrades the ECM and creates a physical space to facilitate lumen formation (Chun et al., *J. Cell Biol.*, vol. 167, pp. 757-767, 2004; Saunders et al., *J. Cell Biol.*, vol. 175, pp. 179-191, 2006), while integrin-ECM interactions initiate a cascade of downstream signaling to activate the Rho GTPases Cdc42 and Rac1, which drive the formation of intracellular vacuoles (Bayless et al. *J. Cell Sci.*, vol. 115, pp. 1123-1136, 2002).

Molecular mechanisms are co-regulated by growth factors and ECM elasticity. MT1-MMP, which is present as an active enzyme on the cell surface, acts directly against different ECM proteins and can activate pro-MMPs at the cell surface, which localizes MMP activity to the pericellular area (Van Hinsbergh et al., *Arterioscler. Thromb. Vasc. Biol.*, vol. 26, pp. 716-728, 2006; Haas T L, *Can. J. Physiol. Pharmacol.*, vol. 83, pp. 1-7, 2005). VEGF or other growth factors can directly regulate the production of MT1-MMP, MMP-1 and MMP-2 in EPCs and activity of MT1-MMP is required to initiate tube morphogenesis. As shown in the present invention, suppression of MT1-MMP mitigates CLS formation on firm and yielding substrates while maintaining spreading on rigid substrates. Thus, MT1-MMP suppressed EPCs are no longer able to degrade the surrounding ECM in order to form CLSs. On softer gels, where EPCs produced the least amount of MMPs and have dynamic adhesions (Pelham et al., *Proc. Natl. Acad. Sci. U.S.A.*, vol. 94, pp. 13661-13665, 1997), MT1-MMP suppression prevents them from spreading and causes them to exhibit a rounded morphology; on the rigid substrate, it allows EPCs to spread with a morphology similar to that exhibited when cultured in media with low levels of VEGF. The inventive medium highlights the importance of these molecular mechanisms.

Downstream of integrin signaling, Cdc42 has been shown, using both in vitro and in vivo models, to mediate vascular morphogenesis events (Kamei et al., *Nature*, vol. 442, pp. 453-456, 2006; Bayless et al., *J. Cell. Sci.*, vol. 115, pp. 1123-1136, 2002). As shown in studies relating to the present invention, inhibition of Cdc42 prevented CLS formation on all substrates, regardless of elasticity. However, while the inhibition of Cdc42 does not prevent EPCs spreading on the rigid and firm substrates, they appear round on the yielding substrate. Suppression of Cdc42 prevents EPCs from physically resisting cell traction forces that are needed on the soft gel (Discher et al., *Science*, vol. 310, pp. 1139-1143, 2005; Ingber D E, *Circ. Res.*, vol. 91, pp. 877-887, 2002), which result in rounded cell morphology on the yielding substrate. Furthermore, it was recently suggested that activated Cdc42 augmented MMP-2 and MT1-MMP activity (Ispanovic et al., *Am. J. Physiol. Cell Physiol.*, vol. 295, pp. C600-C610, 2008), which supports that Cdc42 suppressed EPCs are unable to form CLSs on all substrates. The inventive medium further establishes the importance of Cdc42 signalling.

Acrylated Hyaluronic Acid Hydrogels

In some embodiments, the hydrogel is a crosslinked mixture of acrylated hyaluronic acid (HA) as the oligosaccharide, a thiol-terminated RGD integrin binding peptide as the adhesion promoter, and a peptide crosslinking moiety that is enzymatically degradable by both MMP-1 and MMP-2 that includes the sequence GCRDGPQG↓IWGQDRCG (SEQ ID NO: 1), where ↓ denotes the site of cleavage.

In some embodiments, more than about 20% of the saccharide units in the hyaluronic acid are acrylated. In other embodiments, more than about 30%, more than about 40% or more than about 50% of the saccharide units in the hyaluronic acid are acrylated. In some embodiments, less than about 90% of the saccharide units in the hyaluronic acid are acrylated. In other embodiments, less than about 80%, or less than about 70% of the saccharide units in hyaluronic acid are acrylated. The extent of modification may be determined, for example, by NMR.

In some embodiments, the AHA may be about 50% modified (50% of the repeating HA macromer contains acrylate group), and are used to form 3 wt % hydrogels (FIGS. 10B and 10C). Higher acrylate modification and wt % correspond to relatively dense networks and can also be used but do not as effectively support vascular morphogenesis.

Acrylated HA (AHA) hydrogels when used in media according to the present invention provide the dynamic cues required for network assembly of encapsulated ECFCs (FIG. 1A). These hydrogels are formed using sequential crosslinking from acrylated HA by reacting with a thiol-terminated adhesion promoter, such as the RGD integrin-binding peptide (thiol group on RGD react with acrylates along the HA backbone) followed by an addition reaction with a crosslinking moiety, for example, a thiol-terminated peptide crosslinker (thiol groups on each end of peptide react with acrylates along the HA backbone) (Khetan et al., *Soft Matter*, vol. 5, no. 8, pp. 1601-1606, 2009). Example AHA hydrogels include an enzymatically degradable peptide crosslinker that can be cleaved by MMP-1, MMP-2, MMP-10 or others both (Lutolf et al., *Proc. Natl. Acad. Sci. U.S.A.*, vol. 100, no. 9, pp. 5413-5418, 2003; Seliktar et al., *J. Biomed. Mater. Res. A*, vol. 68, no. 4, pp. 704-716, 2004), for example a peptide with the sequence GCRDGPQG↓I-WGQDRCG (SEQ ID NO: 1), where ↓ denotes the cleavage site. An adhesion promoter, such as RGD, which is the sequence within the fibronectin molecule that mediates cell attachment, can also be included.

Methods

Embodiments include methods of inducing vascularization by culturing vascular lineage cells in a medium comprising an oligosaccharide-based hydrogel and a growth factor, where the hydrogel has a Young's modulus between about 10 Pa and about 500 Pa. Any hydrogel discussed herein may be used in the culture medium. Oligosaccharides, adhesion promoters, and crosslinking moieties discussed herein may make up the hydrogel, and growth factors discussed herein may be used in the medium.

In some embodiments, the vascular lineage cells undergo vascularization within the hydrogel or on the surface of the hydrogel.

In some embodiments, the hydrogel is enzymatically cleavable. In other words, chemical bonds within the hydrogel may be cleaved by one or more enzymes. In some embodiments, the hydrogel is cleavable by a matrix metalloproteinase, such as, for example MMP-1, MMP-2, or MMP-10. A cleavable crosslinking moiety, as discussed herein, will produce a hydrogel that is enzymatically cleavable. In some instances, the oligosaccharide portion may be enzymatically cleavable.

In some embodiments, the Young's modulus of the hydrogel is about 500 Pa or less. In some embodiments, the Young's modulus of the hydrogel is about 300 Pa or less. In some embodiments, the Young's modulus of the hydrogel is about 250 Pa or less. In some embodiments, the Young's modulus of the hydrogel is less than about 150 Pa, less than about 100 Pa, or less than about 80 Pa. In some embodiments, the Young's modulus is greater than about 10 Pa. In some embodiments, the Young's modulus is greater than about 20 Pa, greater than about 30 Pa, greater than about 40 Pa, or greater than about 50 Pa.

Embodiments include methods of preparing a vascular network by chemically bonding an adhesion promoter to an oligosaccharide, then combining the chemically bonded adhesion promoter/oligosaccharide with at least one growth factor and epithelial cells. Then an enzymatically cleavable peptide crosslinking moiety is added, and the combination is cured to form a hydrogel. The hydrogel and cells are then incubated to form a vascular network. Oligosaccharides, adhesion promoters, enzymatically cleavable peptide crosslinking moieties, and growth factors discussed herein may be used in the method.

Embodiments include methods of growing blood vessels in vitro by incubating vascular lineage cells with a growth medium described herein.

Embodiments include methods of promoting vascular growth in a subject by contacting the subject with a hydrogel described herein having vascular lineage cells. In this case, the vascular lineage cells may already have begun vascularization by incubating the medium prior to contacting the subject with the hydrogel.

Uses

Hydrogels and methods according to the invention can be used in tissue engineering scaffolds, wound care and for other purposes. Example embodiments of the invention include methods for promoting vascularization in vitro, creating vascular networks in engineered tissues, use as a graft for ischemia, or as a cardiac patch/graft. Other uses include methods of promoting burn and wound healing. Other embodiments include methods of improving grafting, promoting injured tissue regeneration and improving injured tissue functionality.

The generation of functional vascular networks has the potential to improve treatment for vascular diseases and to facilitate successful organ transplantation. Other embodiments of the invention include methods of increasing vascular regeneration comprising administering a composition described above. Methods of increasing vascular regeneration can promote, for example, burn and wound healing. As engineered tissues become available, compositions and methods of the invention can be used to promote vascularization. As shown below, use of the present compositions not only promote vascularization in vitro, but also allow the new vasculature to link with existing vasculature. This can be used to further promote tissue acceptance in the host or improve tissue grafting.

Compositions and hydrogels including vascular lineage cells of the invention may be used, for example, for the treatment of wounds or burns by applying the composition to the surface of the body. The hydrogel may be added to the body after some vascularization of the vascular lineage cells has taken place. The composition may also be administered subcutaneously (i.e. below the skin) to increase vascular growth or regeneration. In other cases, the composition may be implanted at a specific location in the body, inducing vascular growth for the treatment of, for example, ischemias.

The hydrogels described herein may be administered by any available route for administering hydrogels to a subject. The compositions may be formulated with at least one pharmaceutically acceptable carrier depending on the method of administration. The compositions may be administered, for example, parenterally, subcutaneously or topically, depending on the material to be delivered to the subject and the targeted tissue.

In some embodiments, the composition is crosslinked prior to administration. The crosslinked composition may be formed in a particular shape, for example as ovoid, sphere, disc, sheet or other structure. Crosslinked compositions may be administered internally or externally.

Preparation

The oligosaccharides or modified oligosaccharides described above may be prepared according to methods known in the art. Hydrogels may be prepared by combining oligosaccharides having two or more reactive functional groups with a crosslinking agent having two or more reactive functional groups. The ingredients are allowed to react until a crosslinked gel is formed.

If desired, an additional ingredient, having at least two reactive functional groups may be included in the reaction mixture, for example, before gel formation to modify the properties of the hydrogel. The proportions of the ingredients may be varied to further modify the properties of the hydrogel.

If desired, an adhesion promoter having a reactive functional group may be reacted with the oligosaccharide prior to reaction with the crosslinking agent, or may be included in the reaction with the crosslinking moiety to form a hydrogel having an adhesion promoter incorporated into the crosslinked matrix.

The relative concentration of each component: oligosaccharide; crosslinker; optional additional ingredient; or adhesion promoter may be varied to produce hydrogels with different properties such as the stiffness of the hydrogel. In some embodiments, the hydrogel is formed from an oligosaccharide at a concentration of about 1 wt % to about 4 wt %. In some embodiments, the hydrogel is formed from an oligosaccharide at a concentration between about 2 wt % and about 3 wt %.

In general, the number of reactive functional groups on the oligosaccharide or modified oligosaccharide will affect the amounts of the crosslinker, optional additional ingredient, or optional adhesion promoter. For instance, if the oligosaccharide has more reactive functional groups, or the oligosaccharide is modified to a greater extent, then higher concentrations of other components may be used. In general, the amount of crosslinker, and optional adhesion promoter should not exceed the amount of reactive functional groups on the oligosaccharide.

In some embodiments, the hydrogel is formed with a crosslinker concentration between about 1 mM and about 8 mM. In some embodiments, the hydrogel is formed with a crosslinker concentration between about 1 mM and about 7 mM. In some embodiments, the hydrogel is formed with a crosslinker concentration between about 2 mM and about 5 mM.

In some embodiments, the hydrogel is formed with an adhesion promoter concentration between about 0.1 mM and about 20 mM. In some embodiments, the hydrogel is formed with an adhesion promoter in a concentration between about 1 mM and about 15 mM. In some embodiments, the hydrogel if formed with an adhesion promoter in a concentration between about 2 mM and about 10 mM.

In general, higher amounts of crosslinker relative to the oligosaccharide will produce a more stiff hydrogel. In general, higher amounts of adhesion promoter relative to the oligosaccharide will produce a hydrogel with more adhesion molecules on the surface.

Once formed, the hydrogel is combined with a growth factor to prepare the medium. Other ingredients may be included, as needed, to form an effective vascular lineage cell growth medium. Alternatively, the growth factor can be added prior to the formation of the hydrogel, i.e. before addition of the crosslinker. In this way, growth factors may be encapsulated within the hydrogel.

Once prepared, the medium is used to grow vascular lineage cells, including endothelial progenitor cells, or endothelial colony forming cells. Cells may be grown at a density greater than about 2 million cells/mL, greater than about 3 million cells/mL, greater than about 4 million cells/mL, or greater than about 5 million cells/mL. Cells may be grown at a density less than about 10 million cells/mL, less than about 9 million cells/mL, or less than about 8 million cells/mL.

In some embodiments, the adhesion promoter is chemically bonded to the oligosaccharide prior to hydrogel formation. Reactive groups on the adhesion promoter react with reactive functional groups on the oligosaccharide to produce a chemically bonded adhesion promoter/oligosaccharide. The adhesion promoter and oligosaccharide may be combined in quantities such that the adhesion promoter reacts with at least about 1%, at least about 2%, at least about 3%, at least about 5%, at least about 7%, or at least about 10% of the reactive functional groups on the oligosaccharide. The adhesion promoter and oligosaccharide may be combined in quantities such that the adhesion promoter reacts with less than about 30%, less than about 25%, less than about 20% or less than about 15% of the reactive functional groups on the oligosaccharide.

Once formed, the chemically bonded adhesion promoter/oligosaccharide may be combined with growth factors, followed by adding the crosslinking moiety. After the crosslinking moiety is added, the mixture forms the hydrogel.

In some embodiments, vascular lineage cells are included with the mixture of chemically bonded adhesion promoter/oligosaccharide and growth factors, before the crosslinking moiety is added. The vascular lineage cells may be added before or after the growth factors are added. In this way a culture medium where the vascular lineage cells are present within the hydrogel may be prepared. In this medium, the vascular lineage cells undergo vascularization within the hydrogel, not just on the surface.

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Terms listed in single tense also include multiple unless the context indicates otherwise.

As described herein, all embodiments or subcombinations may be used in combination with all other embodiments or subcombinations, unless mutually exclusive.

The examples disclosed below are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

Methods for preparing, characterizing and using the compounds of this invention are illustrated in the following Examples. Starting materials are made according to procedures known in the art or as illustrated herein. The following examples are provided so that the invention might be more fully understood. These examples are illustrative only and should not be construed as limiting the invention in any way.

EXAMPLES

Hyaluronic acid (HA)-gelatin hydrogels were used to assess how medium stiffness affects EPC tube morphogenesis. One advantage of HA-gelatin hydrogels is that the chemistry of the network can be controlled via reaction conditions and kept uniform between the various batches, which is difficult or impossible to achieve with naturally derived matrices such as matrigel and collagen. Furthermore, while enzymatic crosslinking of natural gels such as matrigel and collagen allows studies of increased stiffness, chemically modified HA-gelatin hydrogels enables control over crosslink density, and the ability to assess cellular responses over a wide range of tunable mechanical stimuli. Previous studies demonstrated that HA-gelatin hydrogels support in vivo angiogenesis (Shu et al., *J. Biomed. Mater. Res. A*, vol. 79, pp. 902-912, 2006) and embryonic vasculogenesis (Gerecht et al., *Proc. Natl. Acad. Sci. U.S.A.*, vol. 104, pp. 11298-11303, 2007). Thiol-modified HA-gelatin hydrogels enables EPC attachment. These hydrogels can be mechanically tuned using the PEGDA crosslinker while preserving uniform presentation of cell adhesion molecules (Vanderhooft et al., *Macromol. Biosci.*, vol. 9, pp. 20-28, 2009).

Materials and Methods

Human EPCs.

Human umbilical cord EPCs isolated from outgrowth clones, provided by Dr. Yoder, Indiana University School of Medicine, were expanded and used for experiments between passages 3 and 10. EPCs were isolated from seven healthy newborns (three females and four males; gestational age range, 38-40 weeks), pooled, expanded, and characterized according to previously established protocol (Ingram et al., *Blood*, vol. 104, pp. 2752-2760, 2004; Yoder et al., *Blood*, vol. 109, pp. 1801-1809, 2007; Mead et al., *Curr. Protoc. Stem Cell Biol.*, vol. 2, p. 2C.1, 2008; Prater et al., *Leukemia*, vol. 21, pp. 1141-1149, 2007; Timmermans et al., *J. Cell. Mol. Med.*, vol. 13, pp. 87-102, 2009). Briefly, EPCs were expanded in flasks coated with type I collagen (Roche Diagnostics, Basel, Switzerland), in endothelial growth medium (EGM; PromoCell Heidelberg, Germany) supplemented with 1 ng/ml $VEGF_{165}$ (Pierce, Rockford, Ill.), and incubated in a humidified incubator at 37° C. in an atmosphere containing 5% $CO_2$. EPCs were passaged every three to four days with 0.05% trypsin (Invitrogen, Carlsbad, Calif.) and characterized for the positive expression of cell-surface antigens CD31, CD141, CD105, CD144, vWF and Flk-1, and the negative expression of hematopoietic-cell surface antigens CD45 and CD14. Single cell colony forming assays were used to characterize their robust proliferative potential, secondary and tertiary colony formation upon replating.

Preparation of PEGDA Crosslinked Hyaluronic Acid (HA)-Gelatin Hydrogels.

HA-gelatin hydrogels (Extracel, Glycosan BioSystems, Inc., Salt Lake City, Utah) were prepared as previously described (Vanderhooft et al., *Macromol. Biosci.*, vol. 9, pp. 20-28, 2009). Briefly, the hydrogels were obtained by mixing 0.4% (w/v) Glycosil solution with 0.4% (w/v) Gelin-S solution in a 1:1 volume ratio with 1%, 0.4%, and 0.1% (w/v) of polyethylene glycol diacrylate (PEGDA) crosslinker (MW 3400) in a 4:1 volume ratio, to obtain rigid, firm, and yielding substrates, respectively. The pregel solution was cast into a 96-well glass bottom plate (MatTek, Ashland, Mass.) for live/dead assay and CLS quantification and a 16-well Lab-Tek chamber slide (NUNC, Rochester, N.Y.) for TEM analysis and confocal images. Post-gelation, all hydrogels were allowed to cure for 12 hours inside a biological safety cabinet to stabilize PEGDA-mediated crosslinking.

Viscoelasticity Measurement.

Oscillatory shear measurements of the elastic modulus (G') were obtained using a constant strain rheometer with steel cone-plate geometry (25 mm in diameter; RFS3, TA Instruments, New Castle, Del.) as previously described (Vanderhooft et al., *Macromol. Biosci.*, vol. 9, pp. 20-28, 2009). Briefly, oscillatory time sweeps were performed on three samples (n=3) for stiff, rigid, and yielding hydrogels to monitor the in situ gelation. The strain was maintained at 20% during the time sweeps by adjusting the stress amplitude at a frequency of 1 Hz. This strain and frequency were chosen because G' was roughly frequency independent within the linear viscoelastic regime. The 24-hour tests occurred in a humidified chamber at a constant temperature (25° C.) in 30 second intervals. The Young's modulus (substrate stiffness) was calculated by $E=2G'(1+v)$. HA-gelatin hydrogels can be assumed to be incompressible (Vanderhooft et al., *Macromol. Biosci.*, vol. 9, pp. 20-28, 2009), such that their Poisson's ratios (v) approach 0.5 and the relationship becomes $E=3G'$ (Mammoto et al., *Nature*, vol. 457, pp. 1103-1108 2009; Boudou et al., *Biorheology*, vol. 43, pp. 721-728, 2006).

In a first stage of identifying suitably stiff hydrogels, different hydrogels with the same HA:gelatin ratio, but with increased PEGDA crosslinker concentration can be prepared to examine the gelation kinetics (FIG. 1A). Within 12 hours of HA-gelatin hydrogel curing, distinct Young's modulus (stiffness) profiles were established for rigid (650 Pa), firm (75 Pa), and yielding (10 Pa) HA-gelatin hydrogels. After an additional 12 hours of gelation, a slight increase in stiffness is observed in all hydrogels (rigid to 780 Pa, firm to 85 Pa, and yielding to 15 Pa). The 24 hour gelation period was sufficient to completely crosslink all available thiol groups on the hydrogels at this HA:gelatin and PEGDA crosslinker composition (Vanderhooft et al., *Macromol. Biosci.*, vol. 9, pp. 20-28, 2009). Indeed, further gelation time did not significantly increase substrate stiffness. Accordingly, HA-gelatin hydrogels cured for 12 hours, and used in the 12 to 24 hour period provide hydrogel mechanics that are fairly constant and can be used to evaluate EPC tube morphogenesis under various conditions.

Angiogenesis Assay.

Cord blood derived endothelial progenitor cells (CB EPCs) were seeded on rigid, firm, and yielding substrates, cured for 12 hours, with densities of 100,000 cells/$cm^2$. Constructs were cultured for 12 hours in EGM (PromoCell GmbH, Germany) supplemented with 1, 10, 25, or 50 ng/ml recombinant human $VEGF_{165}$ (Pierce, Rockford, Ill.). Visualization and image acquisition were performed using an inverted light microscope (Olympus IX50, Center Valley, Pa.) at time intervals of 3, 6, 9, and 12 hours.

Figure 2A:
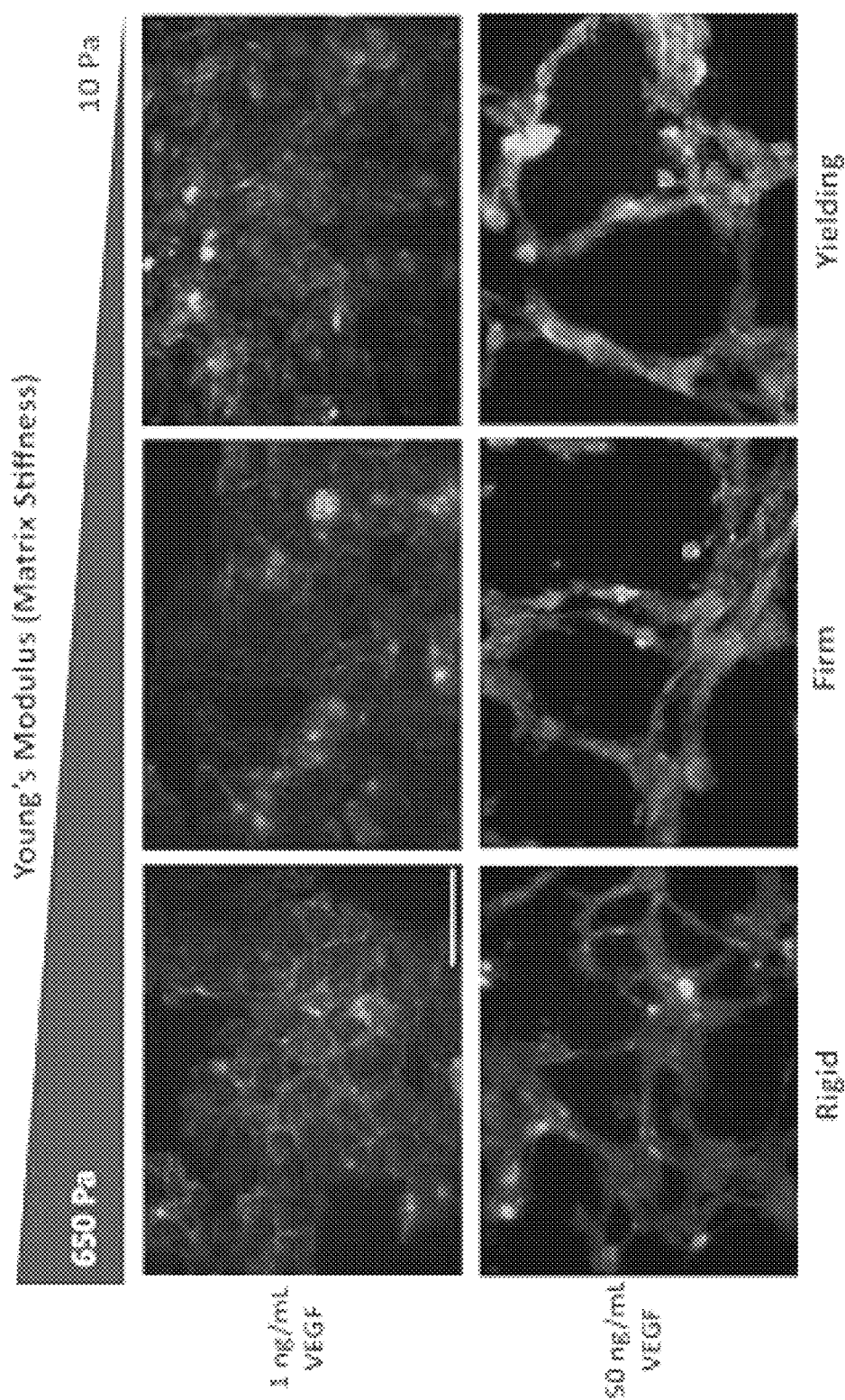

CB EPCs form functional and stable blood vessels in vivo compared to adult peripheral blood EPCs, which formed blood vessels that were unstable and that regressed rapidly (Au et al., *Blood*, vol. 111, pp. 1301-1305, 2008). EPCs have been used to study in vitro capillary tube formation induced by substrate nanotopography (Bettinger et al., *Adv. Mater.*, vol. 20, pp. 99-103, 2008). In vitro tube morphogenesis with lumen compartments was established as a prerequisite to define CB-EPCs (Timmermans et al., *J. Cell. Mol. Med.*, vol. 13, pp. 87-102, 2009; Hirschi et al., *Arterioscler. Thromb. Vasc. Biol.*, vol. 28, pp. 1584-1595, 2008). To evaluate tube morphogenesis in a controllable in vitro system, EPCs can be seeded on HA-gelatin hydrogel substrates cured for 12 hours in media supplemented with either 1 ng/ml (low) or 50 ng/ml (high) VEGF. High concentrations of VEGF (i.e., 50 ng/ml) is known to induce vascular differentiation of embryonic stem cells (Ferreira et al., *Circ. Res.*, vol. 101, pp. 286-294, 2007) and vasculogenesis in HA hydrogels (Gerecht et al., *Proc. Natl. Acad. Sci. U.S.A.*, vol. 104, pp. 11298-11303, 2007). After 12 hours of incubation, no tube formation was observed in any culture supplemented with 1 ng/ml VEGF, while some CLS formed on the rigid and firm substrates, and predominant CLSs, similar to the CLSs observed on matrigel, formed on the yielding substrate supplemented with 50 ng/ml VEGF (FIG. 2A).

It should be noted that intermediate VEGF concentrations (e.g., 10 ng/ml or 25 ng/ml) increased tube morphogenesis on all substrates compared to 1 ng/ml, but with inferior outcomes when compared to high VEGF concentrations. We therefore continued our studies of tube morphogenesis using high concentrations of VEGF.

Quantification of CLSs.

The LIVE/DEAD Viability/Cytotoxicity Kit (Invitrogen, Carlsbad, Calif.) was used to visualize CLSs, following the manufacturer's protocol. Briefly, calcein AM dye was diluted in phenol red-free DMEM (Invitrogen, Carlsbad, Calif.) to obtain a final concentration of 2 µM. The constructs were incubated with the dye solution for 30 minutes. After replacing with fresh phenol red-free DMEM, CLSs were visualized using a fluorescent microscope with a 10× objective lens (Axiovert, Carl Zeiss Inc., Thornwood, N.Y.). We analyzed four image fields per construct from three distinct experiments (n=3) performed in triplicate, using Metamorph software 6.1 (Universal Imaging Co., Downingtown, Pa.) to quantify and compare CLSs formed on each substrate.

Figure 3D:
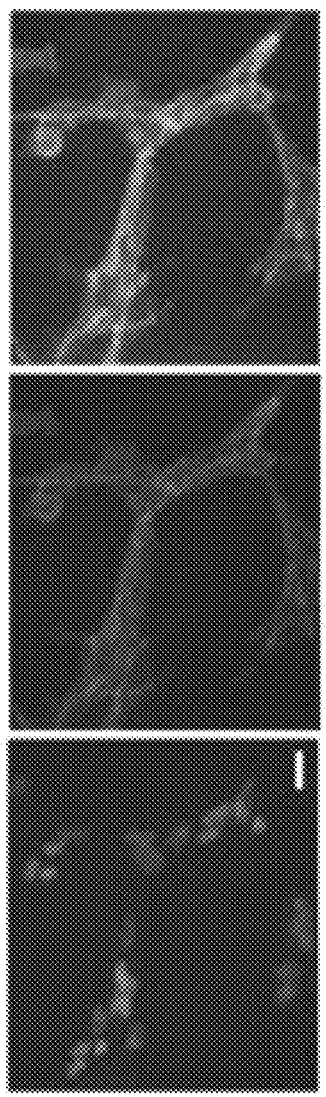
Figure 3E:
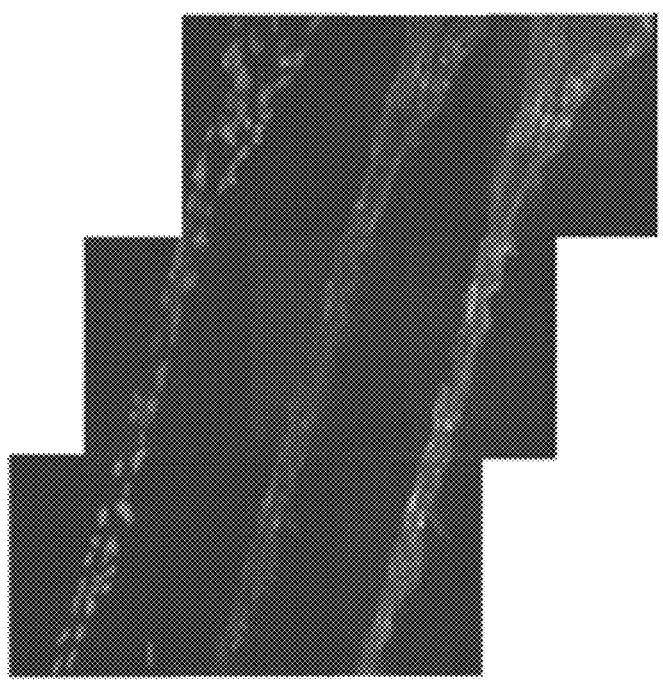
Figure 8:
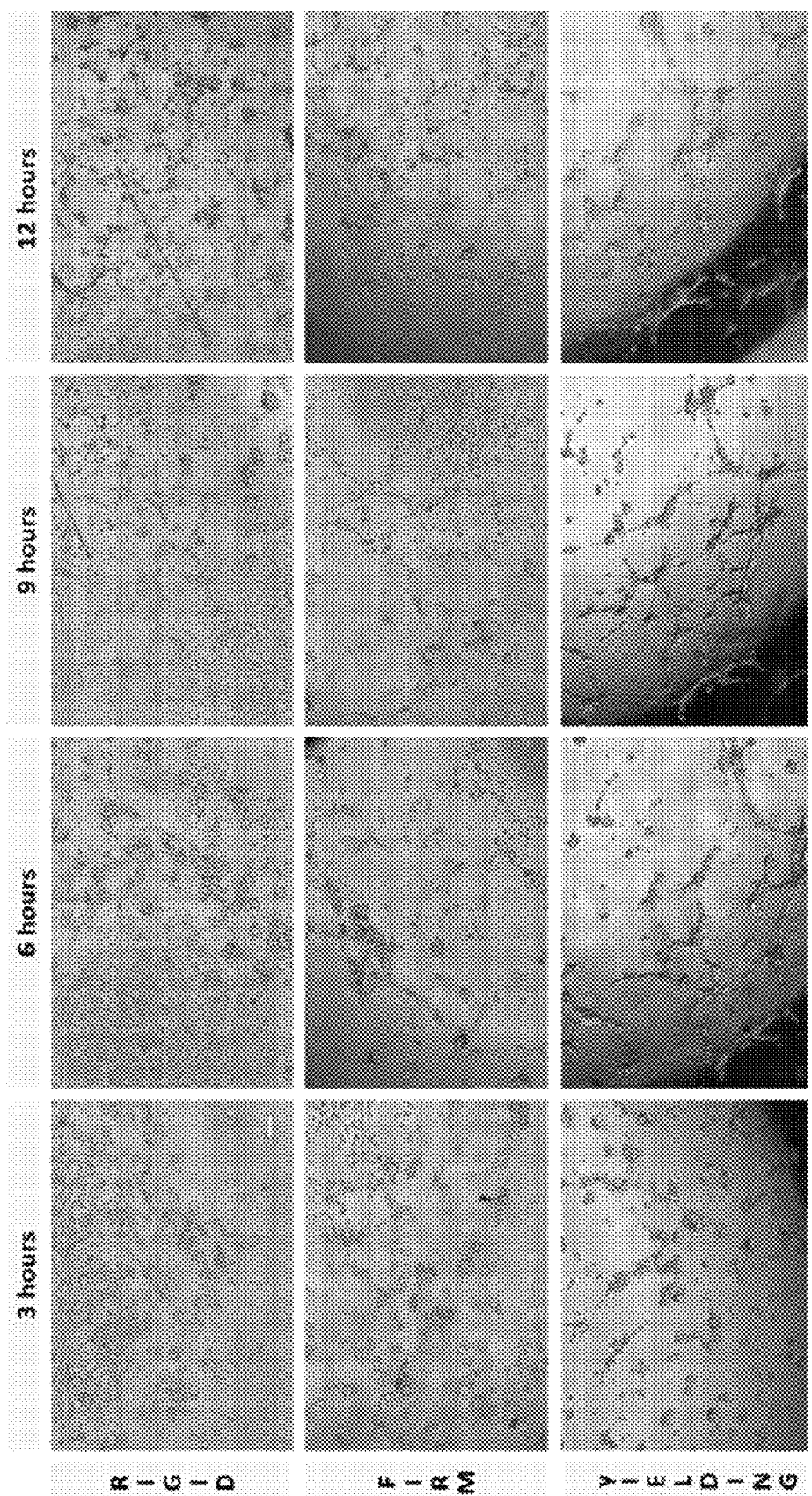
FIG. 8: Time interval images of EPCs on rigid, firm, and yielding substrates. Rapid chain assembly and CLS formation on softer substrates along the 12 hour culture period. Scale bar is 100 µm.
Figure 9E:
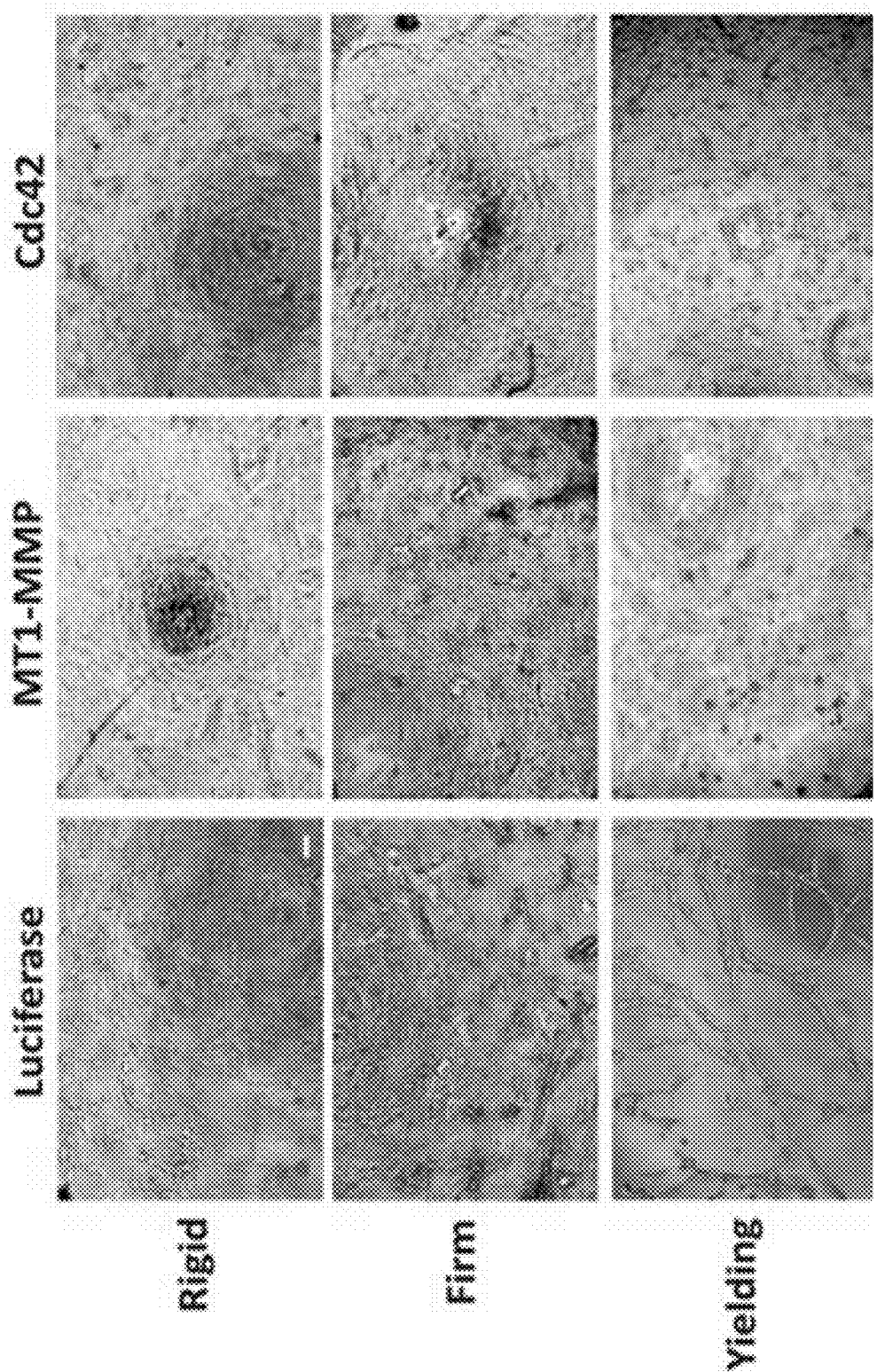

To study the kinetics of tube morphogenesis on substrates with different mechanics, the following parameters were considered: (i) CLS phenotype; (ii) EPC layering and lengthening; and, (iii) cytoplasmic vacuole formation, extension, and fusion to open lumen compartments. EPCs were seeded on rigid, firm, and yielding substrates in media containing high VEGF concentrations. Time-interval images show that EPCs assembled in a chain in an efficient and rapid manner on softer substrates (FIG. 8), resulting in a significant increase in tube length—from 130±3 µm on rigid substrate to 140±4 µm on firm substrate to 200±5 µm on yielding substrate (FIG. 3A). Similarly, the area covered by CLSs also increased—from 560±10 µm$^2$ on rigid substrate to 630±24 µm$^2$ on firm substrate to 1011±66 µm2 on yielding substrate (FIG. 3B). Although the extent of CLSs that formed on all of the substrates increased over time, with further incubation the extent of CLSs that formed on rigid and firm substrates did not achieve the predominance of CLSs that formed on yielding substrate (data not shown). In addition, CLSs that formed on yielding substrate were further found to be considerably thicker (20±1 µm) than those that formed on either rigid (17±1 µm) or firm (18±0.3 µm) substrates, with branching and visible hollowing indicative of tubular structure with open lumen space (FIGS. 3C-3E).

Immunofluorescence.

EPCs cultured on HA hydrogels for 12 hours were fixed using formalin-free fixative (Accustain, Sigma, St. Louis) for 20 minutes, and washed with PBS. For staining, cells were permeabilized with a solution of 0.1% Triton-X for ten minutes, washed with PBS, and incubated for one hour with mouse anti-human VE-Cad (1:200; BD Biosciences, San Jose, Calif.), rinsed twice with PBS, and incubated with anti-mouse IgG Cy3 (1:50; Sigma, St. Louis). After rinsing twice with PBS, cells were incubated with either FITC-conjugated lectin (1:40, Vector, Burlingame, Calif.) or FITC conjugated phalloidin (1:40, Molecular Probes, Eugene, Oreg.) for one hour, rinsed with PBS, and incubated with DAPI (1:1000; Roche Diagnostics, Basel, Switzerland) for an additional ten minutes. The hydrogels were gently placed into a glass bottom dish (Matek, Ashland, Mass.) and mounted with fluorescent mounting medium (Dako, Glostrup, Denmark). The immunolabeled cells were examined using fluorescence microscopy (Olympus BX60, Center Valley, Pa.). A sequence of z-stack images was obtained using confocal microscopy (LSM 510 Meta, Carl Zeiss Inc., Thornwood, N.Y.).

Transmission Electron Microscopy (TEM).

EPCs cultured on hydrogels for six and twelve hours were prepared for TEM samples as previously described (Perkins et al., *Methods Mol. Biol.*, vol. 372, pp. 467-483, 2007). Briefly, cells were fixed with 3.0% formaldehyde, 1.5% glutaraldehyde in 0.1 M Na cacodylate, 5 mM $Ca^{2+}$, and 2.5% sucrose at room temperature for one hour and washed three times in 0.1 M cacodylate/2.5% sucrose pH 7.4 for 15 minutes each. The cells were postfixed with Palade's $OsO_4$ on ice for one hour, rinsed with Kellenberger's uranyl acetate, and then processed conventionally through Epon embedding on a 16-well Lab-Tek chamber slide (NUNC, Rochester, N.Y.). Serial sections were cut, mounted onto copper grids, and viewed using a Phillips EM 410 transmission electron microscope (FEI, Hillsboro, Oreg.). Images were captured with an FEI Eagle 2k camera.

Figure 4E:
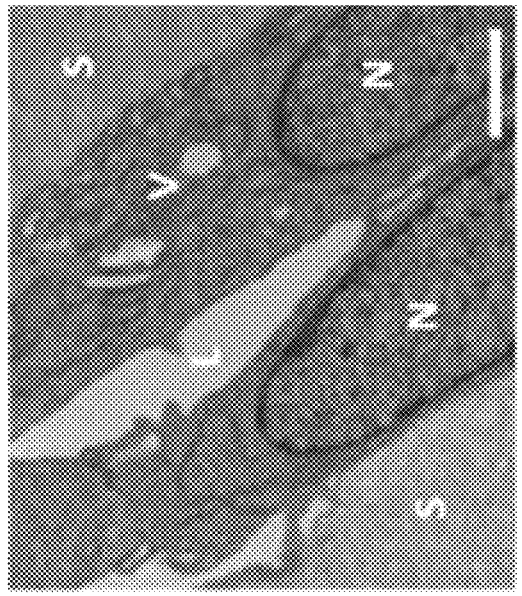
Figure 4D:
Figure 4F:
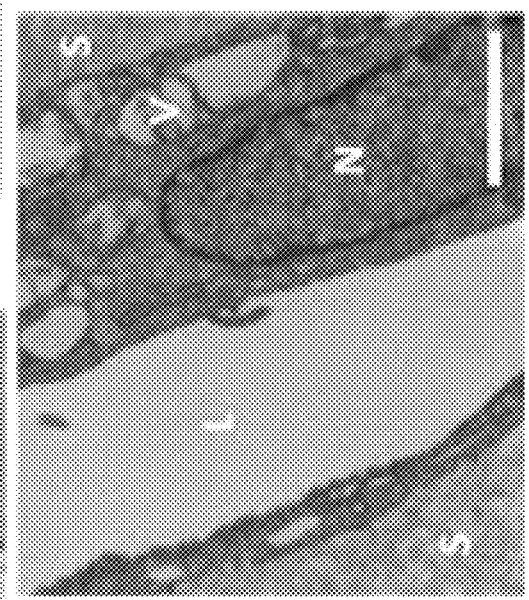
Figure 5B:
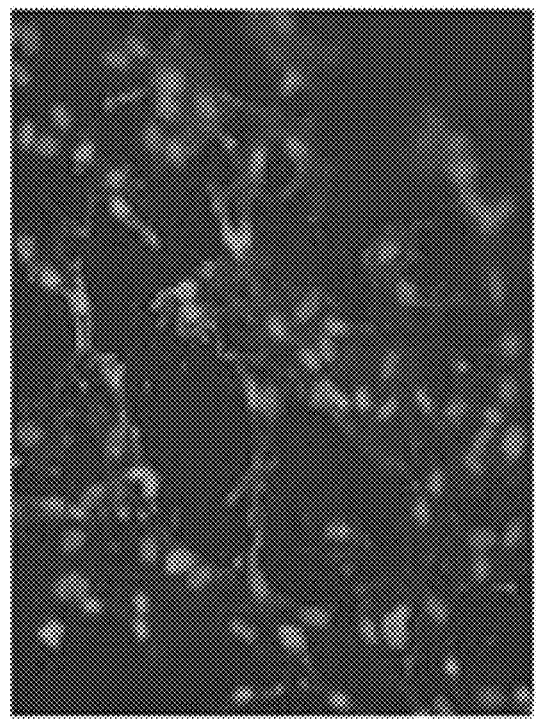
FIGS. 5A-5F: MT1-MMP and Cdc42 required for CLS formation from EPC. EPCs transfected with the indicated siRNA were seeded on rigid (FIGS. 5A and 5B), firm (FIGS. 5C and 5D), and yielding (FIGS. 5E and 5F) substrates and supplemented with 50 ng/ml VEGF for 12 hours with no indication of CLS formation as demonstrated by fluorescence microscopy of VE-cad (red) and nuclei (blue). Scale bar is 100 µm.
Figure 5A:
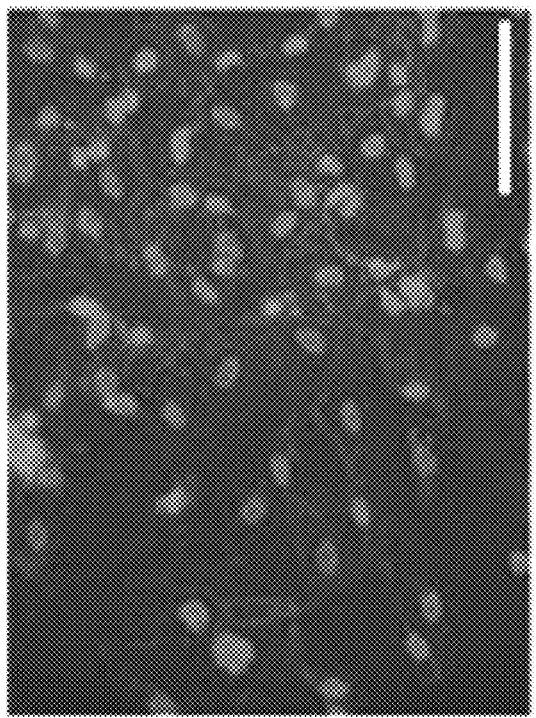
Figure 5D:
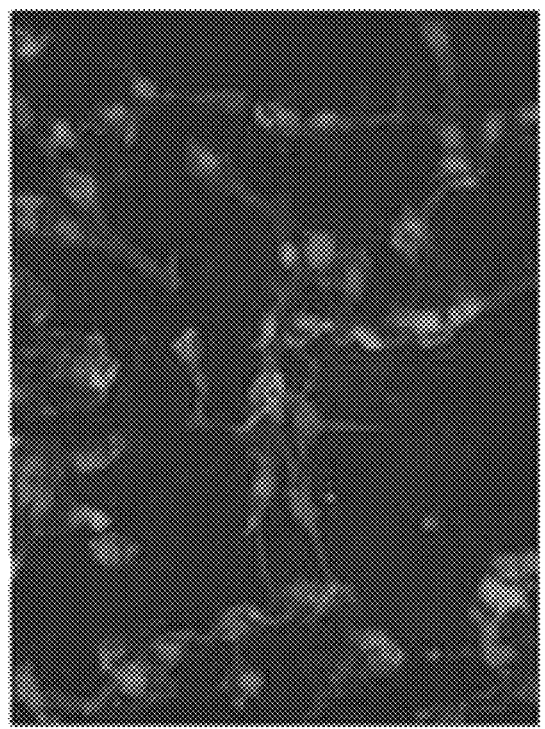
Figure 5C:
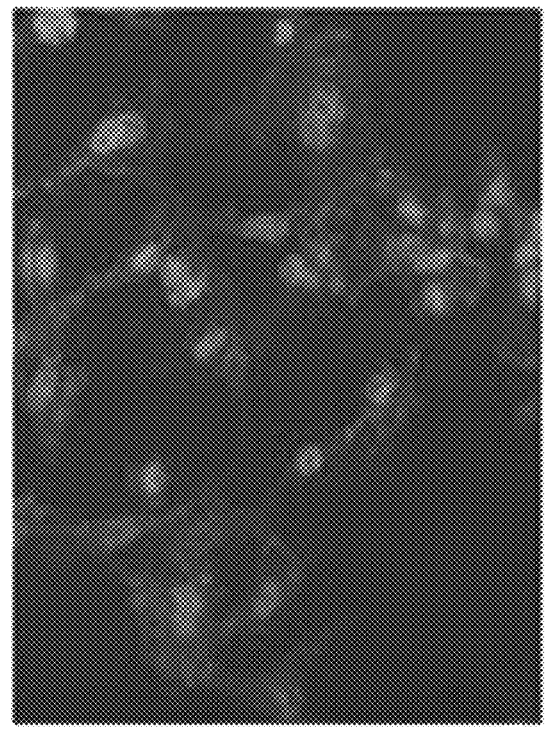
Figure 5F:
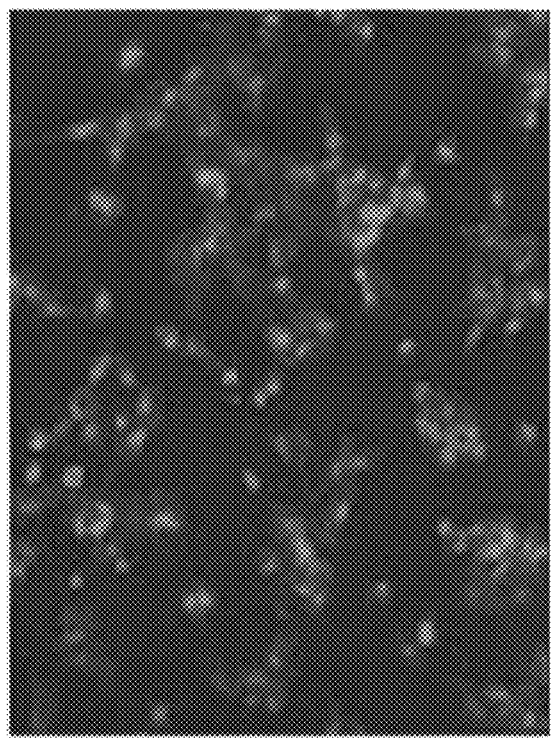
Figure 5E:
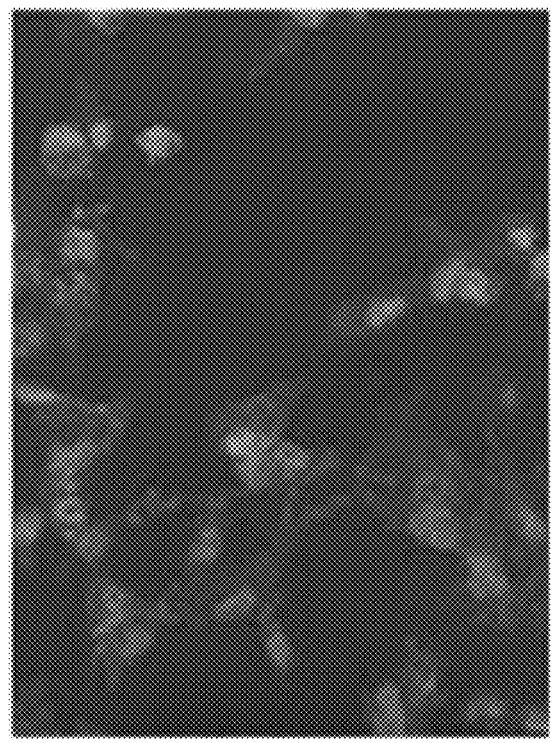

To investigate the kinetics of cytoplasmic vesicle formation, coalescing, and elongation to an open lumen, TEM analysis was performed after six and twelve hours of culture. After six hours, cytoplasmic vacuoles were observed in EPCs cultured on all substrates. However, while EPCs on rigid substrate were organized into two to three cell layers, they elongated on firm substrate and both elongated and organized into a single layer on the yielding substrate (FIGS. 4A-4C). After twelve hours of culturing, EPCs on rigid substrate were more elongated and contained many vacuoles. On firm substrate, cells were elongated with larger vacuoles, and lumen compartments were observed on several occasions. On yielding substrate, we observed complex structures with open lumen spaces and very lengthened cells (FIGS. 4D-4F).

RNAi Transfection:

EPCs were transfected with siGENOME SMARTpool human Cdc42 and MT1-MMP (Dharmacon, Lafayette, Colo.) using the manufacturer's protocol. Briefly, the RNAi transfection solution was prepared by mixing a serum-free and antibiotic-free EGM (PromoCell GmbH, Germany) with DharmaFECT2 RNAi transfection reagent (Dharmacon). EPCs were cultured to 90% confluence on a 24-well plate (NUNC, Roskilde, Denmark). For transfection, EPC growth medium was removed and replaced with 400 µL of antibiotic-free EGM (PromoCell, Heidelberg, Germany) and 100 µL transfection solution in each well, to achieve a final RNAi concentration of 50 nmol/L. Transfected cells were incubated at 37° C., and the medium was replaced with a fresh EGM medium after 24 hours. RNA analysis was performed after 48 hours, and protein analysis was performed after 72 hours. Confirmed transfected EPCs were used for experiments after 48 to 96 hours.

MT1-MMP has been reported to support neovascularization by allowing matrix degradation at the migrating cell front (Van Hinsbergh et al., *Arterioscler. Thromb. Vasc. Biol.*, vol. 26, pp. 716-728, 2006), as well as by creating a physical space to control tube and lumen morphogenesis (Chun et al., *J. Cell. Biol.*, vol. 167, pp. 757-767, 2004; Saunders et al., *J. Cell Biol.*, vol. 175, pp. 179-191, 2006). The function of MT1-MMP in tube morphogenesis of EPCs on various levels of substrate stiffness was examined using an RNAi suppression approach. EPCs treated with siRNA targeting the MT1-MMP (FIG. 9A) were seeded on the different substrates. In contrast to the Luciferase-treated EPCs (control), siRNA suppression of MT1-MMP mitigated CLS formation on firm and yielding substrates, with more rounded cell morphology, while allowing cell spreading on rigid substrates (FIGS. 5A, 5C, 5E and 9E).

Cdc42 has been demonstrated to regulate EC morphogenesis through vacuole and lumen formation (Bayless et al., *J. Cell. Sci.*, vol. 115, pp. 1123-1136, 2002), as well as to mediate cell spreading, motility, growth, and differentiation through cytoskeletal remodeling and focal adhesion assembly (Jaffe et al., *Annu. Rev. Cell Dev. Biol.*, vol. 21, pp. 247-269, 2005; Mammoto et al., *Curr. Opin. Hematol.*, vol. 15, pp. 228-234 2008). An RNAi suppression approach was used to examine whether Cdc42 is the connecting link by which EPCs respond to substrate stiffness during tube morphogenesis. EPCs were treated with siRNA that targeted the small Rho GTPase Cdc42 (FIG. 9B) and were seeded on the different substrates. Luciferase-treated (control) EPCs were able to spread and form some extent of CLSs on rigid and firm substrates and could form CLSs to a greater extent on yielding substrate. However, siRNA suppression of Cdc42 prevented EPC tube morphogenesis on all substrates; we observed rounded cell morphology on the yielding substrate and a more spreading morphology on the rigid and firm substrates (FIGS. 5B, 5D, and 5F and FIG. 9E).

Real-Time RT-PCR.

Two-step RT-PCR was performed on EPCs cultured in media supplemented with 1 ng/ml or 50 ng/ml VEGF. Total RNA was extracted using TRIzol (Gibco, Invitrogen Co., Carlsbad, Calif.) according to the manufacturer's instructions. Total RNA was quantified by an ultraviolet spectrophotometer, and the samples were validated for no DNA contamination. RNA (1 µg per sample) was reversed transcribed using M-MLV (Promega Co., Madison, Wis.) and oligo(dT) primers (Promega Co.) according to the manufacturer's instructions. We used the TaqMan Universal PCR Master Mix and Gene Expression Assay (Applied Biosystems, Foster City, Calif.) for MMP-1, MMP-2, MT1-MMP, HPRT1 and β-ACTIN, according to the manufacturer's instructions. The TaqMan PCR step was performed in triplicate with an Applied Biosystems StepOne Real-Time PCR system (Applied Biosystems), using the manufacturer's instructions. The relative expression of MMP1, MMP2, and MT1-MMP was normalized to the amount of HPRT1 or β-ACTIN in the same cDNA by using the standard curve method described by the manufacturer. For each primer set, the comparative CT method (Applied Biosystems) was used to calculate amplification differences between the different samples. The values for experiments (n=3) were averaged and graphed with standard deviations. Similar procedures were used to analyze the expressions of Cdc42 and MT1-MMP from the RNAi experiments.

To examine whether VEGF would induce MMP production, real time RT-PCR was performed to compare MMP expression in EPCs cultured on rigid, firm, and yielding substrates supplemented with high VEGF, to their counterparts cultured with low VEGF. After 12 hours of incubation in media supplemented with high VEGF, EPCs cultured on all substrate showed increased production of MMPs. Specifically, EPCs cultured on rigid and firm substrates with high VEGF produced three times the MMP-2 and four times the MMP-1 and MT1-MMP produced by EPCs cultured in media supplemented with low VEGF concentration. EPCs cultured on yielding substrate supplemented with high VEGF showed a smaller, but significant, increase in MT1-MMP, MMP-1, and MMP-2 compared to their counterpart cultured in low VEGF concentration (FIGS. 2B-2D). When EPCs were cultured in media supplemented with high VEGF concentration, the MMP production decreases as the stiffness of the substrate was reduced (FIGS. 2E-2G).

Western Blot.

The relative amounts of MT1-MMP or Cdc42 in RNAi transfected EPCs were detected using Western Blotting of whole cell lysates prepared in standard extraction buffer containing 4% SDS, 20% glycerine, and 0.0125 M Tri-HCl pH 6.8. Protein (20 µg) from these samples was separated in a 12.5% Criterion Tris-HCl Gel (Bio-Rad Lab., Hercules, Calif.) for 40 minutes using Tris/glycine/SDS running buffer. Resolved proteins were transferred to immuno-blot nitrocellulose membranes (Bio-Rad Lab) and blocked with 3% dry-milk in Tris buffered salinetween (TBS-T). The membranes were immunoprobed overnight with anti-human rabbit monoclonal antibodies to MT1-MMP (1:1,000, Epitomics, Burlingame, Calif.) and to Cdc42 (1:1,000, Cell Signaling Technology, Beverly, Mass.). For loading control, the membranes were probed with anti-human mouse beta-Actin (1:1,000, Cell Signaling Technology). Next, membranes were treated with either HRP-conjugated anti-rabbit or anti-mouse IgG secondary antibodies (1:1,000, Cell Signaling Technology) and then developed by adding Super-Signal West Pico Chemiluminescent Substrate (Thermo Scientific Pierce, Rockford, Ill.).

Statistical Analysis.

Statistical analysis of CLSs quantification, MMP production, and RNAi suppression data was performed using GraphPad Prism 4.02 (GraphPad Software Inc., La Jolla, Calif.). Parametric two way ANOVA test were performed to assess the significance of MMP production by EPCs among rigid, firm, and yielding substrates cultured in low and high VEGF concentrations. Unpaired Student's t-tests were performed to analyze CLSs quantification and RNAi suppression data. Significance levels were set at *$p<0.05$, $p<0.01$, and *$p<0.001$, respectively.

Results

Hydrogels with defined compositions and tunable elasticity can be used for in vitro tube morphogenesis. These hydrogels served as substrates of varying stiffnesses, allowing for varying the kinetics of EPC tubulogenesis. Viscoelasticity measurements during in situ gelation demonstrate three distinct substrate stiffness profiles: rigid, firm, and yielding. While low levels of VEGF allowed EPCs to spread on all substrates, high levels of VEGF were required to initiate tube morphogenesis and to activate MMPs, whose expression declined with the decrease of matrix stiffness. We then observed that increased tube morphogenesis—including CLS progression, vesicle formation, expansion (in both size and number) and fusion to lumens—corresponded to decreased substrate rigidity. RNA interference (RNAi) studies further showed that EPCs required MT1-MMP and Cdc42 to undergo tube morphogenesis.

Figure 6A:
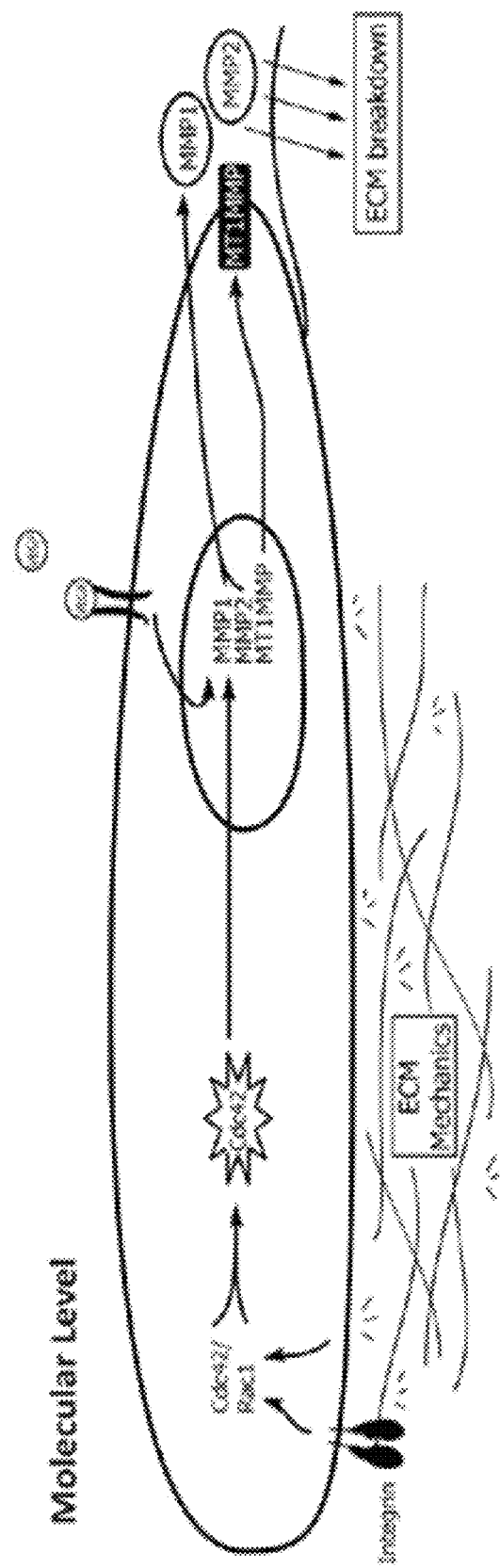
Figure 7:
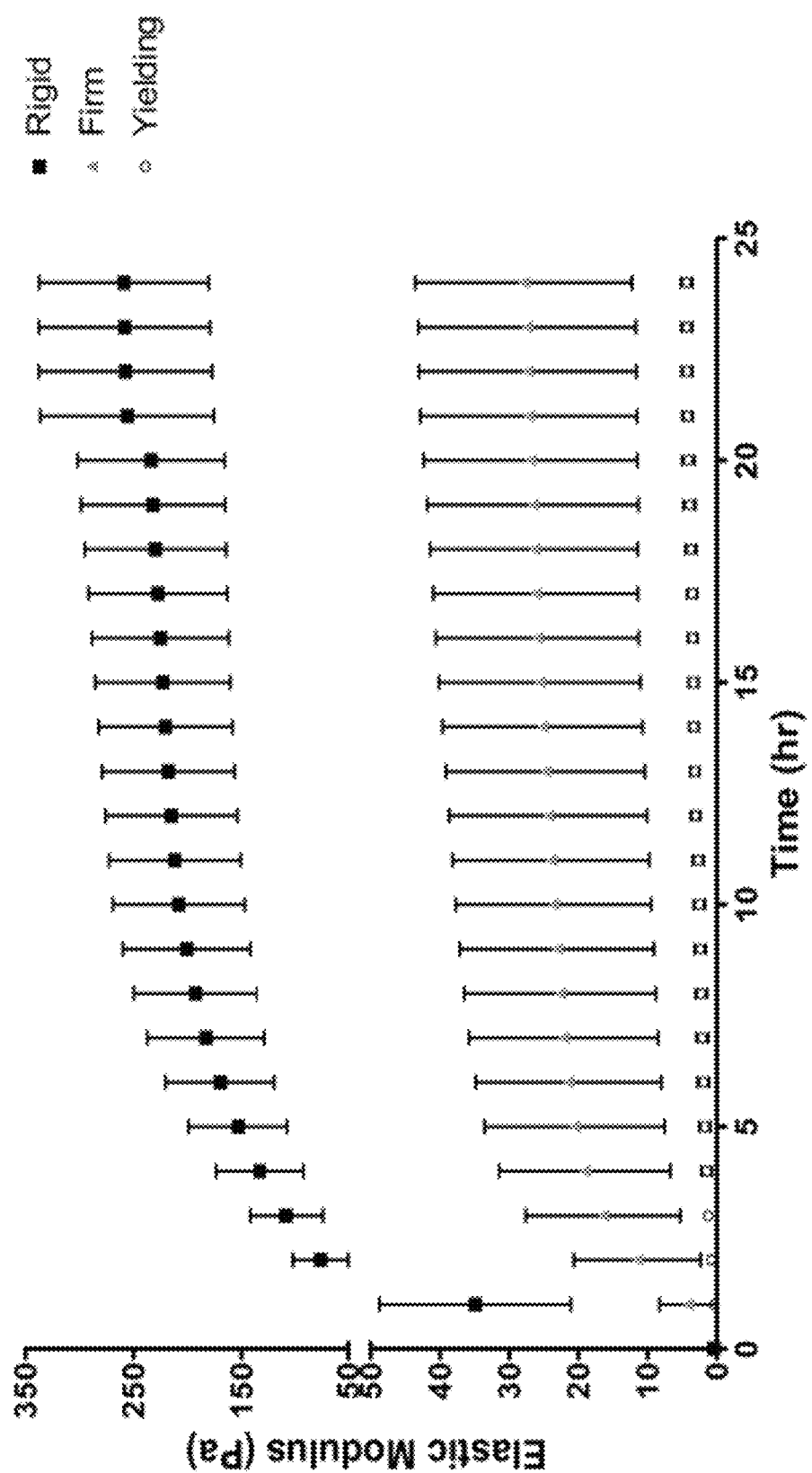
FIG. 7: Viscoelasticity of hydrogels. Microrheology measurements of HA:gelatin over 24 hours of gelation show three distinct profiles of hydrogel mechanics: rigid, firm and yielding. Values shown are means±SD for elastic modulus (G') over 24 hours during the in situ gelation.

Utilizing chemically and mechanically defined hydrogels in an in vitro culture system for angiogenesis, tube morphogenesis can be evaluated over a range of elasticity softer than usually available in vitro and relevant for vascular morphogenesis (10 Pa to 650 Pa), as well as the response to growth factor administration. Growth factors, for example VEGF, are a prerequisite for instigation of angiogenesis and later progress in tube morphogenesis regulated by mechanical stresses from the ECM (FIG. 6A). First, MMP production induced by growth factors reduces the mechanical resistance of the ECM and allows EPC migration and reorganization. This MMP production is co-regulated by matrix stiffness, as EPCs cultured on the rigid and firm substrates have to produce more MMPs to overcome the extra mechanical barrier. At this stage, reduced elasticity of the ECM promotes tubulogenesis, which is characterized by a significant increase in mean tube length, tube area, and thickness as matrix stiffness is reduced from rigid to yielding. Although EPCs cultured on rigid and firm substrates produce more MMPs, most likely to overcome the extra mechanical resistance, the local decrease in substrate stiffness cannot support predominant CLS formation. Hence, EPCs cultured on the yielding substrates are able to form predominant CLSs with extended vacuoles and open lumens.

Vessel morphogenesis is a highly dynamic process in which invasion, motility, and lumenogenesis occur concurrently in different regions of the developing tube. In contrast to angiogenic sprouting, cell hollowing is a mechanism by which individual cells generate vacuoles through the pinocytosis process; these vacuoles then coalesce, forming a lumen that connects to the lumens of neighboring cells (Lubarsky et al., *Cell*, vol. 112, pp. 19-28, 2003; Kamei et al., *Nature*, vol. 442, pp. 453-456, 2006; Davis et al., *Exp. Cell. Res.*, vol. 224, pp 39-51, 1996. Iruela-Arispe et al., *Dev Cell.*, vol. 16, pp. 222-231, 2009). In response to VEGF and matrix stiffness, EPCs produce MMPs that allow further cellular migration and connection into CLSs (FIG. 2A). Furthermore, as demonstrated by the kinetics of CLS formation along 12 hours (FIG. 8), vacuoles formation occurs within 6 hours (FIGS. 4A-4C) and enlarged vacuoles and lumens within 12 hours (FIGS. 4D-4F).

Example 2

Materials and Methods

Human ECFCs

Human umbilical cord blood ECFCs isolated from outgrowth clones, provided by Dr. Yoder, Indiana University School of Medicine, expanded in endothelial growth media (EGM; PromoCell GmbH, Germany) and used for experiments between passages 6 and 8 as previously described (Hanjaya-Putra et al., *Journal of Cellular and Molecular Medicine*, vol. 14, no. 10, pp. 2436-2447, 2010).

Synthesis of AHA-Hydrogels

Acrylated hyaluronic acid (AHA) was synthesized using a two-step protocol: (1) Synthesis of the tetrabutylammonium salt of HA (HA-TBA) was performed by reacting sodium hyaluronate (64 kDa, Lifecore) with the highly acidic ion exchange resin Dowex-100 and neutralization with 0.2 M TBA-OH. (2) Coupling of acrylic acid (2.5 eq) and HA-TBA (1 eq, repeat unit) in the presence of dimethylamino pyridine (DMAP; 0.075 eq) and di-tert-butyl-dicarbonate (1.5 eq) in DMSO, followed by dialysis and lyophilization. 1H NMR spectrum was used to confirm the final percent modification of the AHA-hydrogels.

Peptides

The cell adhesive peptide GCGYGRGDSPG (SEQ ID NO: 2) (MW: 1025.1 Da; bold italics indicates RGD integrin-binding domain), cell non-adhesive peptide GCGYGRDGSPG (SEQ ID NO: 3) (MW: 1025.1 Da; bold italics indicates RDG the mutated integrin-binding domain), MMP-sensitive crosslinker GCRDGPQG↓IWGQDRCG (SEQ ID NO: 1) (MW: 1754.0 Da; down arrow indicate the site of preteolytic cleavage), and MMP-insensitive crosslinker GCRDGDQGIAGFDRCG (SEQ ID NO: 4) (MW: 1754.0 Da), all with >95% purity (per manufacturer HPLC analysis), were obtained from GenScript Corporation (Piscataway, N.J., USA).

Generation of Vascular Constructs.

AHA polymer (3 wt %) was dissolved in a triethanolamine-buffered saline (TEOA buffer: 0.2 M TEOA, 0.3 M total osmolarity, pH 8.0). The cells adhesive peptides (RGD, genscript, NJ) dissolved in TEOA buffer was added to the AHA solution at a final peptide concentration of 0.37 mM, 3.7 mM, and 14.8 mM (corresponding to 1%, 10%, and 20% of available acrylate groups within 3 wt % AHA). Recombinant human $VEGF_{165}$ (Pierce, Rockford, Ill.), bFGF (Invitrogen), Ang-1 (R&D), TNF-α, and SDF-1 were added at 50 ng/ml into the AHA-RGDS mixture and allowed to react for 1 hour with gentle shaking. Human umbilical cord blood ECFCs were encapsulated in HA hydrogels with densities of $5.10^6$ cells/ml. Following the re-suspension of cells into this solution, MMP peptide crosslinker (MMP, genescript) dissolved in TEOA buffer was added (corresponding to the 20% of available acrylate groups within 3 wt % AHA) Immediately after the addition of the MMP crosslinker, 50 µl of this mixture was pipetted into sterile molds (5 mm diameter, 2 mm height), and allowed to react for 15 minutes at room temperature inside the laminar flow hood. The formed constructs were cultured for up to 3 days in EGM (PromoCell GmbH, Germany). Visualization and image acquisition were performed using an inverted light microscope (Olympus IX50, Center Valley, Pa.) and confocal microscope (LSM 510 Meta, Carl Zeiss Inc., Thornwood, N.Y.) at various time points.

Viscoelasticity Measurement.

Oscillatory shear measurements of the elastic modulus (G') were obtained using a constant strain rheometer with steel cone-plate geometry (25 mm in diameter; RFS3, TA Instruments, New Castle, Del.) as previously described (Hanjaya-Putra et al., *Journal of Cellular and Molecular Medicine*, vol. 14, no. 10, pp. 2436-2447, 2010; Vanderhooft et al., *Macromolecular Bioscience*, vol. 9, pp. 20-28, 2009). Briefly, oscillatory time sweeps were performed on three samples (n=3) for each hydrogels samples at various time point. The strain was maintained at 20% during the time sweeps by adjusting the stress amplitude at a frequency of 1 Hz. This strain and frequency were chosen because G' was roughly frequency independent within the linear viscoelastic regime. The tests occurred in a humidified chamber at a constant temperature (25° C.) in 30 second intervals. The Young's modulus (substrate viscoelasticity) was calculated by E=2G'(1+v). HA-gelatin hydrogels can be assumed to be incompressible (Vanderhooft et al., *Macromolecular Bioscience*, vol. 9, pp. 20-28, 2009), such that their Poisson's ratios (v) approach 0.5 and the relationship becomes E=3G' (Mammoto et al., *Nature*, vol. 457, pp. 1103-1108, 2009, Boudou et al., *Biorheology*, vol. 43, pp. 721-728, 2006).

VEGF Released and Degradation Study

At various time points, 1 mL of conditioned media from the gels alone and gels containing cells were collected and replaced with a fresh growth media. At final time point (day 3), the gels were degraded using endogenous 1,000 IU/ml hyaluronidase IV (Sigma, XXX). After 24 hours the gels were completely degraded and the conditioned media were collected. All of the samples (n=3) were stored at −80° C. before performing an ELISA analysis for VEGF and uronic acid assay. VEGF release profile were performed using an ELISA kit (Pierce Biotechnology) following manufacturer's instructions. Briefly, $VEGF_{165}$ in the ELISA kit standards and samples were captured on the anti-human VEGF165 antibody-coated microplate. After removing unbound proteins, biotinylated antibody reagent was added to bind to the secondary site on $VEGF_{165}$. Then, to produce a colorimetric signal, streptavidin-horseradish peroxidase was added to bind to TMB. Standards were prepared according to the manufacturer's instructions. Plate washing was performed three times between each step to remove any excess reagents. The colorimetric signal was detected using a UV microplate spectrophotometer (SpectraMax Plus, Molecular Devices, Sunnycale, Calif.) at absorbance wavelengths of 450 and 550 nm. The standard curve was interpolated to determine the amount of VEGF165 at each predetermined time point, Results are presented in terms of cumulative release as a function of time. To study the degradation kinetic of the gels by the cells, the conditioned media was also analyzed via a modified uronic acid assay as previously reported (Burdick et al., *Biomacromolecules*, vol. 6, no. 386-391, 2005).

Vacuoles Visualization and Integrins Blocking

Quantitation of vacuoles and lumen formation was performed following previous reported protocol (Bayless et al., *Am. J. Pathol.*, vol. 156, pp. 1673-1683, 2000). For each condition 200 cells were analyzed for vacuole and lumen formation. A cell was considered to be vacuolating if more than 30% of the cell's area contained a vacuole or lumen. For further visualization using confocal microscopy, FM-464 vacuole staining (Invitrogen) was performed following manufacturer's protocol. To determine the integrins involved, various antibodies directed toward human integrin subunits and heterodimers were added.

Immunofluorescence.

Human umbilical cord blood ECFCs cultured in flasks or encapsulated ECFCs cultured within HA hydrogels for 48 hours were fixed using formalin-free fixative (Accustain, Sigma) for 20 minutes, and washed with PBS. For staining, cells were permeabilized with a solution of 0.1% Triton-X for ten minutes, washed with PBS and incubated for one hour with mouse anti-human VE-Cad (1:200; BD Biosciences, San Jose, Calif.), anti-human CD44 (1:100; Sigma), or anti-human CD168 (1:50; Novocastra, Newcastle, UK) rinsed twice with PBS, and incubated with anti-mouse IgG Cy3 (1:50; Sigma). After rinsing twice with PBS, cells were incubated with either FITC-conjugated lectin (1:40, Vector, Burlingame, Calif.) or FITC-conjugated phalloidin (1:40, Molecular Probes, Eugene, Oreg.) for one hour, rinsed with PBS, and incubated with DAPI (1:1000; Roche Diagnostics, Basel, Switzerland) for an additional ten minutes. The hydrogels were directly imaged by inverted fluorescence microscopy in the 96-well glass bottom plate. The immunolabeled cells were examined using confocal microscopy (LSM 510 Meta, Carl Zeiss Inc.).

Transmission Electron Microscopy (TEM).

At various time points throughout vascular morphogenesis, the ECFCs and HA-hydrogels constructs (n=3, for each time point) were prepared for TEM samples as previously described (Perkins et al., *Methods Mol. Biol.*, vol. 372, pp. 467-483, 2007). Briefly, the constructs were fixed with 3.0% formaldehyde, 1.5% glutaraldehyde in 0.1 M Na cacodylate, 5 mM Ca2+, and 2.5% sucrose at room temperature for one hour and washed three times in 0.1 M cacodylate/2.5% sucrose pH 7.4 for 15 minutes each. The cells were postfixed with Palade's $OsO_4$ on ice for one hour, rinsed with Kellenberger's uranyl acetate, and then processed conventionally through Epon embedding. Serial sections were cut, mounted onto copper grids, and viewed using a Phillips EM 410 transmission electron microscope (FEI, Hillsboro, Oreg.). Images were captured with an FEI Eagle 2k camera.

Scanning Electron Microscopy (SEM).

The ultrastructure of the hydrogels was studies using SEM (FEI Quanta ESEM 200) as was previously described (Sun et al., *Carbohydrate Polymers*, vol. 65, pp. 273-287, 2006). Briefly, the hydrogels were swelled in PBS for 24 hours, quickly frozen in liquid nitrogen, and then freeze-dried in a Virtis Freeze Drier (Gardiner, N.Y.) under vacuum at −50° C. for 3 days until the samples became completely dry. The freeze-dried hydrogels were fractured carefully to reveal the interior and mounted onto aluminum stubs with double side carbon tape and sputter-coated (Anatech Hummer 6.2 Sputter Coater) with Ag for 1 minute. The interior morphology of the hydrogels was examined using SEM at 25 kV and 12 nA.

Quantification of CLSs.

The LIVE/DEAD Viability/Cytotoxicity Kit (Invitrogen, Carlsbad, Calif.) was used to visualize CLSs, following the manufacturer's protocol. Briefly, calcein AM dye was diluted in phenol red-free DMEM (Invitrogen, Carlsbad, Calif.) to obtain a final concentration of 2 µM. The constructs were incubated with the dye solution for 30 minutes. After replacing with fresh phenol red-free DMEM, CLSs were visualized using a fluorescent microscope with a 10× objective lens (Axiovert, Carl Zeiss Inc.). We analyzed four image fields per construct from three distinct experiments (n=3) performed in triplicate, using Metamorph software 6.1 (Universal Imaging Co., Downingtown, Pa.) to quantify and compare CLSs formed within each hydrogel.

Real-Time RT-PCR.

Two-step RT-PCR was performed on ECFCs cultured in media supplemented with 1 ng/ml or 50 ng/ml VEGF. The human colon carcinoma cell line LS174T (ATCC, Manassas, Va.) was used as positive control. Total RNA was extracted using TRIzol (Gibco, Invitrogen Co., Carlsbad, Calif.) according to the manufacturer's instructions. Total RNA was quantified by an ultraviolet spectrophotometer, and the samples were validated for no DNA contamination. RNA (1 µg per sample) was reversed transcribed using M-MLV (Promega Co., Madison, Wis.) and oligo(dT) primers (Promega Co.) according to the manufacturer's instructions. We used the TaqMan Universal PCR Master Mix and Gene Expression Assay (Applied Biosystems, Foster City, Calif.) for SPAM1, HPRT1 and β-ACTIN, according to the manufacturer's instructions. The TaqMan PCR step was performed in triplicate with an Applied Biosystems StepOne Real-Time PCR system (Applied Biosystems), using the manufacturer's instructions. The relative expression of SPAM1 was normalized to the amount of HPRT1 or β-ACTIN in the same cDNA by using the standard curve method described by the manufacturer. For each primer set, the comparative CT method (Applied Biosystems) was used to calculate amplification differences between the different samples. The values for experiments (n=3) were averaged and graphed with standard deviations.

Chick Embryo Chorioallantoic Membrane (CAM) Assay

Chick embryo chorioallantoic membrane (CAM) was cultured ex ovo. Briefly, fertilized chicken eggs (Bernies farm, P.A.) were incubated at 37° C. and 60% humidity for 3-4 days. At this time point (E.3-4), the eggs were cleaned with betadine and 70% ethanol and cracked opened into a petri dish, which contained 5-10 mL of DMEM media (invitrogen). The CAM was cultured ex ovo in a humidified incubator at 37° C. in an atmosphere containing 5% $CO_2$. The vascularized constructs (n=8-10, one construct per CAM) were cultured in vitro for 3 days and grafted onto CAM membrane at E.8, and were cultured for an additional 4 days (E.12), in which period the host EC mitotic index is optimum. At E.12, FITC-lectin or dextran was perfused into a major aorta and the constructs were harvested and fixed in formalin free Accustain fixative (Sigma). Analysis was performed using both confocal microscopy and histological sectioning.

Transplantation of Vascularized Constructs

Vascularized constructs were implanted into the flanks of 6-8 weeks old NUDE mice following well established protocol by Dr. Yoder (Mead et al., *Current protocols in stem cell biology*, vol. 6, pp. 2C.1.1-2C.1.27, 2008). Briefly, vascularized constructs were cultured in vitro for 3 days and implanted into each flanks (left or right, 2 constructs per mouse). Eight to ten constructs were implanted for each groups (n=8-10). After two weeks, mice were euthanized and the constructs were harvested and fixed in formalin free Accustain fixative (Sigma). Explants were then paraffin embedded, bisected along major axis, and sectioned (5 µm thick) for immunohistochemical analysis. All animal protocols were approved by the Johns Hopkins University Institutional Animal Care and Use Committee.

Statistical Analysis.

Analysis of CLSs quantification and hyaluronidase expression data was performed on triplicate samples with quadruplicate and duplicate readings at each data point, respectively, and statistical analysis was performed using GraphPad Prism 4.02 (GraphPad Software Inc.). T-tests were performed to determine significance using GraphPad Prism 4.02 (GraphPad Software Inc.). Significance levels were determined using posttests among the three substrates, and were set at *$p<0.05$, $p<0.01$, and *$p<0.001$, respectively. All graphical data were reported.

Results

Figure 10A:
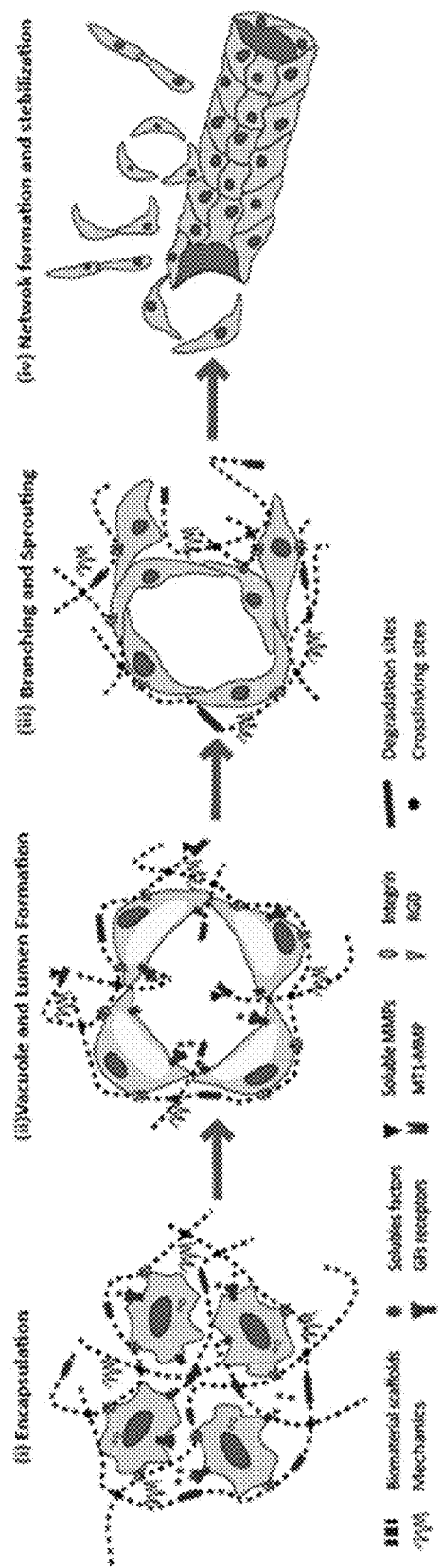

Acrylated HA (AHA) can provide the dynamic cues required for network assembly of encapsulated ECFCs (FIG. 10A). These hydrogels are formed using sequential cross-linking from acrylated HA precursors by reacting with thiol-terminated RGD integrin-binding peptide (thiol group on RGDS react with acrylates along the HA backbone) followed by an addition reaction with thiol-terminated peptide crosslinkers (thiol groups on each end of peptide react with acrylates along the HA backbone) (Khetan et al., *Soft Matter*, vol. 5, no. 8, pp. 1601-1606, 2009). In these AHA hydrogels, an enzymatically degradable peptide that can be cleaved by both MMP-1 and MMP-2 (Lutolf et al., *Proc. Natl. Acad. Sci. U.S.A.*, vol. 100, no. 9, pp. 5413-5418, 2003; Seliktar et al., *J. Biomed. Mater. Res. A*, vol. 68, no. 4, pp. 704-716, 2004), for example a peptide with the sequence GCRDGPQG↓IWGQDRCG (SEQ ID NO: 1), can be used as a crosslinker. An adhesive ligand, such as RGD, which is the sequence within the fibronectin molecule that mediates cell attachment, can also be included. The AHA hydrogels can have about 50% modification (50% of the repeating HA macromer contains acrylate group) to form 3 wt % hydrogels (FIGS. 10B and 10C). Higher acrylate modification and wt % corresponds to relatively dense networks can also be used but do not as effectively support vascular morphogenesis.

Adhesion Compounds

Figure 11A:
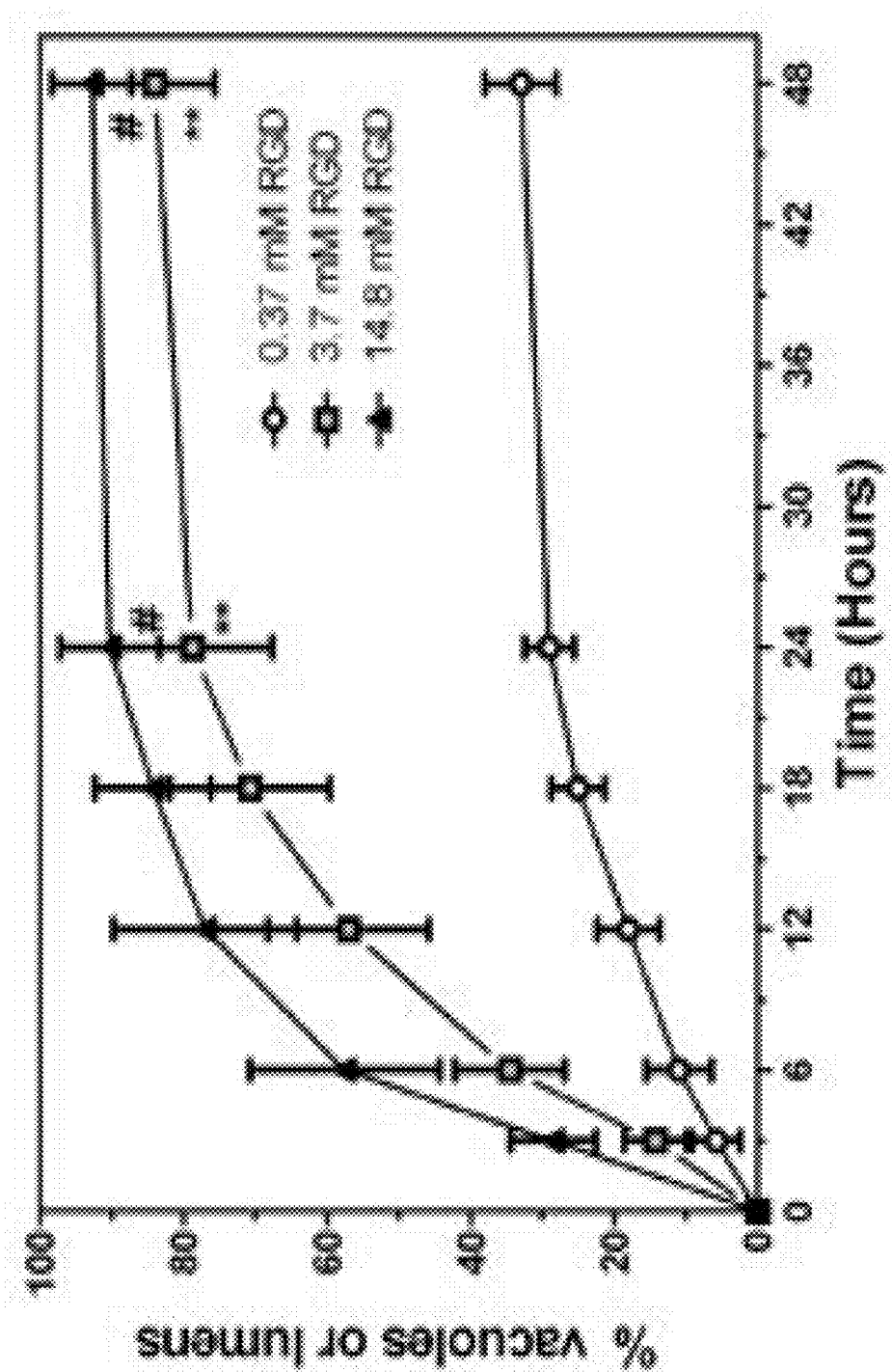
FIGS. 11A-11D: Determining RGD and MMP requirements for ECFC morphogenesis. RGD dose-dependent vacuolation of ECFC is demonstrated by vacuole formation kinetics (FIG. 11A) and represented LM and vacuole vital stain FM 4-64 (cyan) images at 24 hours (FIG. 11B). Scale bars are 100 µm. Insert demonstrate high magnifications of single cells with abundant vacuoles in 3.7 mM RGD. Scale bars are 20 µm. Both RGD adhesion sites and MMP-degradable crosslinker for vacuolation of ECFC are demonstrated by vacuole formation kinetics (FIG. 11C) and represented LM and vacuole vital stain FM 4-64 (cyan) images at 24 hours (FIG. 11D). Scale bars are 50 µm.
Figure 11B:
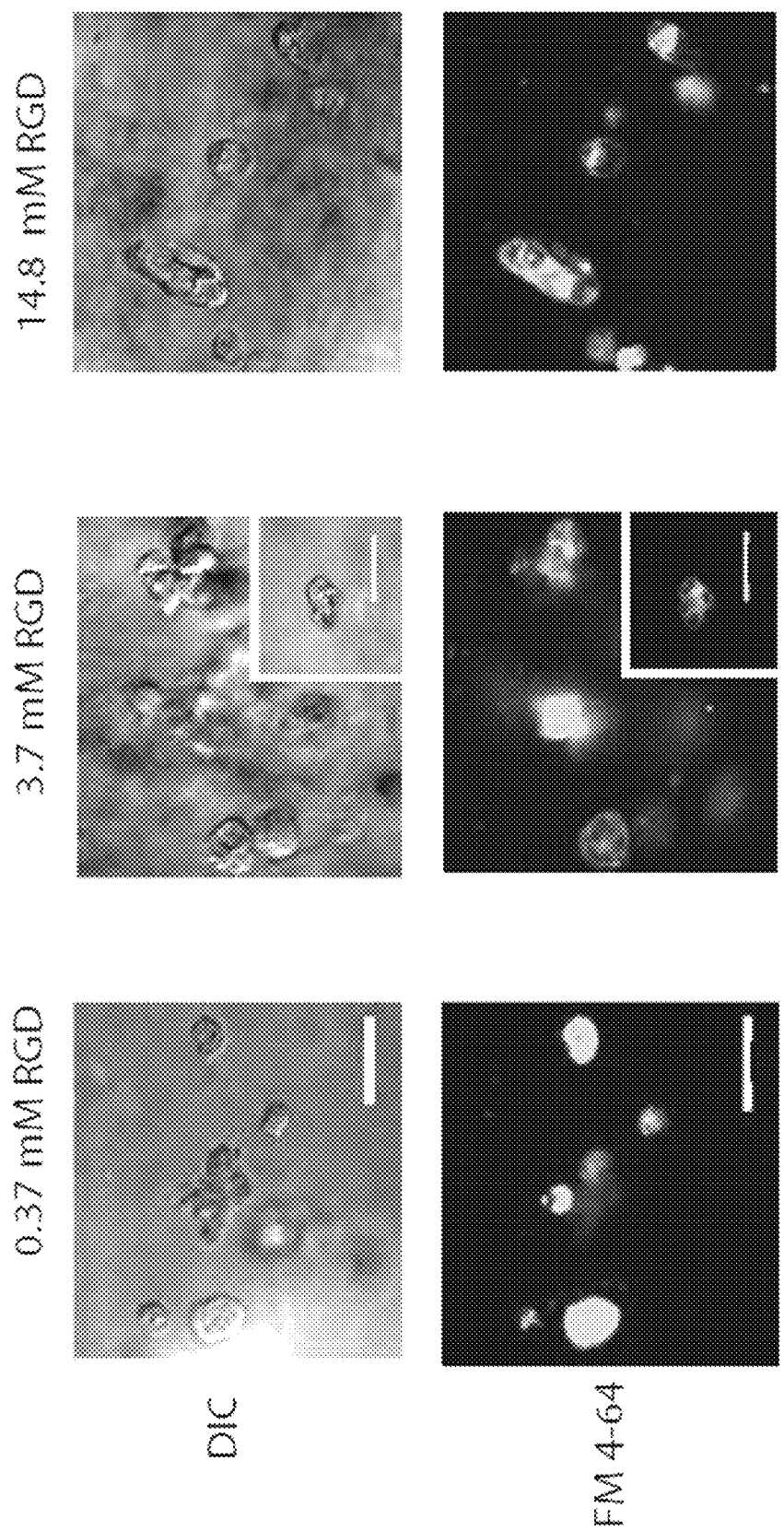

The incorporation rate of the RGD containing peptide can be altered in AHA hydrogels (Khetan et al., *J. Vis. Exp.*, (32), 2009; Khetan et al., *Conf Proc. IEEE Eng. Med. Biol. Soc.*, vol. 1, pp. 2094-2096, 2009) to determine its effect on tubulogenesis. Based on previous publications examining the role of RGD adhesion site in tubulogenesis in fibrin gels (Bayless et al., *Am. J. Pathol.*, vol. 156, no. 5, pp. 1673-1683, 2000), AHA hydrogels were generated with RGD concentrations of 0.37, 3.7, and 14.8 mM, and the kinetics of vacuole and lumen formation were analyzed at various time intervals. Vacuole and lumen formation is dependent on adhesion molecule e.g. RGD, concentration and an example of an optimal RGD concentration in our system is 3.7 mM, which corresponds to 10% of acrylate consumption (FIG. 11A). Very little vacuole formation with no lumen is detected in AHA hydrogels generated with 0.37 mM RGD. Higher concentrations of RGD did not significantly enhanced vacuole formation but created viscous gels which were difficult to image and handle.

When a mutated adhesion site, RGE, was used, little to no vacuole and lumen formation is observed. These results are in agreement with previous published data that RGD regulates vacuoles and lumen formation (Bayless et al., *Am. J. Pathol.*, vol. 156, no. 5, pp. 1673-1683, 2000), and that optimum concentration of RGD similar to fibrin gels can be used to initiate vascular morphogenesis in synthetic hydrogels (Gobin et al., *FASEB J.*: 01-0759fje; Lutolf et al., *Nature Biotechnology*, vol. 23, no. 1, pp. 47-55, 2005; Raeber et al., *Biophysical Journal*, vol. 89, no. 2, pp. 1374-1388, 2005).

Crosslinker

Figure 11C:
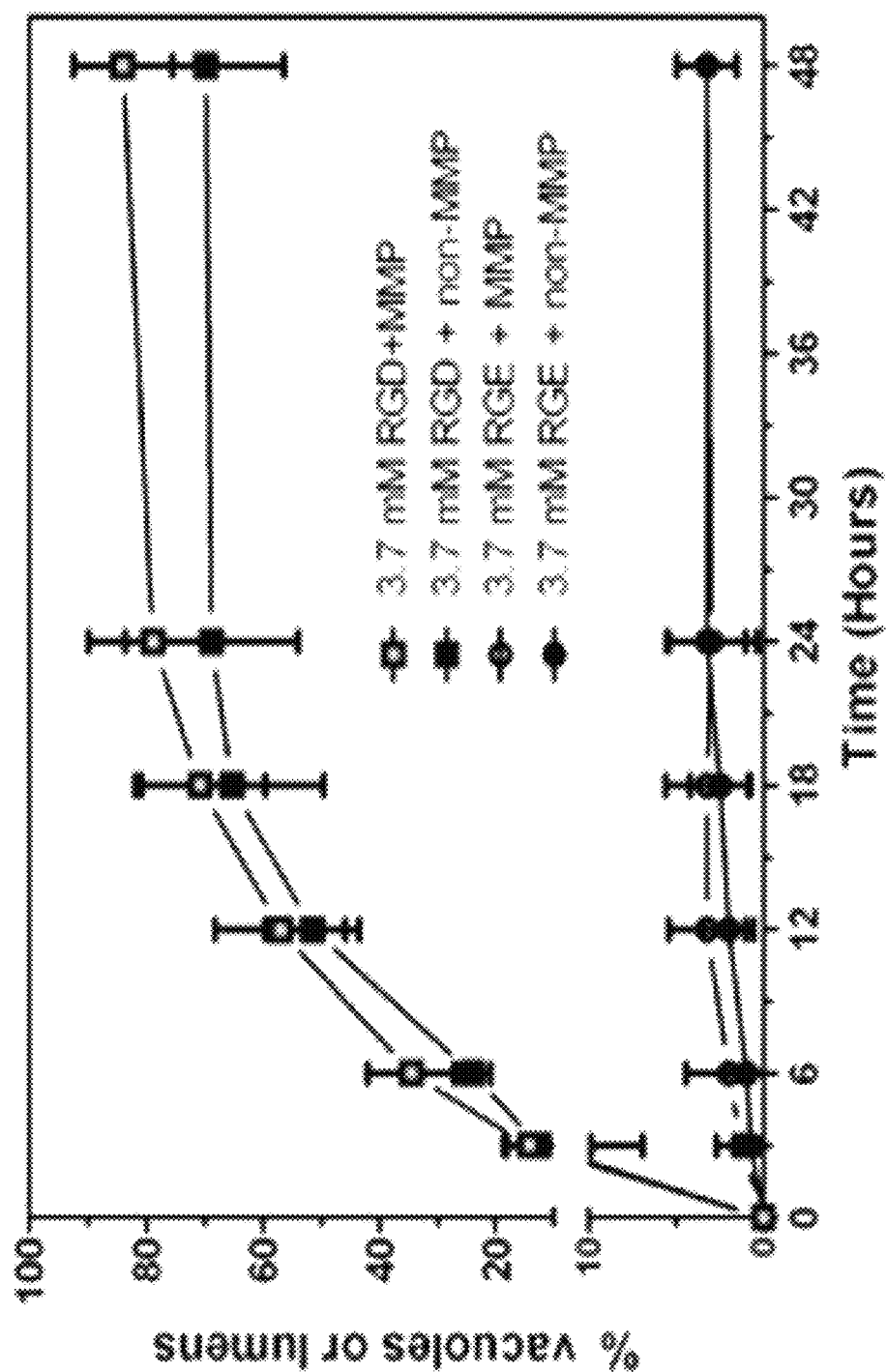
Figure 11D:
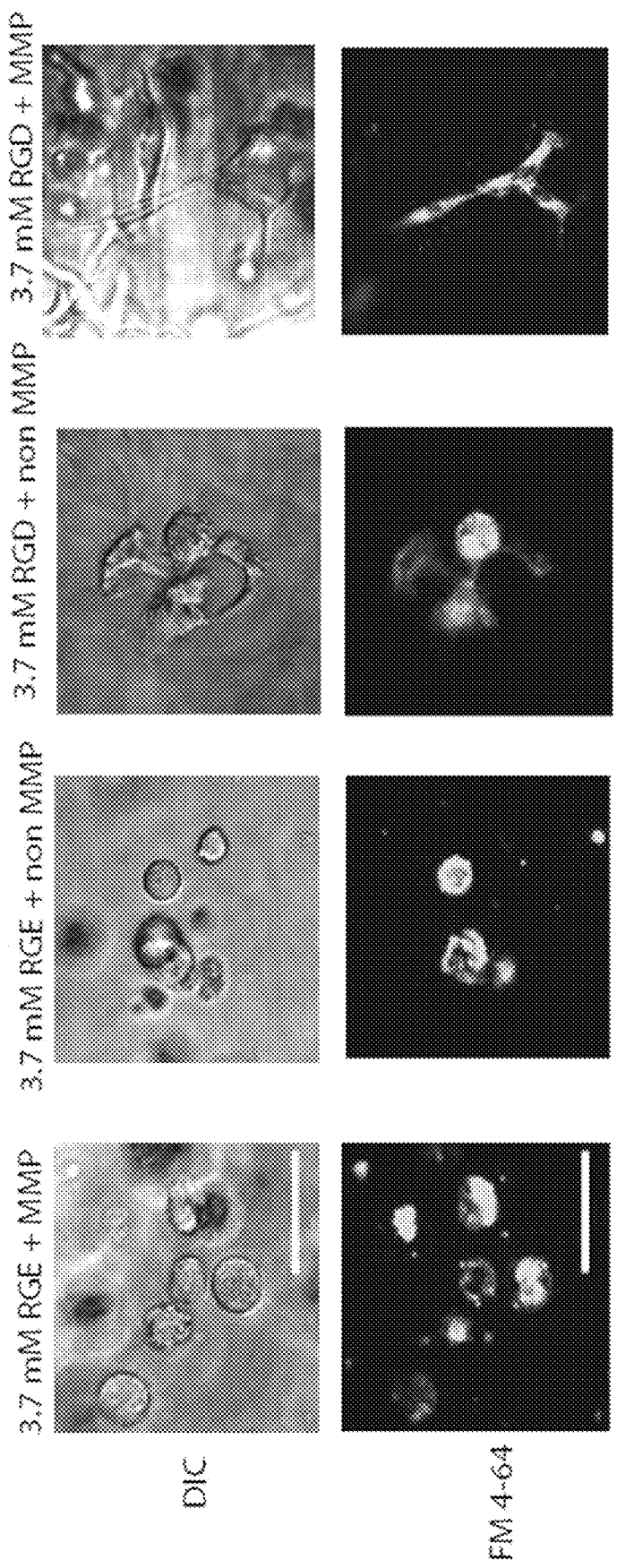
Figure 12B:
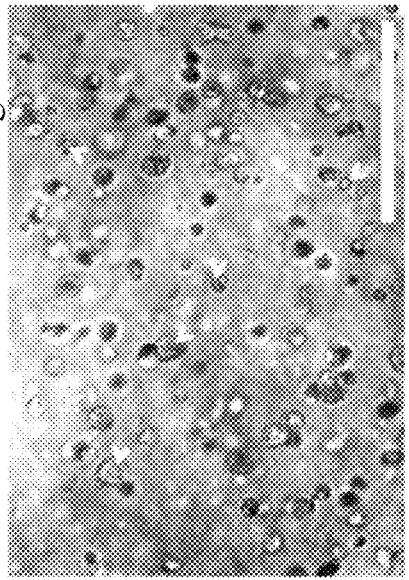
FIGS. 12A-12H: ECFC encapsulated within AHA gels (Day0-Day1). Vacuole formation observed few hours after cells encapsulation using: LM imaging (FIG. 12A) and higher magnification of vacuolated cells (indicated by arrowheads.
Figure 12D:
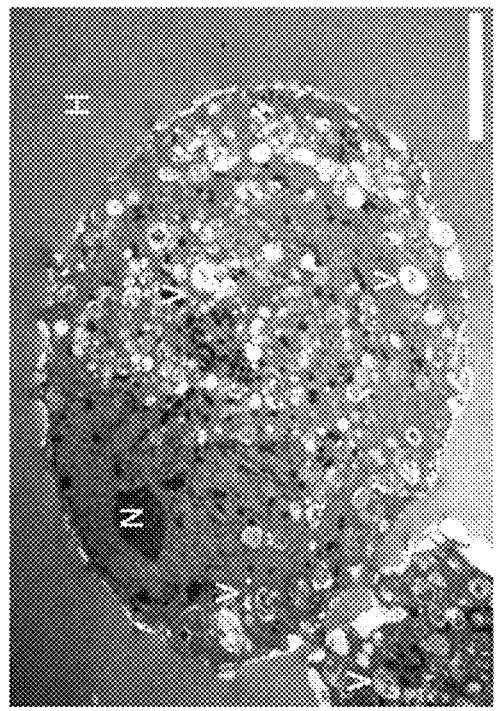
Figure 12A:
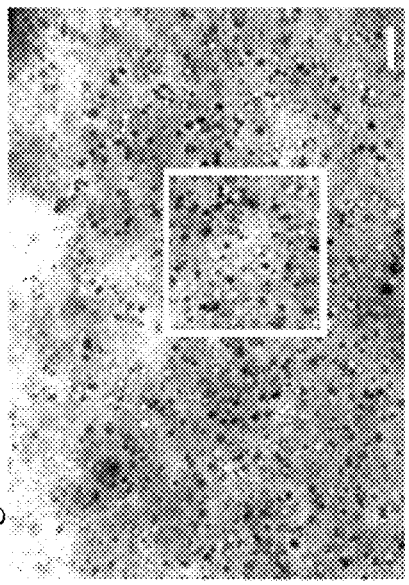
Figure 12C:
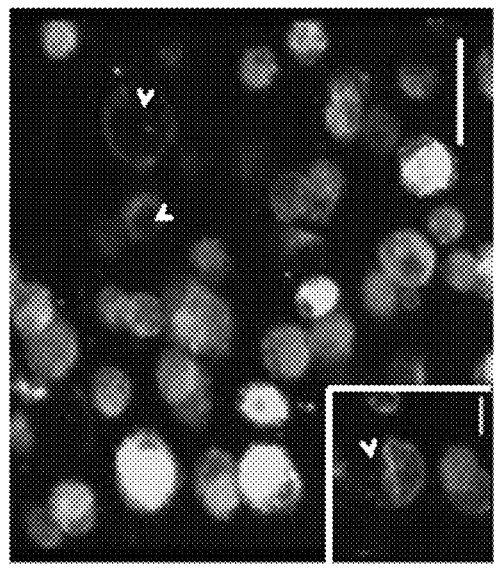
Figure 12E:
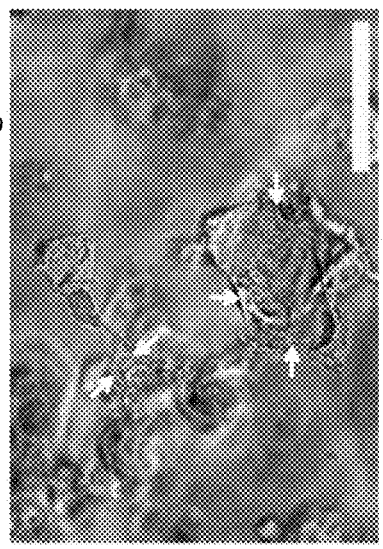
Figure 12F:
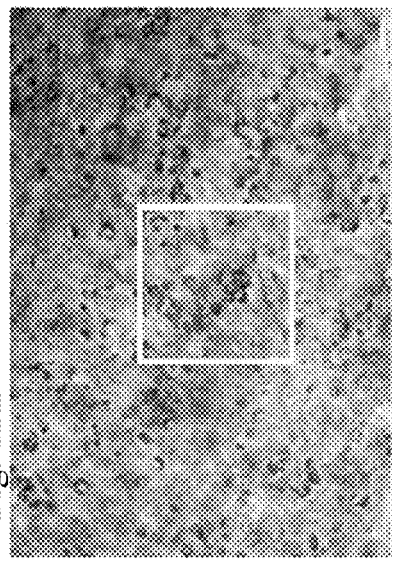
Figure 12H:
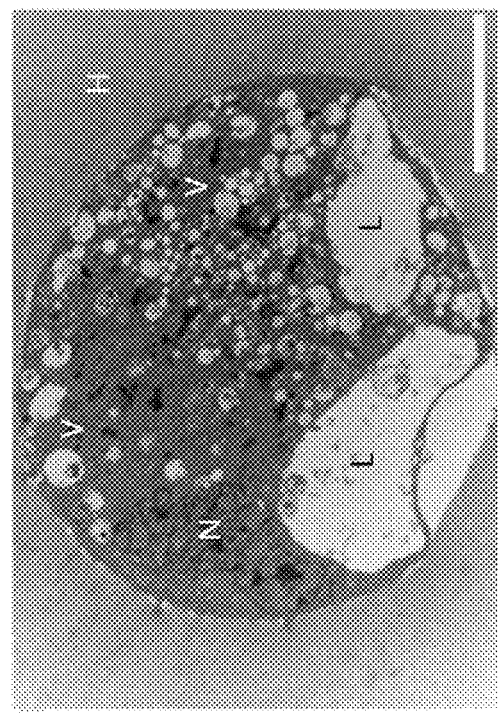
Figure 12G:
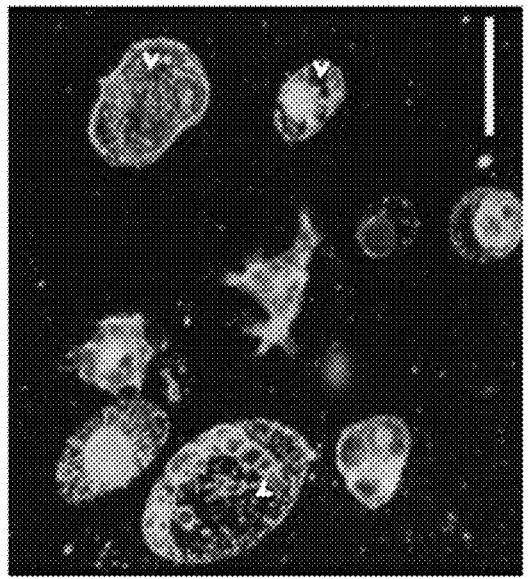
Figure 13C:
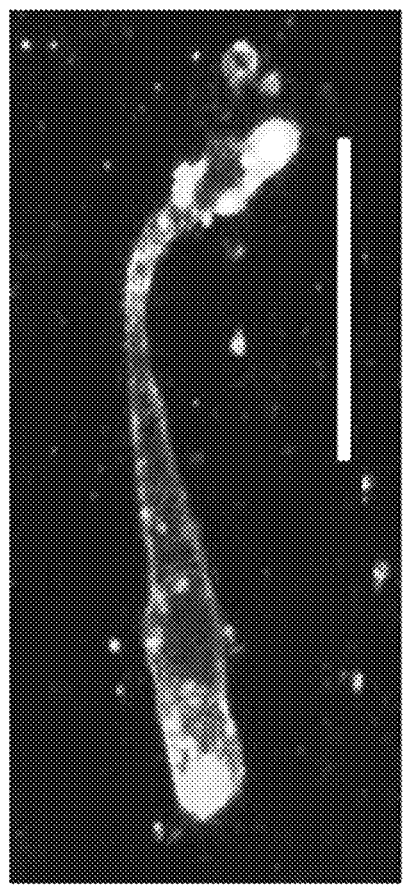
Figure 13D:
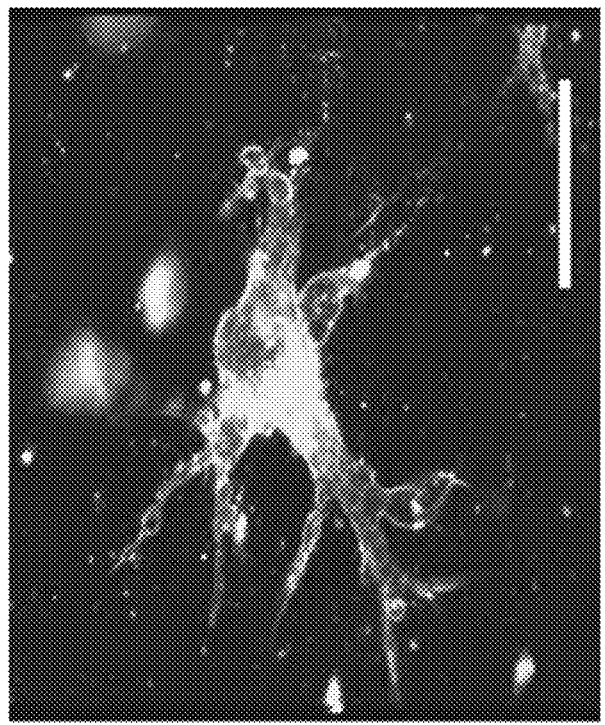
Figure 13H:
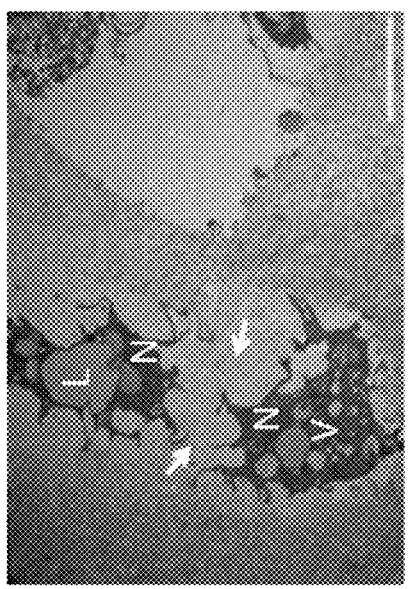
Figure 13F:
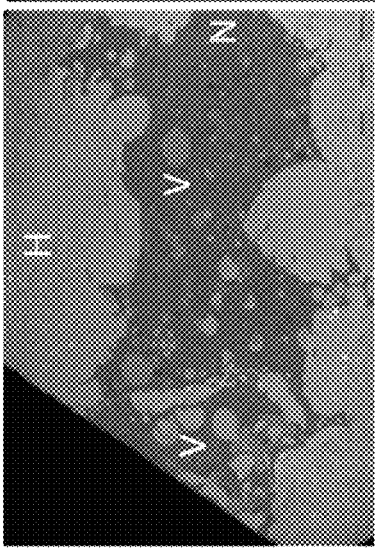
Figure 13G:
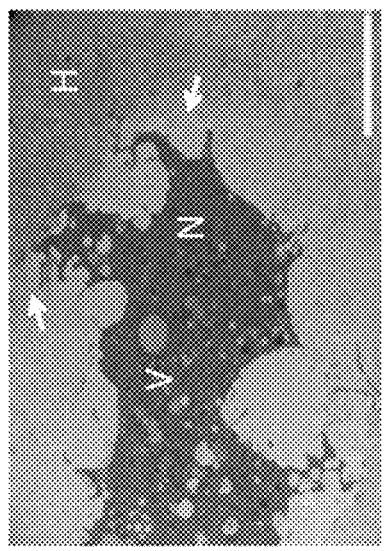
Figure 13E:
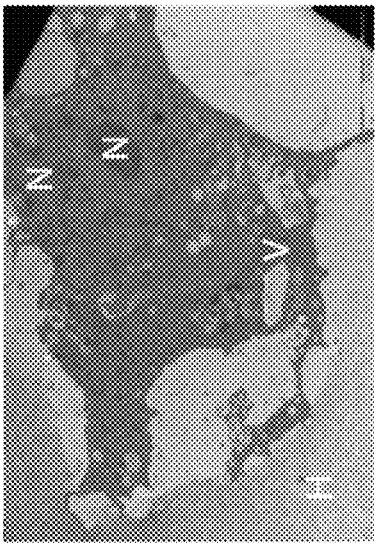

MMP-sensitive crosslinker incorporation into AHA hydrogels (See FIG. 11C) can be used. When RGE and MMP-insensitive crosslinker are used, no vacuole or lumen is observed. However, when RGD and MMP-insensitive crosslinker are used, some vacuoles with limited extent of lumen coalescence are observed. This suggest that RGD not only regulates vacuoles formation but also may localized MMPs activation on the cell surface (Xu et al., *The Journal of Cell Biology*, vol. 154, no. 5, pp. 1069-1080, 2001), enabling cell migration and coalescence into lumenal network.

These results show that RGD regulate vacuoles and lumen formation within synthetic AHA hydrogels in a dose dependent manner. Once vacuoles are formed, ECFCs migrate to the nearest neighbor to further coalescence into lumen structure. Like any other cell types, ECFCs migration within 3D matrix requires multiple balances between integrin activity, RGD ligand density, and proteolytic activity (Zaman et al., *Proceedings of the National Academy of Sciences*, vol. 103, no. 29, pp. 10889-10894, 2006). Medium RGD density which allow optimum cell migration (Gobin et al., *FASEB J.*: 01-0759fje), might be conducive for vascular morphogenesis to precede forward into lumen formation and network branching. These results are in agreement with what were observed in 2D culture when ECs were cultured on surface coated with fibronectin. In medium ECM density, with the appropriate RGD adhesion peptide, ECs collectively retracted and formed into branching capillary networks with hollow tubular structure (Ingber et al., *J. Cell. Biol.*, vol. 109, pp. 317-330, 1989).

Both MMP and adhesion molecules such as RGD are required for ECFCs tubulogenesis in AHA gels. Matrix parameters and their involvement in other signaling pathways during tubulogenesis can be decoupled to develop further gel characteristics.

Vascular Network Assembly of ECFC within AHA Gels

Encapsulation and Morphogenesis

Throughout the RGD and MMP experiments described above, vacuole formation is completed, reaching an optimum within 48 hours of encapsulation, which suggests that vacuole and lumen formation is completed at the end of day 1. Vacuoles can be observed within 3-6 hours after cell encapsulation at day 0 (FIGS. 12A-12D). This process continues with increased number and size of vacuoles, following with coalescence into larger lumen (FIGS. 12E-12H).

Branching and Sprouting

On the second day of culture, progression of tubulogenesis was observed through both branching and sprouting, with clear AHA hydrogel degradation at the cell microenvironment, changes in cell morphology toward elongation, and guiding channels forming between neighboring cells (FIGS. 13A-13H).

Network Formation and Growth

Figure 14B:
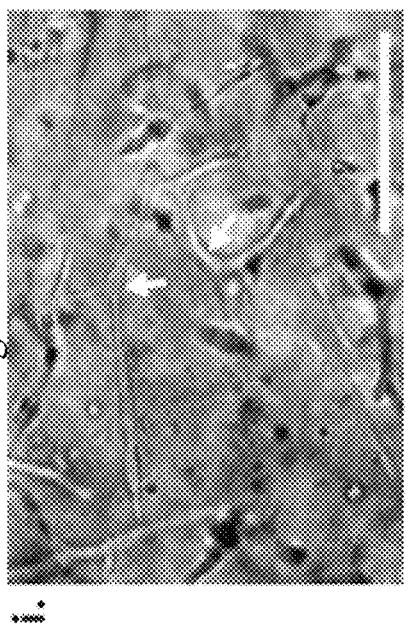
FIGS. 14A-14F: Complex vascular networks formed by ECFC within AHA hydrogels (Day 3). Growth of comprehensive vascular network is demonstrated using LM images at low magnification (FIG. 14A), while i (FIG. 14B) and ii (FIG. 14C) are high magnification of white boxes (arrow indicating branched and elongated vascular networks). Scale bars are 100 µm confocal analysis of vacuole vital stain FM 4-64 (FIG. 14D, cyan; nuclei in blue) demonstrate large lumen within the networks, which is also detected using orthogonal view (indicated by arrowhead.
Figure 14C:
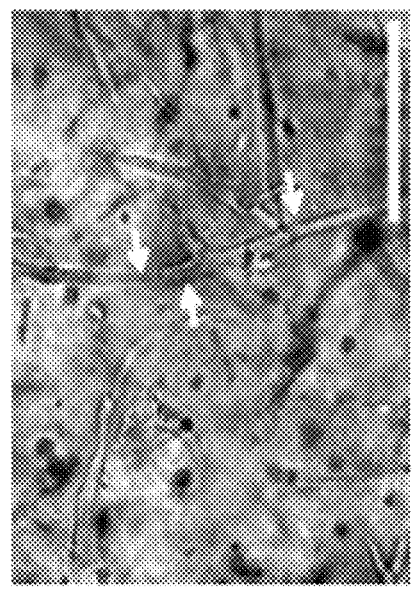
Figure 14A:
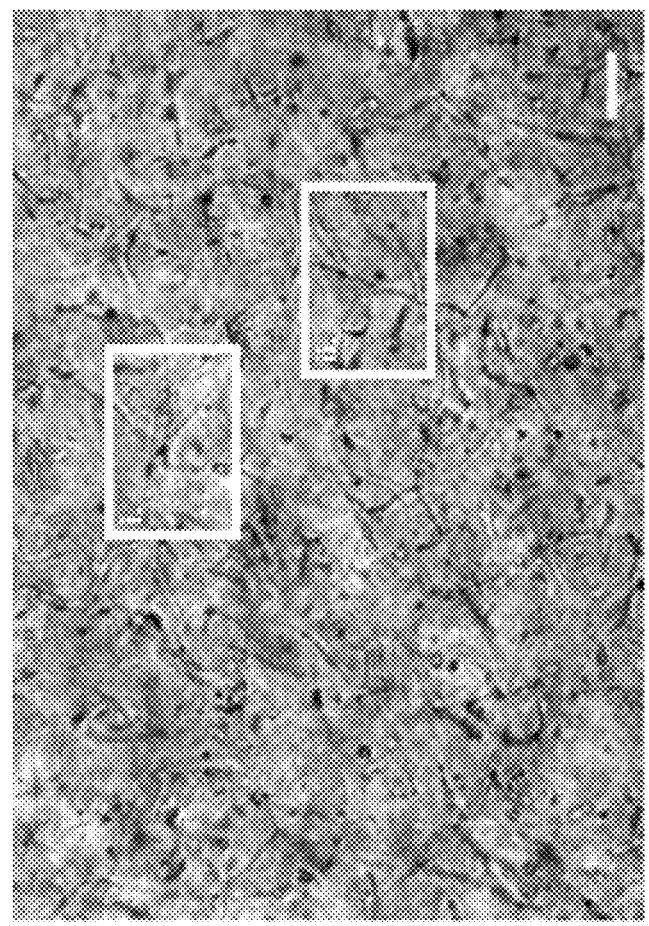
Figure 14D:
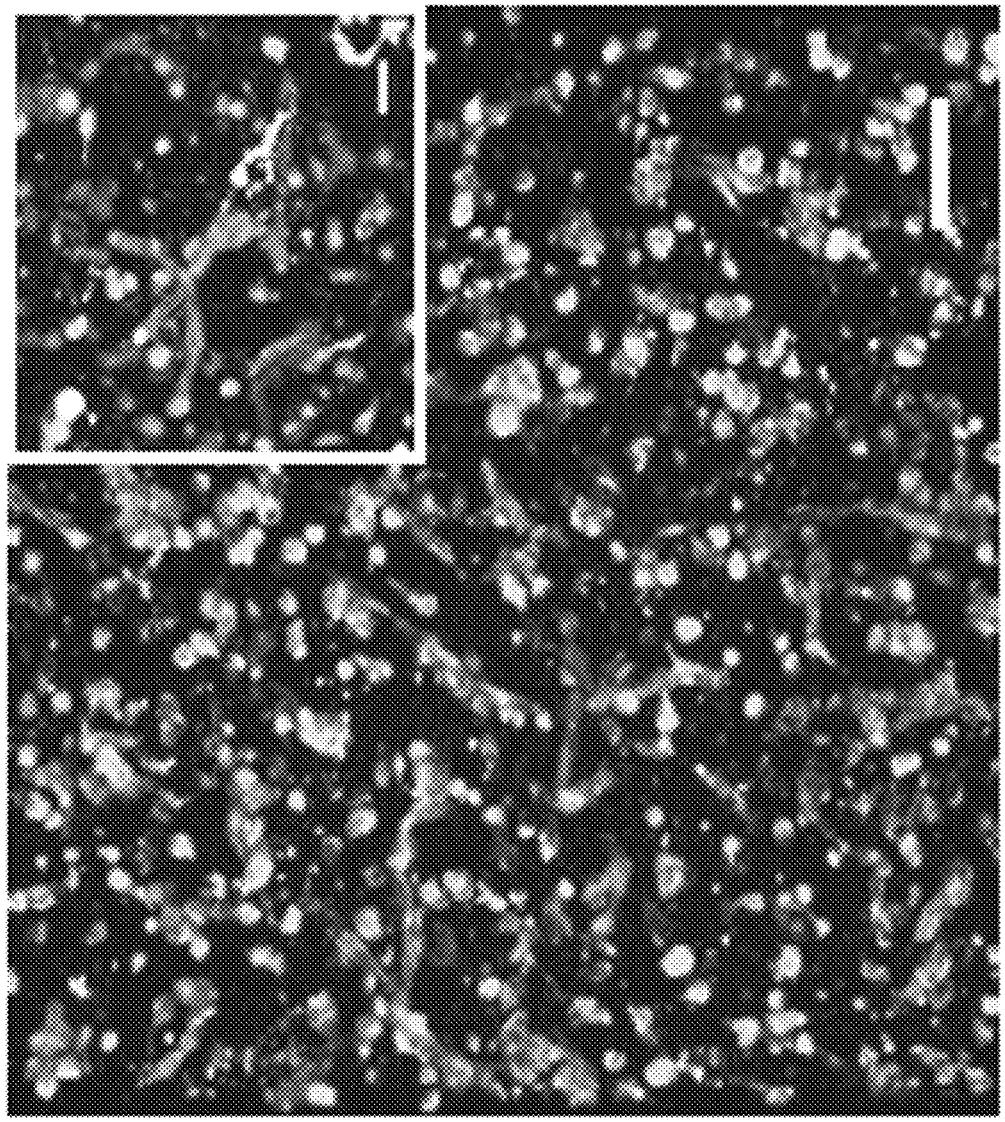
Figure 14E:
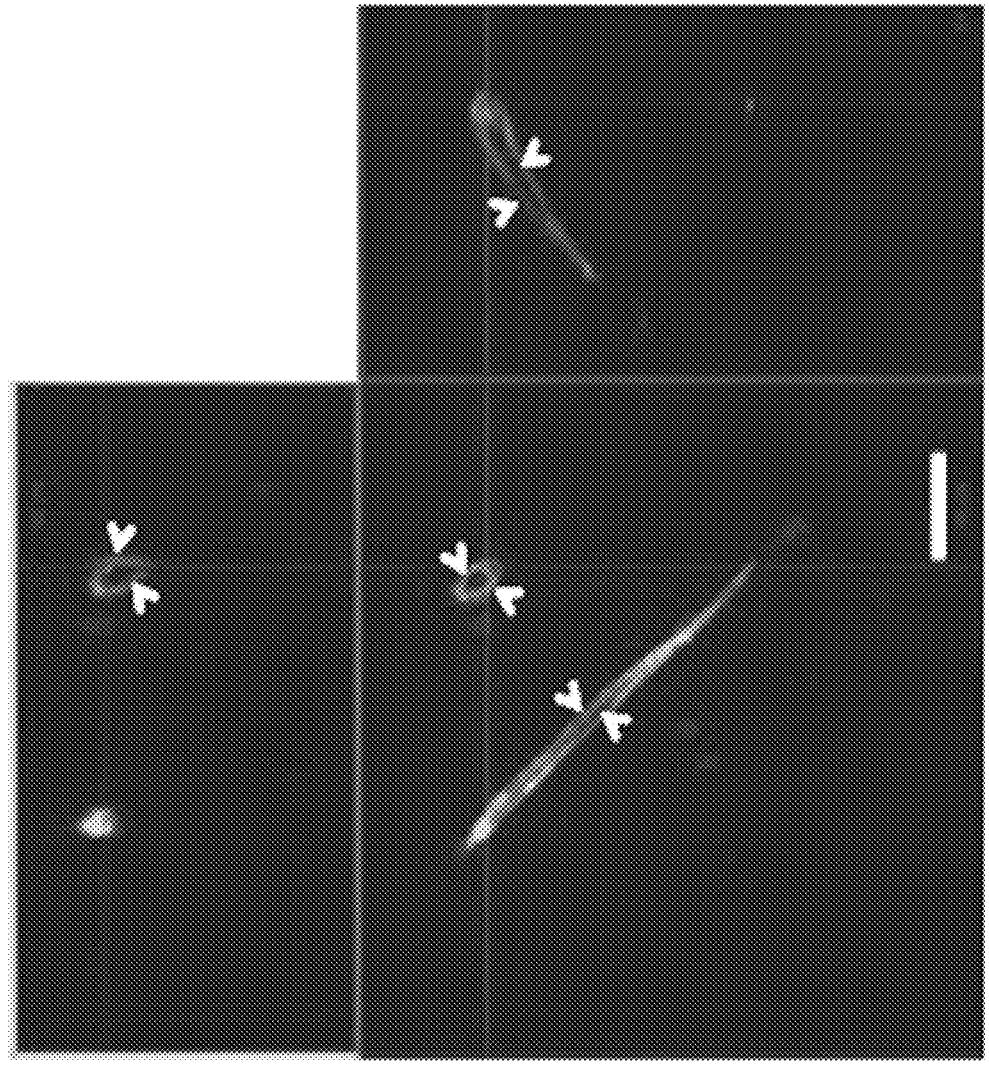
Figure 14F:
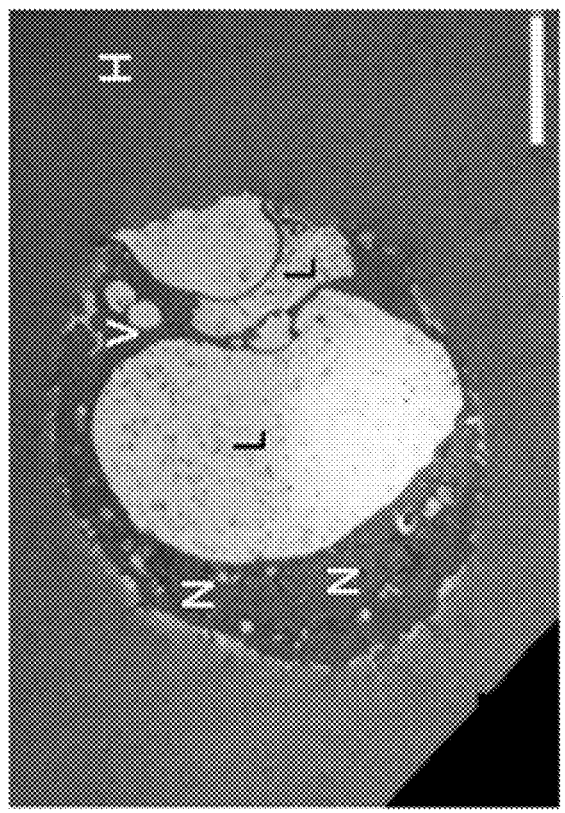
Figure 14F:
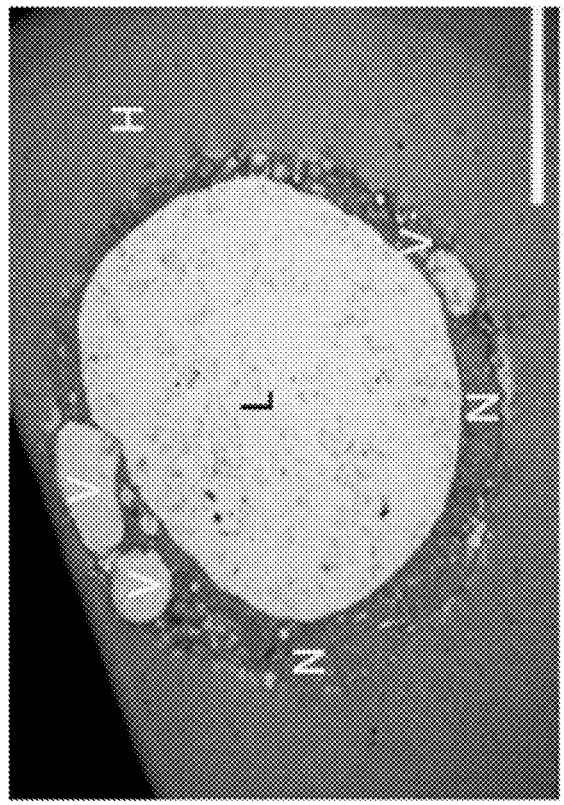

By day 3, vascular networks grow, and complex and comprehensive structures are clearly observed within AHA hydrogels (FIGS. 14A-14F). Open lumen within the networks is easily detected throughout the hydrogel (FIGS. 14D-14E)

Cell and Material Interaction: Kinetics of Matrix Properties Along Vascular Morphogenesis.

Figure 15A:
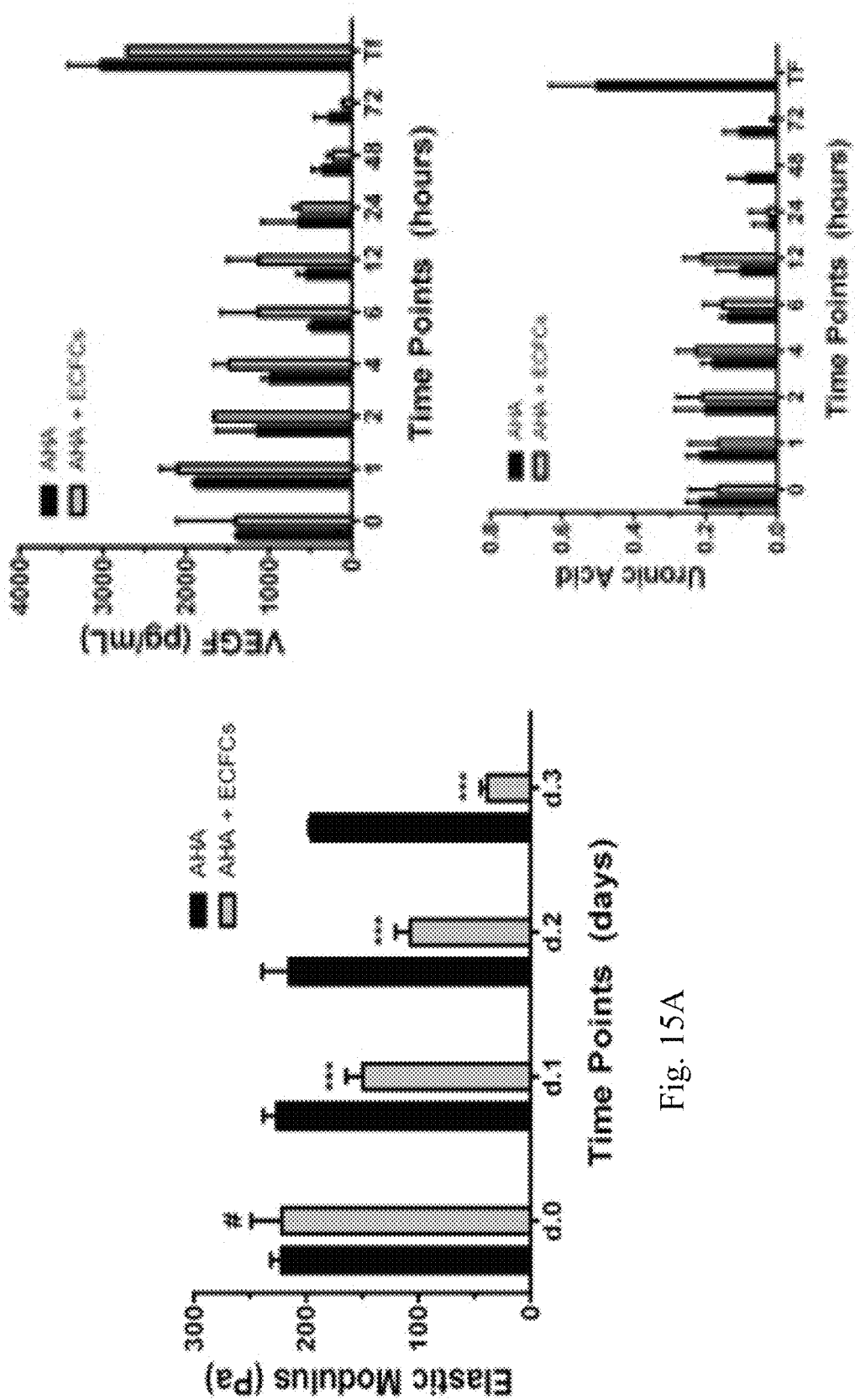

The dynamic interactions between ECFCs and AHA hydrogels were also characterized. AHA hydrogel stiffness decreases along the progression and network formation, reaching 40 Pa, which are in similar ranges to the experiments described above for HA-gelatin hydrogels (See also Hanjaya-Putra et al., Journal of Cellular and Molecular Medicine, vol. 14, no. 10, pp. 2436-2447, 2010). This further demonstrates that hydrogel stiffness should be controlled to enable in vitro vascular morphogenesis (FIG. 15A). The observation that enhanced vascular networks are formed as matrix stiffness is decreased, is consistent with results of previous studies using self-assembling peptide (Sieminski et al., Cell Biochem. Biophys., vol. 49, pp. 73-83, 2007), matrigel (Deroanne et al., Cardiovasc. Res., vol. 49, pp. 647-658, 2001), collagen (Sieminski et al., Exp. Cell. Res., vol. 297, pp. 574-584, 2004), and fibrin gels (Stéphanou et al., Microvascular Research, vol. 73, no. 3, pp. 182-190, 2007; Kniazeva et al., Am. J. Physiol. Cell Physiol., vol. 297, no. 1, pp. C179-187, 2009).

Figure 15D:
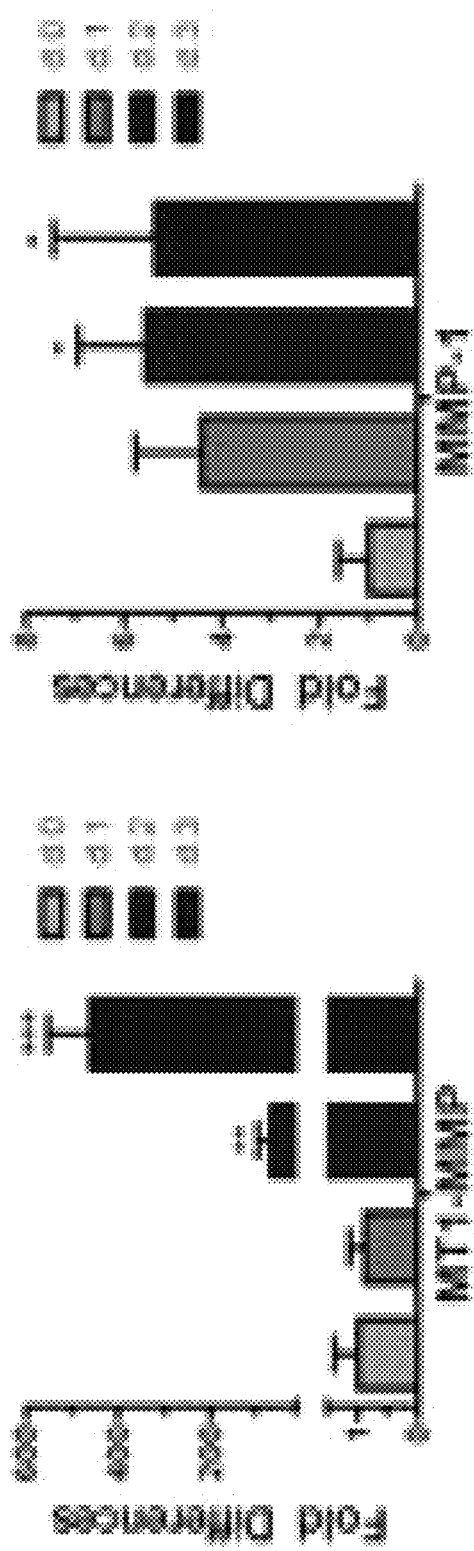
Figure 15D:
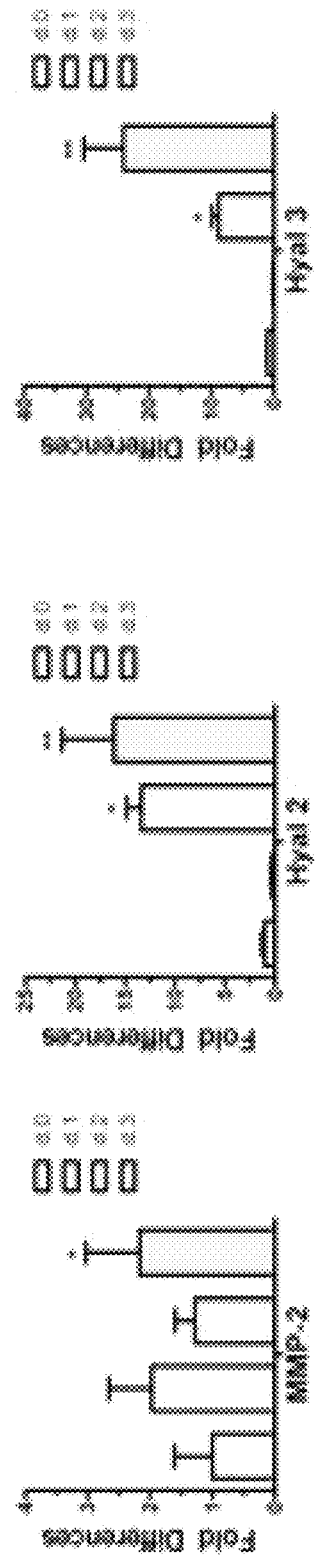

The optimal magnitude of matrix stiffness for different gel types is a bit different, but this can be attributed to the specificity of different gels, a universal nature of this trend in various gel types emphasizes that cellular remodeling is importance for vascular morphogenesis. Therefore, a SEM study was done to further investigate cellular remodeling of ECFCs within AHA hydrogels. SEM images of day 1 show rounded cells within complex hydrogel mesh ultrastructure, which by day 3 are spread in between large guiding microchannels (FIG. 15C). These guiding microchannels are formed by MMPs and hyaluronidases, which expression is increased by ECFCs along the 3-day culture period (FIG. 15D). Previous studies in 3D collagen gels have shown that ECs create "vascular guidance tunnel," to allow cells migration and vascular networks formation. Within these physical spaces ECs move in MT1-MMP dependent manner to form complex lumen structures (Sacharidou et al., Blood, vol. 115, no. 25, pp. 5259-5269, 2010; Stratman et al., Blood, vol. 114, no. 2, pp. 237-47, 2009).

Additional Growth Factors

SDF-1 and TNF-alpha are known to induce MMP production in ECs (Han, Tuan et al. 2001), in which an optimum MMP secretion was needed to allow vascular branching and network formation (Sacharidou et al., Blood, vol. 115, no. 25, pp. 5259-5269, 2010; Iruela-Arispe et al., Dev. Cell, vol. 16, pp. 222-231, 2009; Stratman et al., Blood, vol. 114, no. 2, pp. 237-47, 2009). In hydrogels of the present invention, encapsulated SDF-1 and TNF-alpha can be used to induce MMP production to allow sprouting and invasion, as was reported in other synthetic hydrogels (Raeber et al., Biophysical Journal, vol. 89, no. 2, pp. 1374-1388, 2005).

Monitoring

The kinetics of cellular remodeling can be observed at various points throughout vascular morphogenesis by monitoring the uronic acid, a byproduct of the AHA degradation, released in the media. As vascular morphogenesis progresses, ECFCs secrete MMP-1, -2, MT1-MMP, Hyal-2, and Hyal-3, the inventive AHA hydrogels are degraded and as a result matrix stiffness decreases.

During this process, AHA hydrogel was degraded and released the uronic acid byproduct to the culture media (FIG. 15F), enabling progression in tubulogenesis. As the hydrogels were degraded, about 80% of the encapsulated VEGF is released into the media providing a soluble cue for the ECFCs to undergo tubulogenesis (FIG. 15E). These data demonstrate that a suitable synthetic material provides a responsive and dynamic niche to accommodate vascular morphogenesis, through activation of proteases specific for the tubulogenesis microenvironment (Lutolf et al., Nature Biotechnology, vol. 23, no. 1, pp. 47-55, 2005; Stratman et al., Blood, vol. 114, no. 2, pp. 237-47, 2009).

Molecular Regulation of Vascular Morphogenesis in AHA Gels.

Figure 16A:
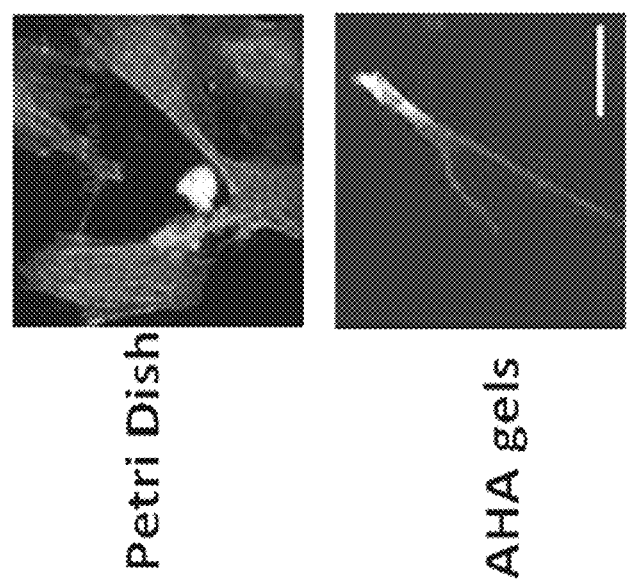
FIGS. 16A-16D: Molecular regulation of vascular morphogenesis in AHA gels. Integrin blocking assay revealed that RGD-dependent vacuolation and lumen formation within AHA hydrogels are regulated by $\alpha V\beta 3$ and $\alpha 5\beta 1$ integrins, but not by, $\alpha 2\beta 1$ integrins (16A). Real time RT-PCR analysis show downregulating expression of $\alpha V$, $\alpha 5$, $\beta 1$ and $\beta 3$, along the culture period of encapsulated ECFCs (FIG. 16B). Confocal analysis (FIG. 16C) revealed the membrane localization of MMP-1, and MMP-2 (both in green; actin in red; nuclei in blue) in the branching and sprouting ECFC (high magnification showed in the inserts). Scale bars are 50 µm. Real time RT-PCR analysis show increase expression of TIMP-2 and TIMP-3 by encapsulated ECFCs along the 3 days culture period (FIG. 16D).
Figure 16A:
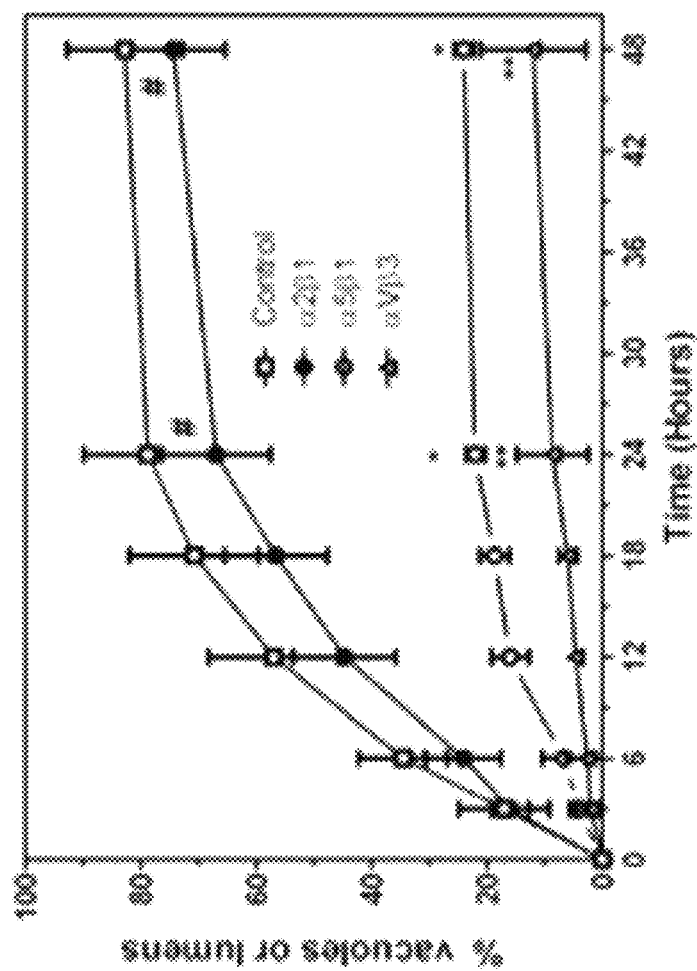
Figure 16B:
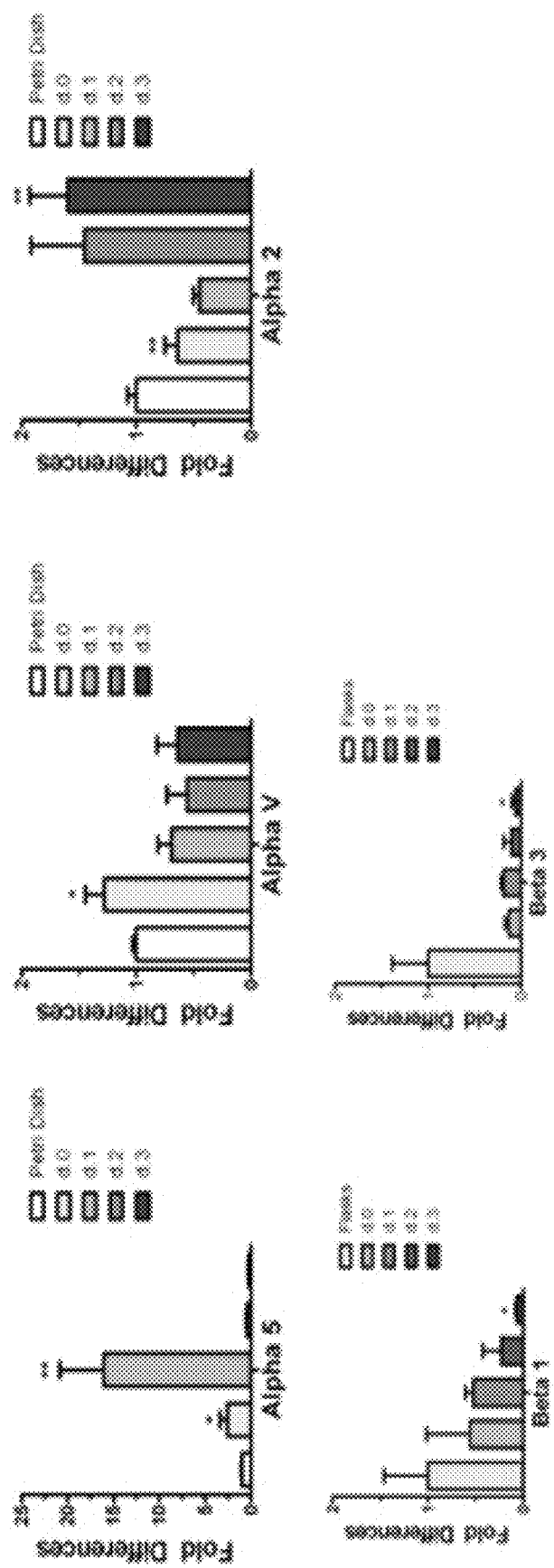
Figure 16C:
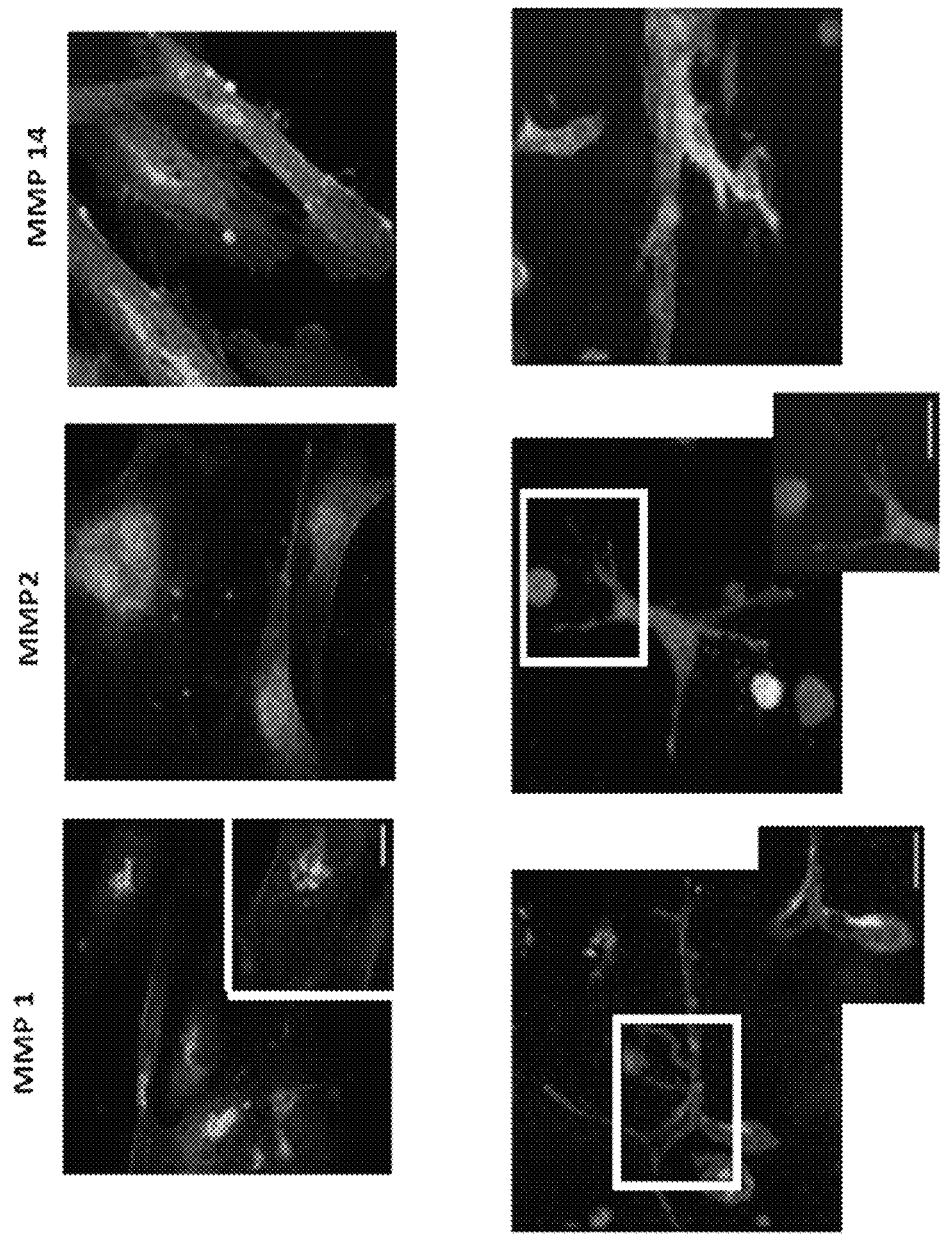
Figure 16D:
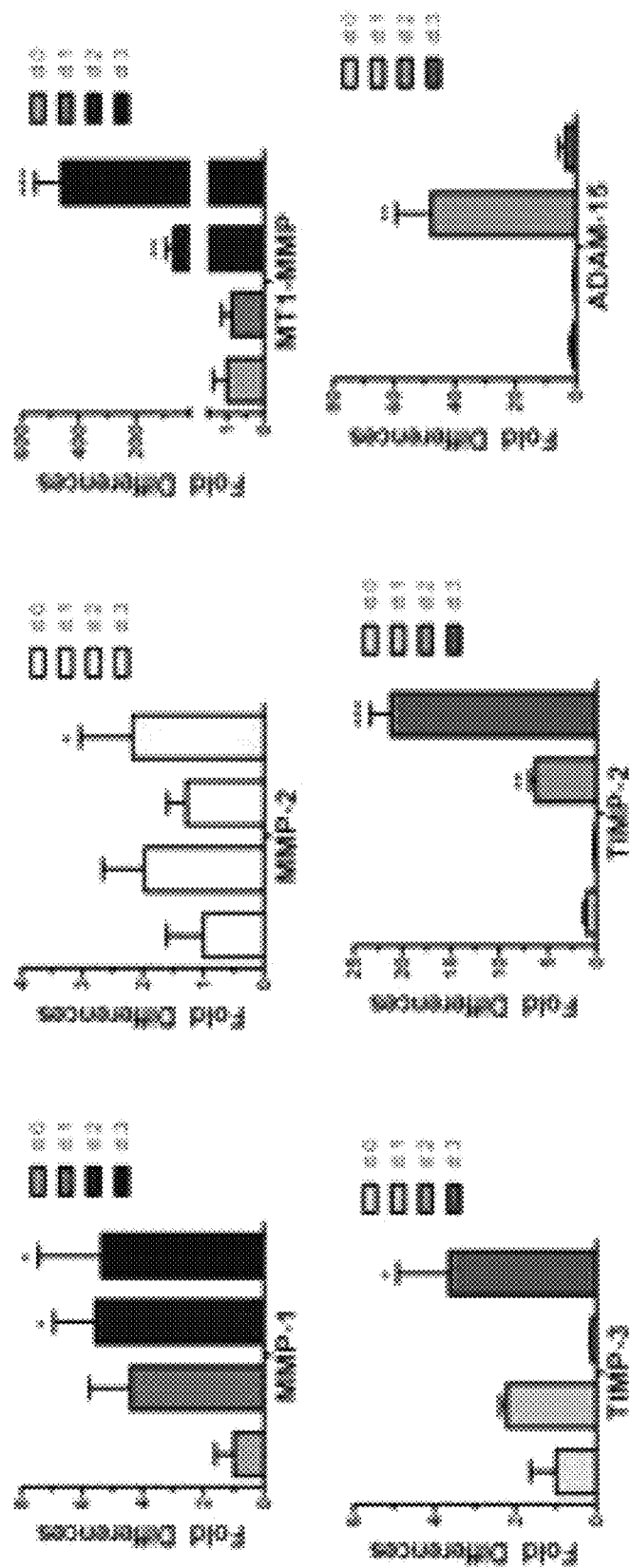

To determine the integrin subunit that regulates vacuole and lumen formation within this synthetic AHA hydrogels, integrin blocking experiment was performed. Three integrins $\alpha V\beta 3$, $\alpha 5\beta 1$, $\alpha 2\beta 1$ are known to regulate vacuole and lumen formation in collagen and fibrin gels (Bayless et al., Am. J. Pathol., vol. 156, no. 5, pp. 1673-1683, 2000). Blocking $\alpha 2\beta 1$ integrin did not significantly reduced vacuole and lumen formation compared to control (FIG. 16A). However, blocking $\alpha 5\beta 1$ integrin reduced the extent of vacuole and lumen formation to 20%. Moreover, blocking $\alpha V\beta 3$ significantly blocked vacuole and lumen formation down to 10% after 48 hours. Indeed, $\alpha v$ is found to be highly expressed on day 0, while decreasing along the cultures period; $\alpha 5$ upregulate on day 1 of culture; whereas the expression of both $\beta 1$ and $\beta 3$ is decreased on days 2 and 3 of the culture period (FIG. 16B). Altogether, in the synthetic culture system, integrin subunits $\alpha 5$, $\alpha V$, $\beta 1$ and $\beta 3$ are highly expressed at early stage of vascular morphogenesis (day 0-day 1), to initiate vacuole and lumen formation through RGD-integrin signaling cascade. This phenomena was reported in fibrin gels (Bayless et al., Am. J. Pathol., vol. 156, no. 5, pp. 1673-1683, 2000) where RGD induce vacuole and lumen formation through $\alpha 5\beta 1$ and $\alpha V\beta 3$, the main RGD-binding integrins (Xu et al., The Journal of Cell Biology, vol. 154, no. 5, pp. 1069-1080, 2001). The integrin expression is offset by the increase in MMPs expression to support branching and network formation (day 2-day 3) (FIG. 16D). Specifically, both MMP-1 and MMP-2 are localized near the cell membrane at day 2, where branching and sprouting start to take place (FIG. 16C). In collagen and fibrin gels, TIMPs expressed by ECs and pericytes were shown to stabilize mature vascular networks (Saunders et al., J. Cell Biol., vol. 175, pp. 179-191, 2006). Indeed, at the end of day 3, stabilization of the vascular networks formed within AHA hydrogel is evident as indicated by the increased expression of TIMP-2 and TIMP-3 by ECFCs (FIG. 16D).

Functionality of ECFC Vascular Networks within AHA Hydrogels

Figure 17C:
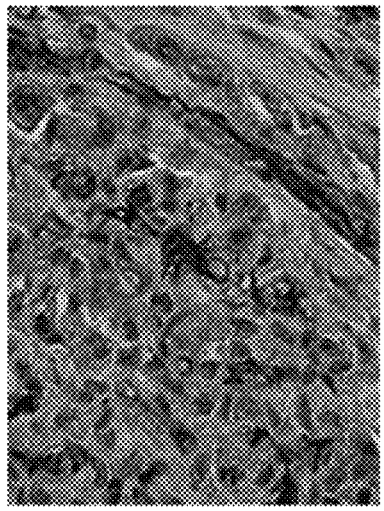
Figure 17C:
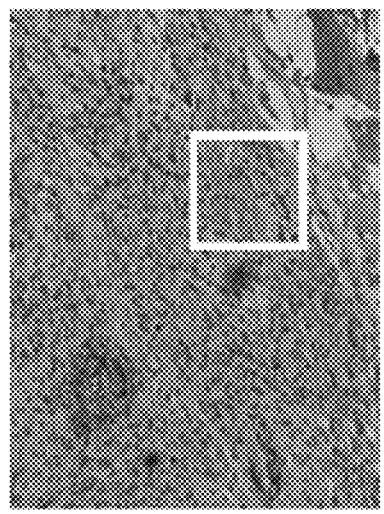
Figure 17D:
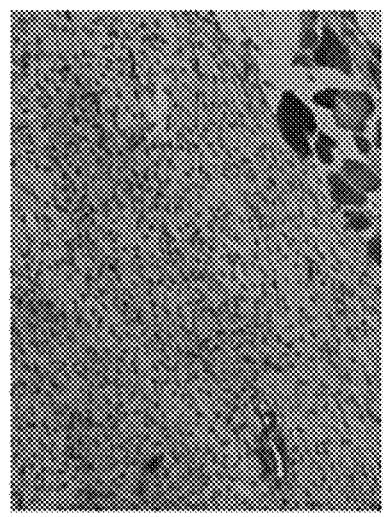

To determine the functionality of the engineered vascular networks, 3-days matured and stabilized vascular constructs were implanted into nude mice. Histological analysis revealed that the AHA hydrogels were completely degraded by 1-2 weeks in vivo, replaced by active or dead macrophages and tissue ingrowth (FIG. 17A). Blood vessels in various sizes are found at the periphery and center of the hydrogels (FIG. 17B). Most of the microvessels at the center of the hydrogels are positive for human CD31 and perfused with blood cells, indicative that the implanted human vascular networks were able to anastomose with the host vasculatures to form functional vessels (vasculogenesis) (FIG. 17C). Some of the microvessels contain both human CD31+ cells and host cells, demonstrating that the implanted ECFCs participate in the angiogenesis of the host vasculatures as well (FIGS. 17C-17D).

We claim:

1. A method of preparing a vascular lineage cell growth medium comprising
    chemically bonding an adhesion promoter to an oligosaccharide,
    combining the chemically bonded adhesion promoter and oligosaccharide with at least one growth factor,
    adding a crosslinking peptide moiety,
    curing the combination to form a hydrogel, wherein the hydrogel has a Young's modulus between about 10 Pa and about 500 Pa; and
    wherein the growth factor is an amount sufficient to promote vasculogenesis and tube formation, and sufficient to stimulate MMP production in vascular lineage cells.

2. The method of claim 1, wherein the oligosaccharide is hyaluronic acid that is from about 20% to about 90% acrylate modified and is present in an amount of about 1 wt % to about 4 wt %.

3. The method of claim 1, wherein the adhesion promoter is present at a concentration of from about 0.1 mM to about 20 mM.

4. The method of claim 1, wherein the crosslinking peptide moiety is present at a concentration of from about 1 mM to about 8 mM.

5. The method of claim 1, wherein the growth factor is present at a concentration of from about 25 ng/ml to about 200 ng/ml.

6. The method of claim 1, wherein the hydrogel allows formation of capillary-like structures (CLSs) with extended vacuoles and open lumens from vascular lineage cells.

7. The method of claim 1, wherein the hydrogel and crosslinking peptide moiety are cleavable by an enzyme.

8. The method of claim 7, wherein the enzyme is a matrix metalloproteinase.

9. The method of claim 8, wherein the matrix metalloproteinase is at least one of MMP-1, MMP-2 or MMP-10.

10. The method of claim 1, wherein the crosslinking moiety peptide comprises the sequence SEQ ID NO: 1.

11. The method of claim 1, wherein the adhesion promoter promotes vascular lineage cell adhesion to the hydrogel and promotes vacuole and lumen formation in vascular lineage cells.

12. The method of claim 1, wherein the hydrogel has a Young's modulus between about 10 Pa and about 250 Pa.

13. The method of claim 1, wherein the oligosaccharide is modified with an acryl group.

14. The method of claim 1, wherein the oligosaccharide is acrylated hyaluronic acid.

15. The method of claim 1, wherein the growth factor is selected from the group consisting of VEGF, TNFα, SDF1-α, bFGF, angiopoetin-1, PDGF, TGF-β, PIGF or combinations thereof.

16. The method of claim 1, wherein the adhesion promoter is a peptide that includes an RGD sequence and a reactive functional group that is capable of bonding the adhesion promoter to the oligosaccharide.

17. A vascular lineage cell growth medium prepared by the method of claim 16, wherein the oligosaccharide is acrylated hyaluronic acid.

18. A method of inducing vascular cell morphogenesis in vivo comprising contacting a subject with a vascular construct comprising the medium of claim 17 and vascular lineage cells.

19. The method of claim 18, wherein the crosslinking moiety peptide comprises the sequence SEQ ID NO: 1.

20. The method of claim 18, wherein the growth factor is selected from the group consisting of VEGF, TNFα, SDF1-α, bFGF, angiopoetin-1, PDGF, TGF-β, PIGF or combinations thereof.

21. The method of claim 1, wherein the oligosaccharide is modified with a thiol group.

* * * * *

SEQUENCE LISTING

```
<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Cys Arg Asp Gly Pro Gln Gly Ile Trp Gly Gln Asp Arg Cys Gly
1               5                   10                  15

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Cys Gly Tyr Gly Arg Gly Asp Ser Pro Gly
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Cys Gly Tyr Gly Arg Asp Gly Ser Pro Gly
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Cys Arg Asp Gly Asp Gln Gly Ile Ala Gly Phe Asp Arg Cys Gly
1               5                   10                  15
```